(12) United States Patent
Kurup

(10) Patent No.: US 12,410,173 B1
(45) Date of Patent: Sep. 9, 2025

(54) SUBSTITUTED PYRROLO[2,3-D]PYRIMIDINES AS INHIBITORS FOR MULTI-RESISTANT CANCERS

(71) Applicant: FERRIS STATE UNIVERSITY, Big Rapids, MI (US)

(72) Inventor: Sonali Raghavan Kunjunni Kurup, Big Rapids, MI (US)

(73) Assignee: Ferris State University, Big Rapids, MI (US)

( * ) Notice: Subject to any disclaimer, the term of this patent is extended or adjusted under 35 U.S.C. 154(b) by 0 days.

(21) Appl. No.: 18/376,754

(22) Filed: Oct. 4, 2023

Related U.S. Application Data

(63) Continuation of application No. 17/459,558, filed on Aug. 27, 2021, now Pat. No. 11,814,388.

(60) Provisional application No. 63/071,446, filed on Aug. 28, 2020.

(51) Int. Cl.
*C07D 487/04* (2006.01)
(52) U.S. Cl.
CPC .................. *C07D 487/04* (2013.01)
(58) Field of Classification Search
CPC .................................................. C07D 487/04
USPC ...................................................... 544/280
See application file for complete search history.

(56) References Cited

U.S. PATENT DOCUMENTS

| | | | |
|---|---|---|---|
| 6,180,636 | B1 | 1/2001 | Traxler et al. |
| 7,560,551 | B2 | 7/2009 | Cee et al. |
| 8,404,694 | B2 | 3/2013 | White et al. |
| 9,126,935 | B2 | 9/2015 | Deak et al. |
| 2004/0242600 | A1 | 12/2004 | Bold et al. |
| 2004/0248911 | A1 | 12/2004 | Bold et al. |
| 2006/0211678 | A1 | 9/2006 | Ahmed et al. |
| 2009/0111805 | A1 | 4/2009 | Morris et al. |
| 2010/0204197 | A1 | 8/2010 | Diels et al. |
| 2011/0160203 | A1 | 6/2011 | Liu et al. |
| 2015/0246923 | A1 | 9/2015 | Wang et al. |
| 2017/0121346 | A1 | 5/2017 | Sprengeler et al. |
| 2020/0165246 | A1 | 5/2020 | Deng et al. |

FOREIGN PATENT DOCUMENTS

| | | |
|---|---|---|
| CN | 109384782 A | 2/2019 |
| WO | 2003013541 A1 | 2/2003 |
| WO | 2006017443 A2 | 2/2006 |
| WO | 2006090261 A1 | 8/2006 |
| WO | 2009016132 A1 | 2/2009 |
| WO | 2013078254 A1 | 5/2013 |
| WO | 2015131005 A1 | 9/2015 |
| WO | 2017075394 A1 | 5/2017 |

OTHER PUBLICATIONS

Gangjee, et al. Bioorganic & Medicinal Chemistry Letters, 18(10), 2010, 3575-3587.*
Adel et. al., "Identification of new pyrrolo[2,3-d]pyrimidines as potent VEGFR-2 tyrosine kinase inhibitors: Design, synthesis, biological evaluation and molecular modeling", Bioorg Chem. Dec. 2018; 81:612-629.
Fischer et al., "Discovery of novel dual inhibitors of receptor tyrosine kinases EGFR and PDGFR-Î² related to anticancer drug resistance", Journal of Enzyme Inhibition and Medicinal Chemistry, 33:1, 1-8 (2018).
Reiersølmoen et al., "Identification of fused pyrimidines as interleukin 17 secretion inhibitors", Eur J Med Chem. Jul. 15, 2018; 155:562-578.
Reiersølmoen et al., "Potent and selective EGFR inhibitors based on 5-aryl-7H-pyrrolopyrimidin-4-amines", Bioorg Chem. Jul. 2019;88:102918.

(Continued)

*Primary Examiner* — Douglas M Willis
(74) *Attorney, Agent, or Firm* — WARNER NORCROSS + JUDD LLP

(57) ABSTRACT

Substituted pyrrolo[2,3-d]pyrimidines as inhibitors for multi-resistant cancers are described herein. Also provided herein are methods of forming the compounds, methods for inhibiting aurora kinase A and/or aurora kinase B activity and epidermal growth factor activity, methods of treating, ameliorating, or preventing cancer, and uses of the compounds for inhibiting aurora kinase A and/or aurora kinase B activity and epidermal growth factor receptor kinase activity. The compounds are generally of the formulas as illustrated herein, including those of Formula (I-2) or a pharmaceutically acceptable salt thereof:

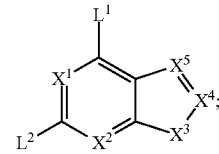

(I-2)

wherein: $X^1$ is N; $X^2$ is N; $X^3$ is —NH—; $X^4$ is N or $CR^2$; $X^5$ is CH, $CCH_3$, or CCOOH; $L^1$ is —$NR^4$—$R^1$; $L^2$ is $NH_2$ or H; $R^1$ is:

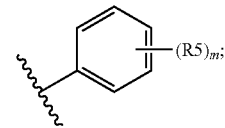

$R^2$ is H, COOH, a 5-membered heteroaryl, or $X^6R^3$; $X^6R^3$ is as described herein; $R^4$ is H; R5 is as described herein; and m is 1, 2, 3, 4, or 5.

15 Claims, 26 Drawing Sheets

(56) References Cited

OTHER PUBLICATIONS

Miyaura et al., "Palladium-Catalyzed Cross-Coupling Reactions of Organoboron Compounds", Chem. Rev. 1995, 95, 2457-2483.

Zhang, et al., "Palladium-Imidazol-2-ylidene Complexes as Catalysts for Facile and Efficient Suzuki Cross-Coupling Reactions of Aryl Chlorides with Arylboronic Acids", J. Org. Chem. 1999, 64, 3804-3805.

Zhao, et al., "Modulation of kinase-inhibitor interactions by auxiliary protein binding: Crystallography studies on Aurora A interactions with VX-680 and with TPX2", Protein Science 2008, 17, 1791-1797.

Yun et al., "The T790M mutation in EGFR kinase causes drug resistance by increasing the affinity for ATP", PNAS 2008, 105, 2070-2075.

Girdler et al., "Molecular Basis of Drug Resistance in Aurora Kinases", Chemistry & Biology 2008, 15, 552-562.

Le Brazidec et al., "Structure-based design of 2,6,7-trisubstituted-7H-pyrrolo[2,3-d]pyrimidines as Aurora kinases inhibitors", Bioorganic & Medicinal Chemistry Letters 2012, 22, 4033-4037.

Radi et al., "Design, Synthesis, and Biological Evaluation of Pyrazolo[3,4-d]pyrimidines Active in Vivo on the BCR-ABL T315I Mutant", Journal of Medicinal Chemistry 2013, 56, 5382-5394.

Gehringer et al., "Novel Hinge-Binding Motifs for Janus Kinase 3 Inhibitors: A Comprehensive Structure-Activity Relationship Study on Tofacitinib Bioisosteres", ChemMedChem 2014, 9, 2516-2527.

Planken et al., "Discovery of N-((3R,4R)-4-Fluoro-1-(6-((3-methoxy-1-methyl-1H-pyrazol-4-yl)amino)-9-methyl-9H-burin-2-yl)pyrrolidine-3-acrylamide (PF-06747775) through Structure-Based Drug Design: A High Affinity Irreversible Inhibitor Targeting Oncogenic EGFR Mutants with Selectivity over Wild-Type EGFR", J. Med. Chem. 2017, 60, 3002-3019.

Kurup et al., "Design, synthesis and biological activity of N4-phenylsubstituted-7H-pyrrolo[2,3-d]pyrimidin-4-amines as dual inhibitors of aurora kinase A and epidermal growth factor receptor kinase", Journal of Enzyme Inhibition and Medicinal Chemistry 2017, 33, 74-84.

Zhang et al., Design, Synthesis, Biological Evaluation and X-ray Crystal Structure of Novel Classical 6,5,6-tricyclic Benzo[4,5]thieno[2,3-d]pyrimidines as Dual Thymidylate Synthase and Dihydrofolate Reductase Inhibitors. Bioorganic Medicinal Chemistry, 19, 3585-3594. (2011).

* cited by examiner a) isopropanol, catalytic conc HCl, reflux, 10h; b) SOCl₂, reflux, 2h; c) 84, NEt₃, DMF, room temperature, 8h.; d) PyBOP, HOBt, DIEA, DMF, room temperature, 8h a) 99, isopropanol, catalytic conc HCl, reflux, 10h a) Ph$_3$Cl,NaH, DMF, r.t.12 h, N$_2$; b) R$_4$-B(OH)$_2$,Pd(PPh$_3$)$_4$,K$_3$PO$_4$, DMF, μwave, 3 h; c)4-aminobenzanilide, isopropanol, conc HCl, reflux 3 h; d) CF$_3$COOH,THF a) SEM-Cl,NaH, DMF, r.t.12 h, N$_2$; b) R$_5$-NH$_2$,Pd$_2$(dba)$_3$,Cs$_2$CO$_3$, Xantphos, 1,4-dioxane,N$_2$, μwave, 140 °C, 45 minutes; c)4-aminobenzanilide, , isopropanol, conc HCl, reflux 3 h; d) CF$_3$COOH, CH$_2$Cl$_2$ a) K$_2$CO$_3$, R-Br, DMSO, N$_2$, 12 h, 25 °C; b) Y-B(OH)$_2$, K$_2$CO$_3$, Pd(dppf)$_2$Cl$_2$, N$_2$,1,4-dioxane, 4h, 100 °C; c)Cs$_2$CO$_3$, t-amyl alcohol, 100 °C, N$_2$, 20h

SUBSTITUTED PYRROLO[2,3-D]PYRIMIDINES AS INHIBITORS FOR MULTI-RESISTANT CANCERS

CROSS-REFERENCE TO RELATED APPLICATIONS

This application claims priority to U.S. Nonprovisional patent application Ser. No. 17/459,558 filed on Aug. 27, 2021, now U.S. Pat. No. 11,814,388, which claims priority to U.S. Provisional Pat. Appl. No. 63/071,446 filed on Aug. 28, 2020, the contents of which are hereby incorporated by reference in their entirety.

STATEMENT REGARDING FEDERALLY SPONSORED RESEARCH OR DEVELOPMENT

This invention was made by government support under grant number 1R15CA246256-01A1 awarded by the National Institutes of Health. The government has certain rights in the invention.

TECHNICAL FIELD

The present disclosure generally relates to inhibitors for multi-resistant cancers. The present disclosure also relates to methods of forming the compounds, methods for inhibiting aurora kinase A and/or aurora kinase B activity and epidermal growth factor activity, methods of treating, ameliorating, or preventing cancer, and use of the compounds for inhibiting aurora kinase A and/or aurora kinase B activity and epidermal growth factor activity.

BACKGROUND

The EGFR (epidermal growth factor receptor) inhibitors were among the first kinase inhibitors that were developed as targeted agents. Although approved for use in NSCLC (non-small cell lung cancer), the efficacy of this class of compounds is short-lived due to multiple mutations in the ATP (adenosine triphosphate) pocket and redundant signaling cascades. The first-generation EGFR inhibitors, erlotinib and gefitinib have decreased therapeutic responses in tumors expressing wild-type EGFR (wt EGFR) as compared to EGFR with a sensitizing mutation which includes an exon-19 deletion (del19) or leucine to arginine (L858R) mutation in the catalytic site. Resistance to erlotinib and gefitinib has developed due to a threonine to methionine mutation (T790M) mutation in the ATP pocket. Newer generations of EGFR inhibitors continue to suffer from a short-lived effectiveness against mutant EGFR-positive tumors (mEGFR+), reducing their utility in clinical practice.

A cysteine to serine (C797S) mutation dramatically reduces therapeutic response to afatinib and osimertinib. A combination of erlotinib and osimertinib has been used in tumors expressing the L858R/T790M/C797S triple mutation; however, therapeutic outcomes have been inconsistent and poor.

The KRAS (Kirsten rat sarcoma virus) protein is a GTPase signaling protein in the RAS/MAP/ERK signaling cascade downstream of EGFR that interplays with multiple signaling pathways and plays a role in proliferation, differentiation and survival. In KRAS expressing NSCLC, it is wt EGFR and not sensitized L858R EGFR that colocalizes with KRAS. As a result, EGFR inhibitors have poorer outcomes in KRAS expressing tumors.

Additionally, KRAS mutations render the protein constitutively active. Persistent signaling mediated through mutant KRAS (mKRAS) leads to the activation of multiple downstream effector pathways irrespective of EGFR inhibition. Thus, EGFR inhibitors that work upstream of KRAS are rendered ineffective in mEGFR+ and mKRAS+ NSCLC.

Newer therapeutic approaches that could address the resistance observed for EGFR inhibitors in mEGFR+ and mKRAS+ NSCLC are needed.

Aurora kinase (AURK) inhibitors have been studied in combination with EGFR inhibitors for mEGFR+ and mKRAS+ NSCLC. The mitosis-related aurora kinase A (AURKA) and aurora kinase B (AURKB) play a role in cell division and in pathways that drive tumorigenesis and metastasis. Erlotinib has demonstrated synergistic anticancer effects in combination with alisertib. It has also been shown that resistance to osimertinib was overcome if given in combination with alisertib in osimertinib-resistant NSCLC cells that were generated via osimertinib dose escalation. Osimertinib and alisertib were ineffective if given individually in the same cell lines. Mutant KRAS signaling in NSCLC was interrupted when erlotinib and ZM 447439 were utilized in combination.

Further, EGFR inhibitors used in combination with AURK inhibitors has been effective in mutant cancer cells derived from biopsy samples of lung cancer patients with disease progression on EGFR inhibitor therapy.

A Phase I study on the combination of erlotinib and alisertib was tolerated in NSCLC patients. A Phase II clinical trial is being planned to only include patients harboring KRAS mutations. A combination of erlotinib and barasertib also retards the development of the T790M EGFR mutation.

More recently, a Phase I/Ib study of alisertib in combination with osimertinib was initiated for metastatic EGFR-mutant positive lung cancer. Thus, the combination of AURK inhibitors with EGFR inhibitors has yielded promising results toward enhancing anticancer effects for EGFR inhibitors in NSCLC harboring mutant EGFR and mutant KRAS. Simultaneous inhibition of EGFR and AURK could provide an effective approach for circumventing resistance to EGFR inhibitors in NSCLC and improving therapeutic outcomes.

Dual-targeted EGFR/AURK inhibitors could provide advantages over a combination of single EGFR and single AURK inhibitors. Multi-targeted kinase inhibitors have shown several advantages over single kinase inhibitors by allowing for more predictable pharmacokinetics, reduced cost of therapy and improved patient compliance while maintaining the benefits of reduced incidence of resistance and enhanced anticancer effects.

Despite their promise, small molecule dual-targeted EGFR/AURK inhibitors are largely unexplored and the effectiveness of dual-targeted EGFR/AURK inhibitors against NSCLC is unknown.

Accordingly, it is desirable to provide compounds and methods for inhibiting aurora kinase A and/or aurora kinase B activity and epidermal growth factor activity. Furthermore, other desirable features and characteristics will become apparent from the subsequent summary and detailed description and the appended claims, taken in conjunction with the foregoing technical field and background.

BRIEF SUMMARY OF THE INVENTION

A compound of Formula (I-2) or pharmaceutically acceptable salts thereof, is provided herein, as follows:

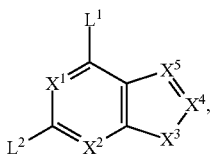

(I-2)

or a pharmaceutically acceptable salt thereof;
wherein:
$X^1$ is N;
$X^2$ is N;
$X^3$ is NH;
$X^4$ is N or $CR^2$;
  wherein $R^2$ is H, COOH, a 5-membered heteroaryl, or $X^6R3$;
    wherein the 5-membered heteroaryl contains 1 N heteroatom and 1 additional heteroatom selected from the group consisting of N, O, and S; wherein the 5-membered heteroaryl is optionally substituted with 1, 2, or 3 substituents independently selected from the group consisting of halo, CN, $NO_2$, $C_{1-6}$ alkyl, $C_{1-6}$ haloalkyl, $CH_2$-phenyl, $NH_2$, $NHC_{1-10}$ alkyl, $N(C_{1-10}$ alkyl$)_2$, OH, $OC_{1-6}$ alkyl, $OC_{1-6}$ haloalkyl, $C_{3-6}$ cycloalkyl, and phenyl;
    wherein $X^6$ is $CONH(CH)_m$, $NHCO(CH)_m$, $CH_2CH_2$, C=C, C≡C, $CH_2$, S, $NH(CH)_m$, or COO;
    wherein $R^3$ is a 5-membered heteroaryl, 6-membered heteroaryl, or substituted phenyl;
      wherein the 5-membered or 6-membered heteroaryl contains 1 N heteroatom and 1-3 additional heteroatoms selected from the group consisting of N, O, and S, and is optionally substituted with 1, 2, or 3 substituents independently selected from the group consisting of halo, $C_{1-6}$ alkyl, $C_{1-6}$ haloalkyl, $C_{1-6}$ alkylamino, $C_{1-6}$ cycloalkylamino, $NH_2$, $NHC_{1-10}$ alkyl, $NHC_{1-10}$ aryl, $NHC_{1-10}$ alkenyl, NHCOalkenyl($C_{1-6}$alkyl)N($C_{1-10}$alkyl$)_2$, $NHC_{1-10}$ alkynyl N($C_{1-10}$ alkyl$)_2$, OH, COOH, $CH_2COOH$, $OC_{1-6}$ alkyl, $OC_{1-6}$ haloalkyl, $C_{3-6}$ cycloalkyl, and phenyl, $CONHC_{1-10}$, CONHalkyl, CONH($C_{1-10}$ alkyl$)_2$, CONHalkenyl, $CH_2$CONHalkenyl, $CONHC_{1-6}$ cycloalkyl, $CONHC_{1-10}$, $CONHC_{3-6}$ cycloalkylamine, $CONHC_{3-6}$ aminophenyl, $CONHC_{1-6}$ heteroarylamine, $CONHC_{1-6}$ alkylcarboxylate, $CONHC_{1-6}$ cycloalkylcarboxylate, $CONHC_{1-6}$ heteroarylcarboxylate, $CONHC_{1-6}$ phenylcarboxylate, $NHCOC_{1-10}$ NHCOalkyl, NHCO($C_{1-10}$ alkyl$)_2$, NHCOalkenyl, $CH_2$NHCOalkenyl, $NHCOC_{1-6}$ cycloalkyl, $NHCOC_{1-10}$, $NHCOC_{3-10}$ cycloalkylamine, $NHCOC_{1-10}$ aminophenyl, $NHCOC_{1-6}$ heteroarylamine, $NHCOC_{1-6}$ alkylcarboxylate, $NHCOC_{1-6}$ cycloalkylcarboxylate, $NHCOC_{1-6}$ heteroarylcarboxylate;
      wherein the heteroaryl is a pyrimidine, a pyridine, a pyrazole, an isoxazole, or a tetrazole;
      wherein the cycloalkylamine is an aminopyrrolidine, an aminopiperidine, or an aminopiperazine;
      wherein the substituted phenyl is optionally substituted with 1, 2, or 3 substituents independently selected from the group consisting of halo, $C_{1-6}$ alkyl, $C_{1-6}$ haloalkyl, $C_{1-6}$ alkylamino, $C_{1-6}$ cycloalkylamino, $NH_2$, $NHC_{1-10}$ alkyl, $NHC_{1-10}$ aryl, $NHC_{1-10}$ alkenyl, NHCOalkenyl($C_{1-6}$alkyl)N($C_{1-10}$alkyl$)_2$, $NHC_{1-10}$ alkynyl N($C_{1-10}$ alkyl$)_2$, OH, COOH, $CH_2COOH$, $OC_{1-6}$ alkyl, $OC_{1-6}$ haloalkyl, $C_{3-6}$ cycloalkyl, and phenyl, $CONHC_{1-10}$, CONHalkyl, CONH($C_{1-10}$ alkyl$)_2$, CONHalkenyl, $CH_2$CONHalkenyl, $CONHC_{1-6}$ cycloalkyl, $CONHC_{1-10}$, $CONHC_{3-6}$ cycloalkylamine, $CONHC_{3-6}$ aminophenyl, $CONHC_{1-6}$ heteroarylamine, $CONHC_{1-6}$ alkylcarboxylate, $CONHC_{1-6}$ cycloalkylcarboxylate, $CONHC_{1-6}$ heteroarylcarboxylate, $CONHC_{1-6}$ phenylcarboxylate, $NHCOC_{1-10}$ NHCOalkyl, NHCO($C_{1-10}$ alkyl$)_2$, NHCOalkenyl, $CH_2$NHCOalkenyl, $NHCOC_{1-6}$ cycloalkyl, $NHCOC_{1-10}$, $NHCOC_{1-10}$ cycloalkylamine, $NHCOC_{1-10}$ aminophenyl, $NHCOC_{1-6}$ heteroarylamine, $NHCOC_{1-6}$ alkylcarboxylate, $NHCOC_{1-6}$ cycloalkylcarboxylate, $NHCOC_{1-6}$ heteroarylcarboxylate;
$X^5$ is CH, C($CH_3$), CCOOH, or $CX^7R^8$;
wherein $X^7$ is C, C—CONH(CH)$_m$, C—NHCO(CH)$_m$, C—$CH_2CH_2$, C—C≡C, C—C≡C, C—$CH_2$, C—S, C—NH(CH)$_m$, C—O, C—COO; and
wherein $R^8$ is a 5-membered heteroaryl, a 6-membered heteroaryl, or substituted phenyl;
  wherein the 5-membered or 6-membered heteroaryl contains 1 N heteroatom and 1-3 additional heteroatom selected from the group consisting of N, O, and S, and is optionally substituted with 1, 2, or 3 substituents independently selected from the group consisting of halo, $C_{1-6}$ alkyl, $C_{1-6}$ haloalkyl, $C_{1-6}$ alkylamino, $C_{1-6}$ cycloalkylamino, $NH_2$, $NHC_{1-10}$ alkyl, $NHC_{1-10}$ aryl, $NHC_{1-10}$ alkenyl, NHCOalkenyl($C_{1-6}$alkyl)N($C_{1-10}$alkyl$)_2$, $NHC_{1-10}$ alkynyl N($C_{1-10}$ alkyl$)_2$, OH, COOH, $CH_2COOH$, $OC_{1-6}$ alkyl, $OC_{1-6}$ haloalkyl, $C_{3-6}$ cycloalkyl, and phenyl, $CONHC_{1-10}$, CONHalkyl, CONH($C_{1-10}$ alkyl$)_2$, CONHalkenyl, $CH_2$CONHalkenyl, $CONHC_{1-6}$ cycloalkyl, $CONHC_{1-10}$, $CONHC_{3-6}$ cycloalkylamine, $CONHC_{3-6}$ aminophenyl, $CONHC_{1-6}$ heteroarylamine, $CONHC_{1-6}$ alkylcarboxylate, $CONHC_{1-6}$ cycloalkylcarboxylate, $CONHC_{1-6}$ heteroarylcarboxylate, $CONHC_{1-6}$ phenylcarboxylate, $NHCOC_{1-10}$ NHCOalkyl, NHCO($C_{1-10}$ alkyl$)_2$, NHCOalkenyl, $CH_2$NHCOalkenyl, $NHCOC_{1-6}$ cycloalkyl, $NHCOC_{1-10}$, $NHCOC_{1-10}$ cycloalkylamine, $NHCOC_{1-10}$ aminophenyl, $NHCOC_{1-6}$ heteroarylamine, $NHCOC_{1-6}$ alkylcarboxylate, $NHCOC_{1-6}$ cycloalkylcarboxylate, $NHCOC_{1-6}$ heteroarylcarboxylate;
  wherein the heteroaryl is a pyrimidine, a pyridine, a pyrazole, an isoxazole, or a tetrazole;
  wherein the cycloalkylamine is an aminopyrrolidine, an aminopiperidine, or an aminopiperazine;
  wherein the substituted phenyl is optionally substituted with 1, 2, or 3 substituents independently selected from the group consisting of halo, $C_{1-6}$ alkyl, $C_{1-6}$ haloalkyl, $C_{1-6}$ alkylamino, $C_{1-6}$ cycloalkylamino, $NH_2$, $NHC_{1-10}$ alkyl, $NHC_{1-10}$ aryl, $NHC_{1-10}$ alkenyl, NHCOalkenyl($C_{1-6}$alkyl)N($C_{1-10}$alkyl$)_2$, $NHC_{1-10}$ alkynyl N($C_{1-10}$ alkyl$)_2$, OH, COOH, $CH_2COOH$, $OC_{1-6}$ alkyl, $OC_{1-6}$ haloalkyl, C₃₋₆ cycloalkyl, and phenyl, CONH-C₁₋₁₀, CONHalkyl, CONH(C₁₋₁₀ alkyl)₂, CONHalkenyl, CH₂CONHalkenyl, CONHC₁₋₆ cycloalkyl, CONHC₁₋₁₀, CONHC₃₋₆ cycloalkylamine, CONHC₃₋₆ aminophenyl, CONHC₁₋₆ heteroarylamine, CONHC₁₋₆ alkylcarboxylate, CONHC₁₋₆ cycloalkylcarboxylate, CONHC₁₋₆ heteroarylcarboxylate, CONHC₁₋₆ phenylcarboxylate, NHCOC₁₋₁₀ NHCOalkyl, NHCO(C₁₋₁₀ alkyl)₂, NHCOalkenyl, CH₂NHCOalkenyl, NHCOC₁₋₆ cycloalkyl, NHCOC₁₋₁₀, NHCOC₁₋₁₀ cycloalkylamine, NHCOC₁₋₁₀ aminophenyl, NHCOC₁₋₆ heteroarylamine, NHCOC₁₋₆ alkylcarboxylate, NHCOC₁₋₆ cycloalkylcarboxylate, NHCOC₁₋₆ heteroarylcarboxylate;

L¹ is —NR⁴—R¹;

R⁴ is H; and

R¹ is:

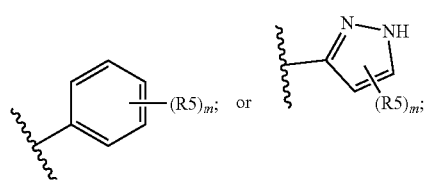

wherein:

(i) each R⁵ is independently Br, F, COOH, CH₂COOH, NHCOalkenyl, NHCOalkenyl(C₁₋₆ alkyl)N(C₁₋₁₀alkyl)₂, CH₂CONHalkenyl, CH₂NHCOalkenyl CH₂-phenyl, C₃₋₆ alkylamine, C₃₋₆ cycloalkylamine, C₃₋₆ alkylcarboxylate, C₃₋₆ cycloalkylcarboxylate or phenyl; or (ii) each R⁵ is independently:

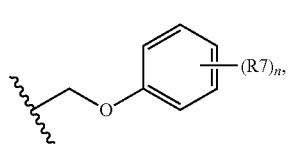

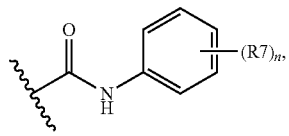

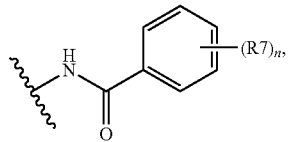

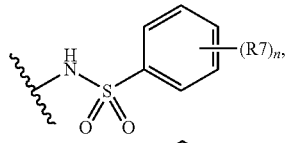

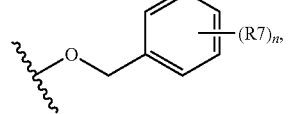

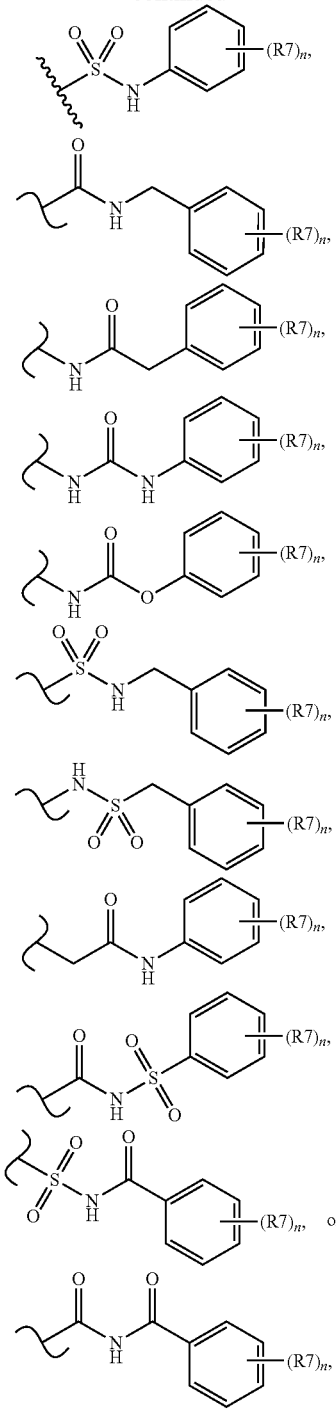

each R7 is independently H, halo, CN, NO₂, C₁₋₁₀ alkyl, C₁₋₁₀ haloalkyl, C₂₋₁₀ alkenyl, C₂₋₁₀ alkynyl, C(O)C₁₋₆ alkyl, C(O)NHC₁₋₆ alkyl, NH₂, NHC₁₋₁₀ alkyl, N(C₁₋₁₀ alkyl)₂, NHCOalkenyl, NHC(O)C₁₋₆ alkyl, NHC(O)C₁₋₆ alkenyl, NHCOalkenyl(C₁₋₆alkyl)N(C₁₋₁₀alkyl)₂, NHS(O)₂C₁₋₁₀ alkyl, OH, OC₁₋₁₀ alkyl, OC₁₋₁₀ haloalkyl, SH, SC₁₋₁₀ alkyl, S(O)C₁₋₆ alkyl, S(O)₂NHC₁₋₆ alkyl, C₃₋₁₀ cycloalkyl, C₄₋₁₀ cycloalkenyl, a monocyclic 3- to 8-membered ring, or a bicyclic 6- to 12-membered ring;

wherein each monocyclic 3- to 8-membered ring or bicyclic 6- to 12-membered ring is fully saturated, partially unsaturated, or fully unsaturated;

wherein each monocyclic 3- to 8-membered ring independently contains carbon atoms and optionally and independently contains 1, 2, or 3 heteroatoms independently selected from the group consisting of N, O, and S;

wherein each bicyclic 6- to 12-membered ring independently contains carbon atoms and optionally and independently contains 1, 2, 3, 4, 5, or 6 heteroatoms independently selected from the group consisting of N, O, and S;

wherein each $C_{1-10}$ alkyl, $C_{2-10}$ alkenyl, $C_{2-10}$ alkynyl, $NHC_{1-10}$ alkyl, $N(C_{1-10}$ alkyl$)_2$, $OC_{1-10}$ alkyl, and $SC_{1-10}$ alkyl is optionally and independently substituted with 1, 2, 3, 4, or 5 substituents independently selected from the group consisting of halo, CN, $NO_2$, $CH_2$-phenyl, $NH_2$, $NHC_{1-10}$ alkyl, $N(C_{1-10}$ alkyl$)_2$, OH, $OC_{1-6}$alkyl, $OC_{1-10}$ haloalkyl, =O, $C_{3-6}$ cycloalkyl, phenyl, and a multicyclic ring system;

wherein each $C_{3-10}$cycloalkyl, $C_{4-10}$ cycloalkenyl, monocyclic 3- to 8-membered ring, or bicyclic 6- to 12-membered ring is optionally and independently substituted with 1, 2, 3, 4, or 5 substituents independently selected from the group consisting of halo, CN, $NO_2$, $CH_2$-phenyl, $NH_2$, $NHC_{1-10}$alkyl, $N(C_{1-10}$ alkyl$)_2$, OH, $OC_{1-6}$alkyl, $OC_{1-10}$haloalkyl, =O, $C_{3-6}$ cycloalkyl, phenyl, and a multicyclic ring system; and wherein each multicyclic ring system contains at least one nonaromatic ring and at least one aromatic ring; or wherein each multicyclic ring system contains at least one heteroaromatic ring;

wherein each m is independently 1, 2, 3, 4, or 5;

wherein each n is independently 1, 2, 3, 4, or 5; and $L^2$ is H or $NH_2$.

DETAILED DESCRIPTION

Figure 1A:
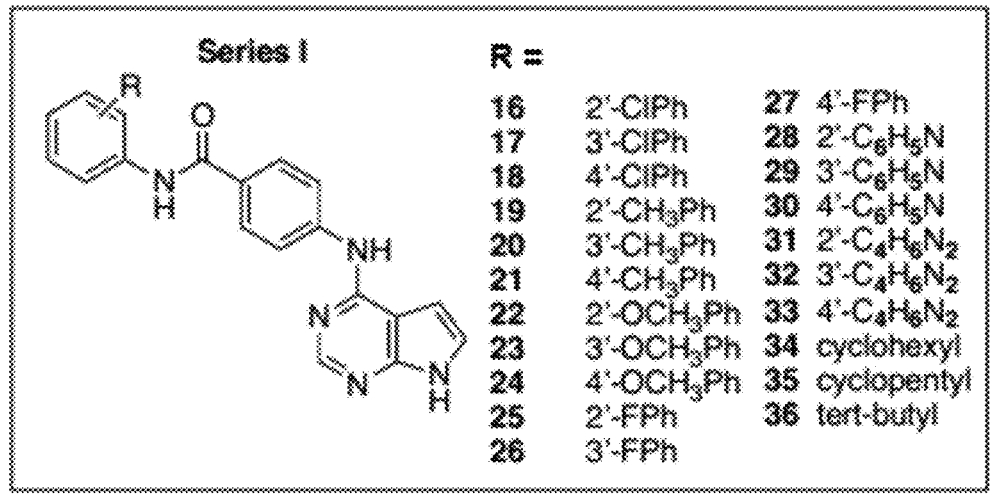
FIGS. 1A-1G are representations of chemical structures illustrating non-limiting embodiments of a compound.
Figure 1B:
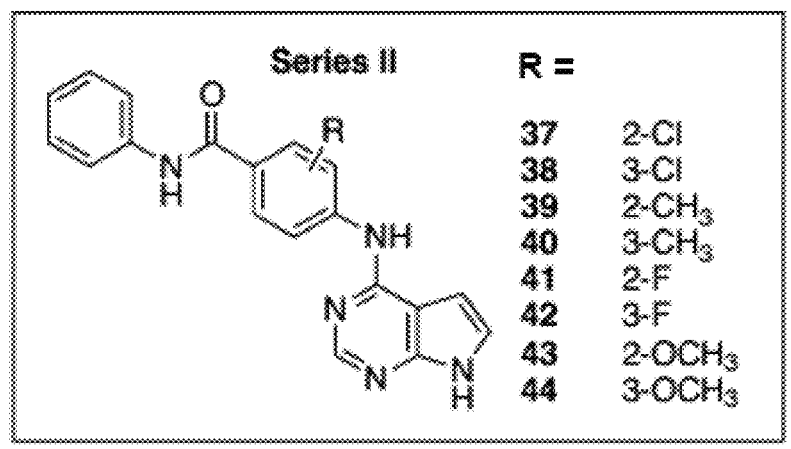
Figure 1C:
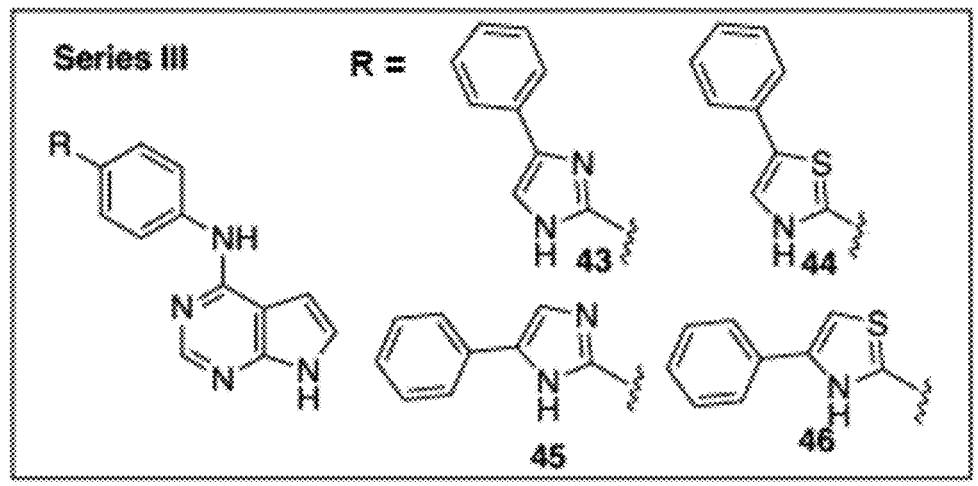
Figure 1D:
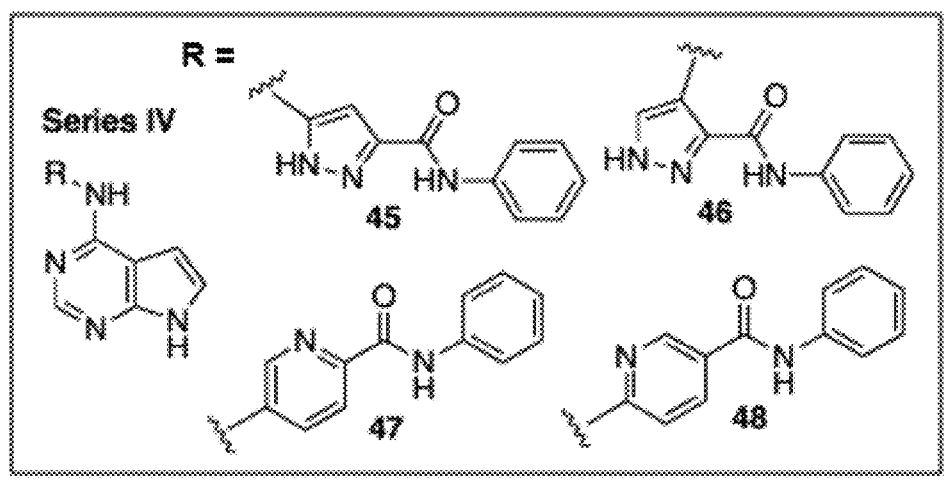
Figure 1E:
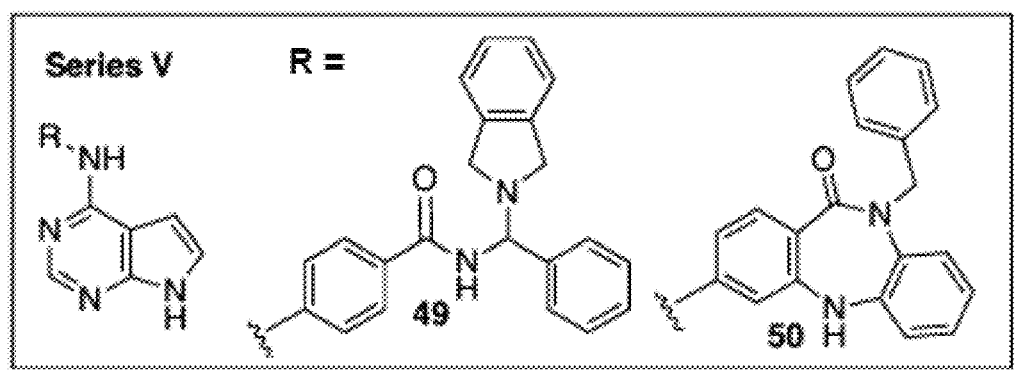
Figure 1F:
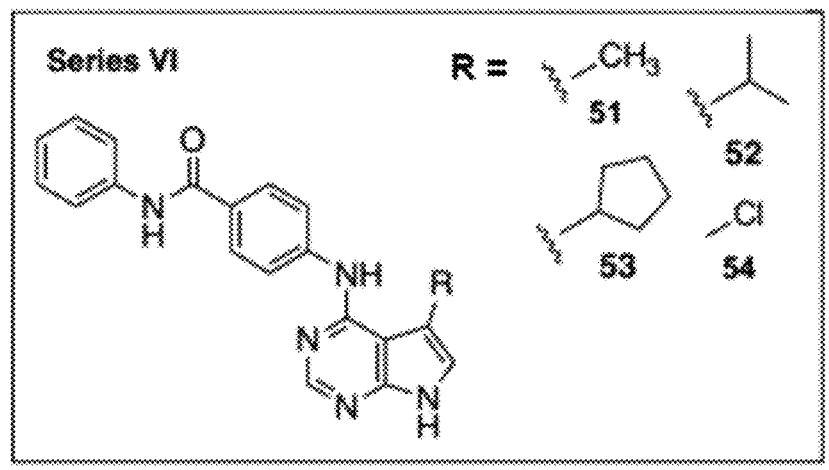
Figure 1G:
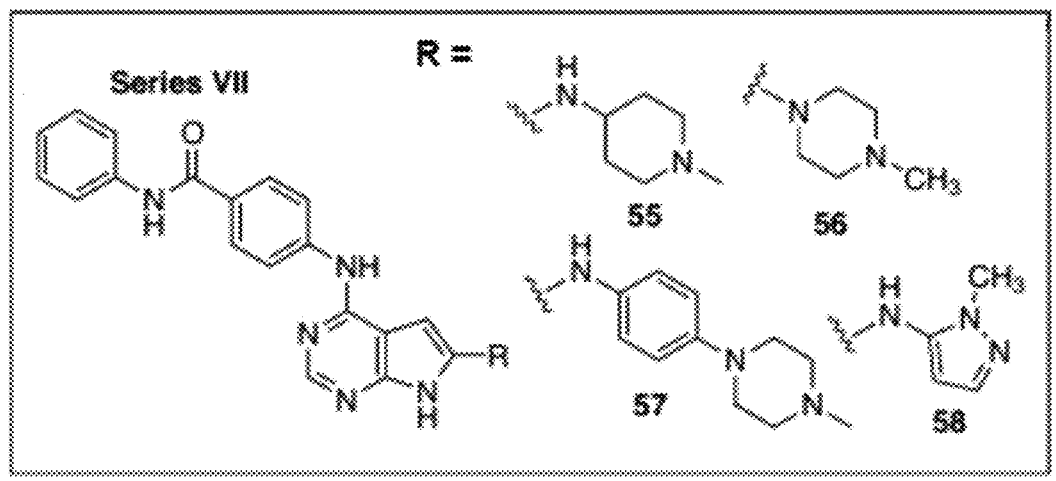
Figure 2A:
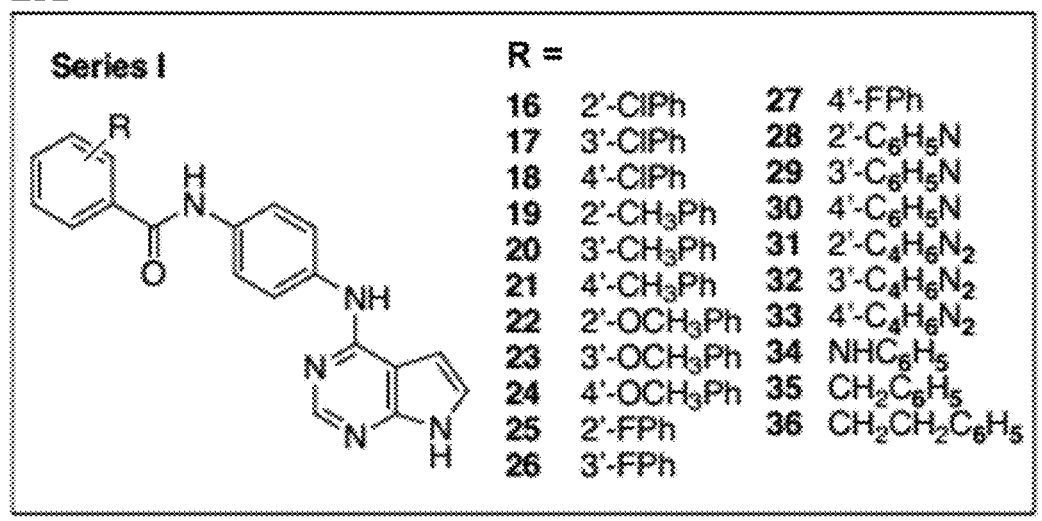
FIGS. 2A-2F are representations of chemical structures illustrating other non-limiting embodiments of the compound.
Figure 2B:
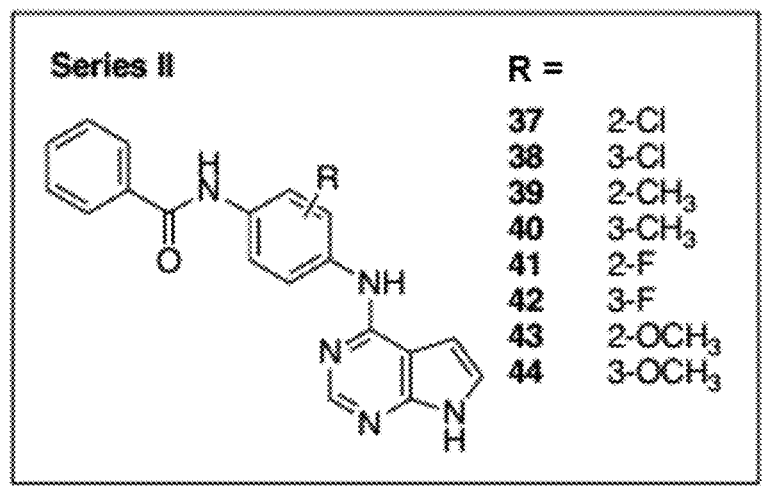
Figure 2C:
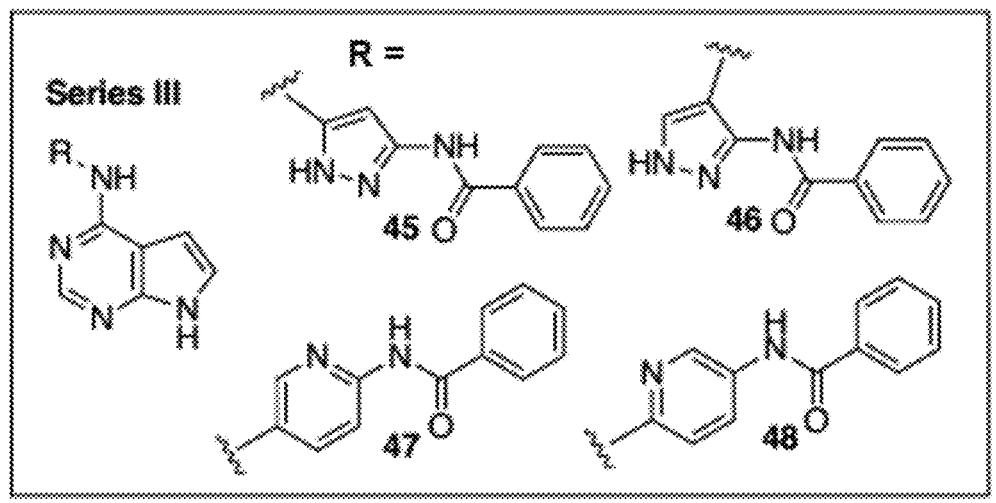
Figure 2D:
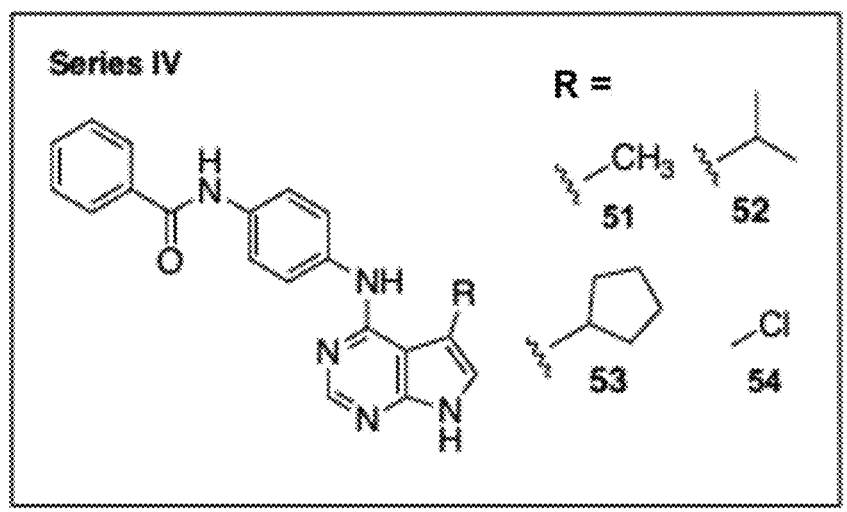
Figure 2E:
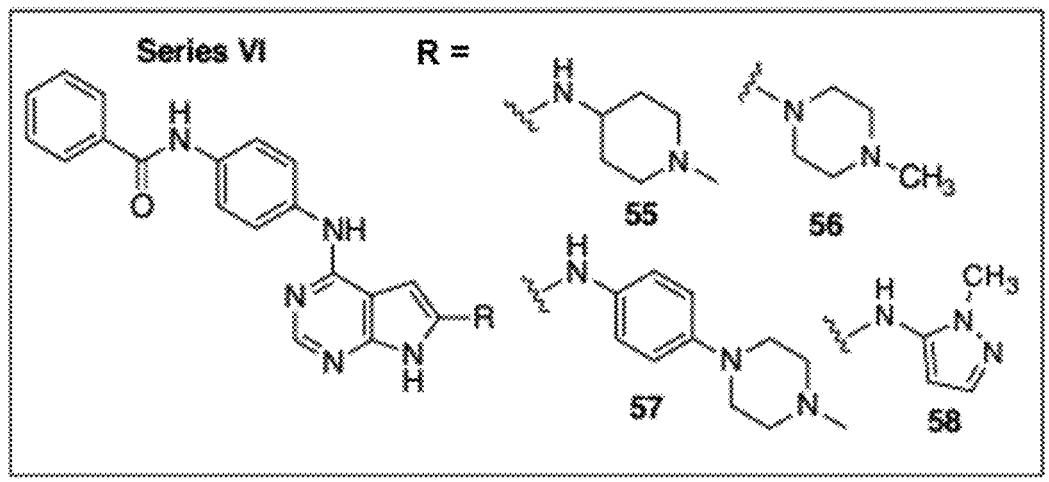
Figure 2F:
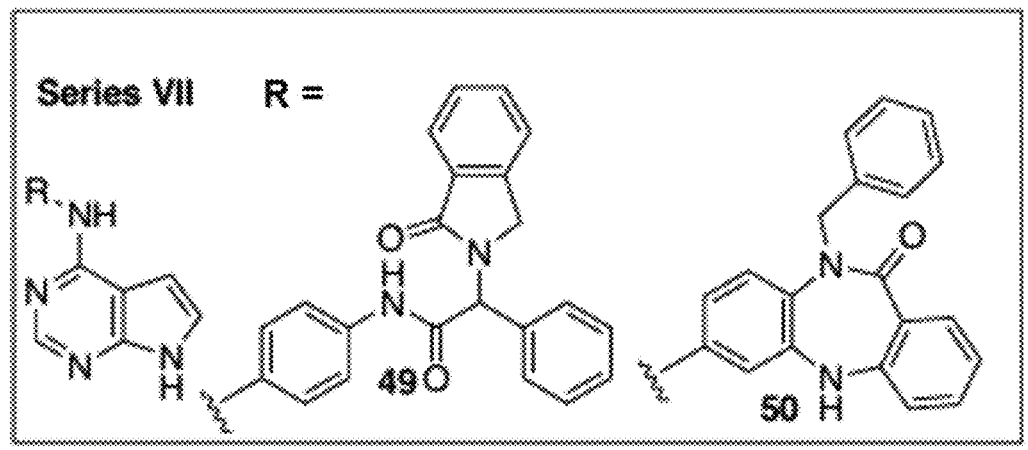
Figure 3A:
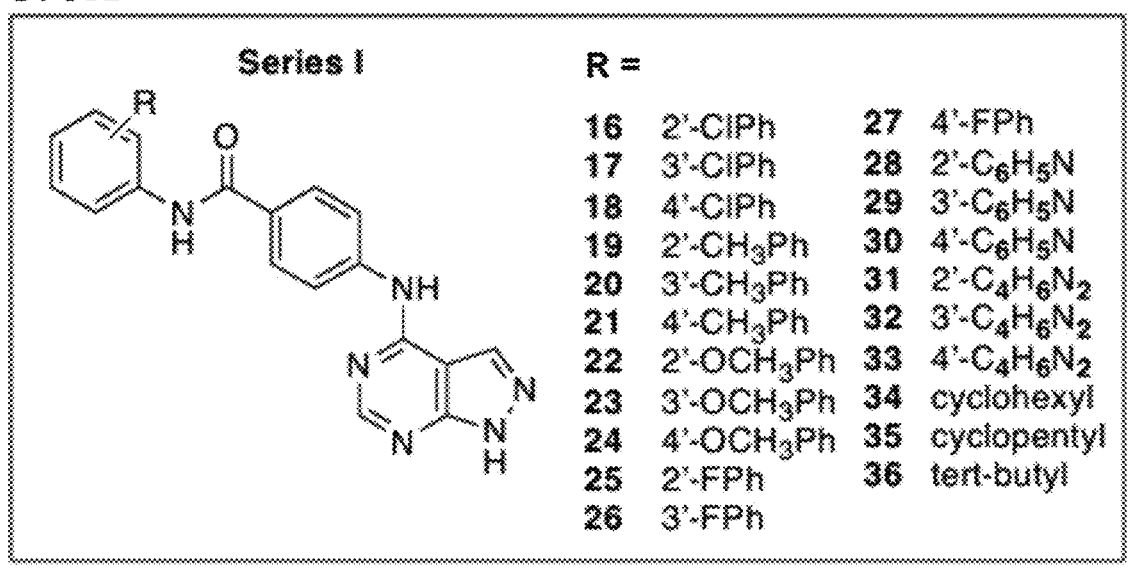
FIGS. 3A-3D are representations of chemical structures illustrating other non-limiting embodiments of the compound.
Figure 3B:
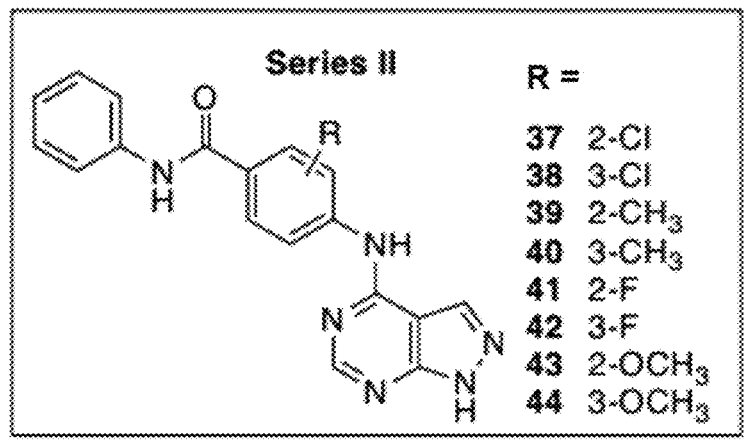
Figure 3C:
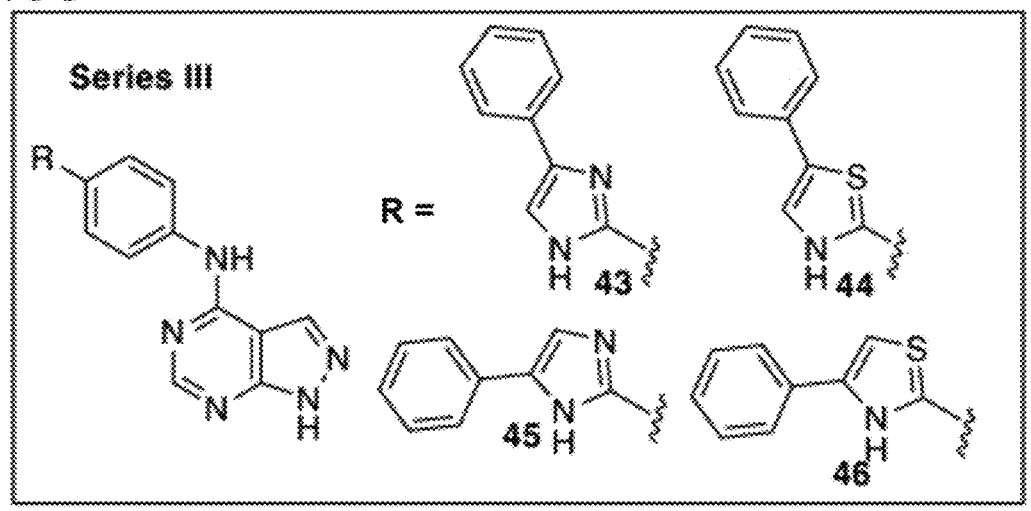
Figure 3D:
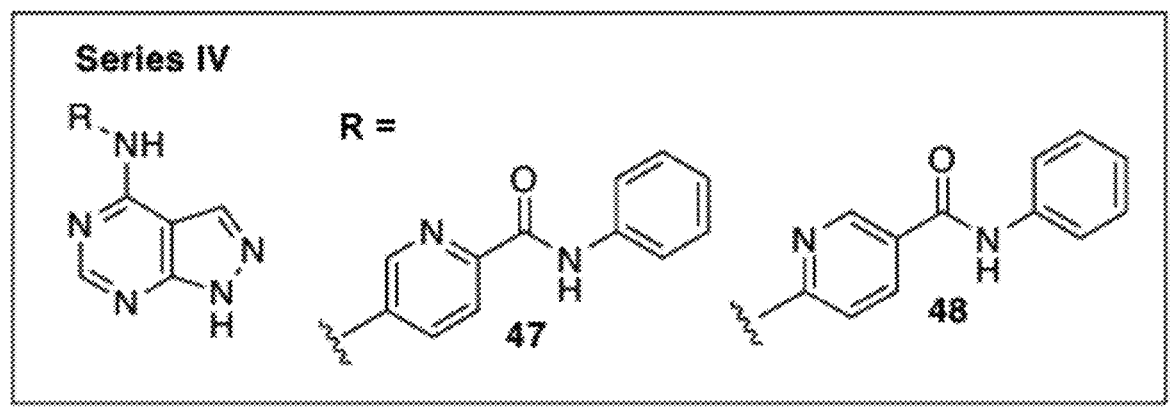
Figure 3E:
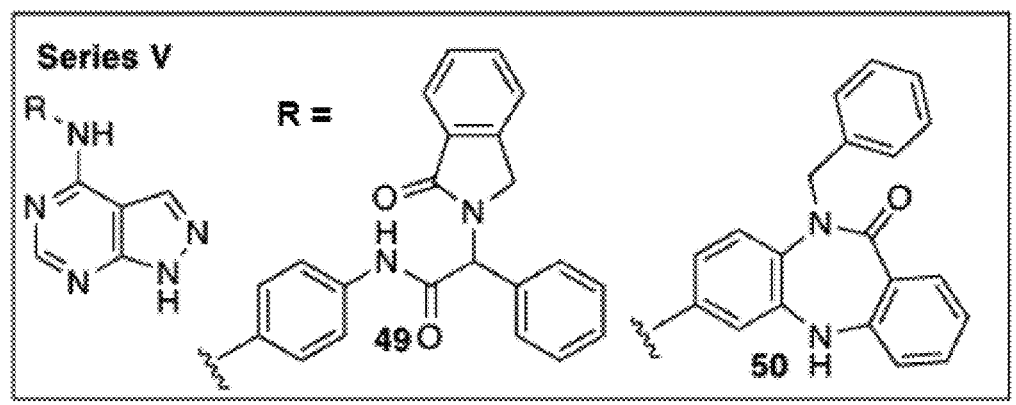
FIGS. 3E-3H are representations of chemical structures illustrating other non-limiting embodiments of the compound.
Figure 3F:
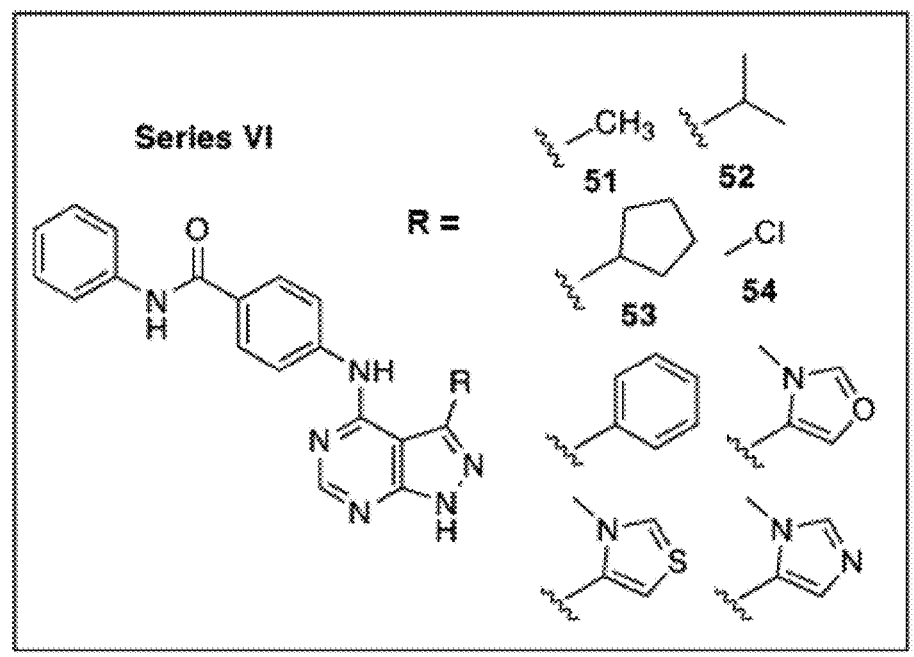
Figure 3G:
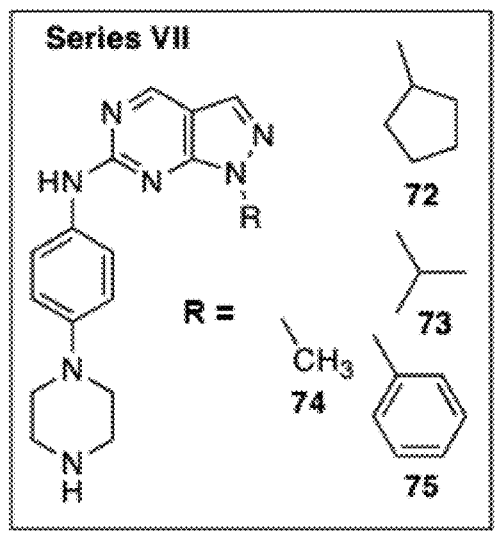
Figure 3H:
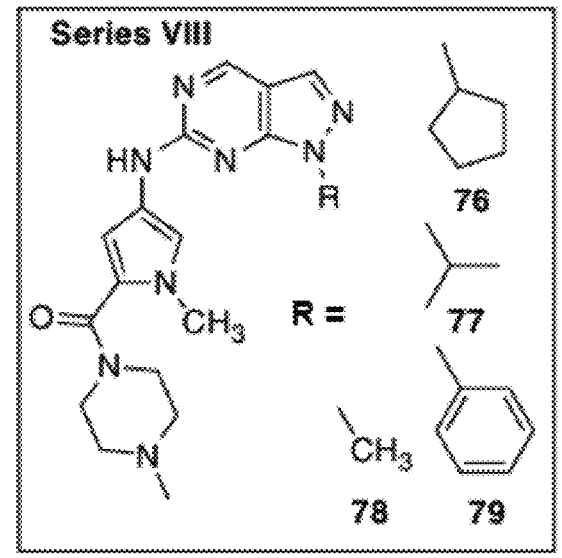
Figure 4A:
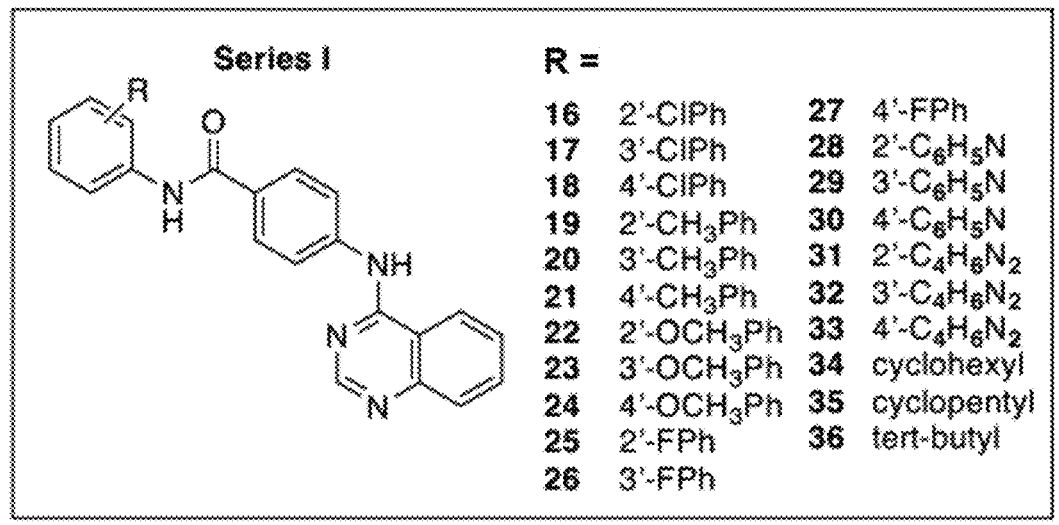
FIGS. 4A-4C are representations of chemical structures illustrating other non-limiting embodiments of the compound.
Figure 4B:
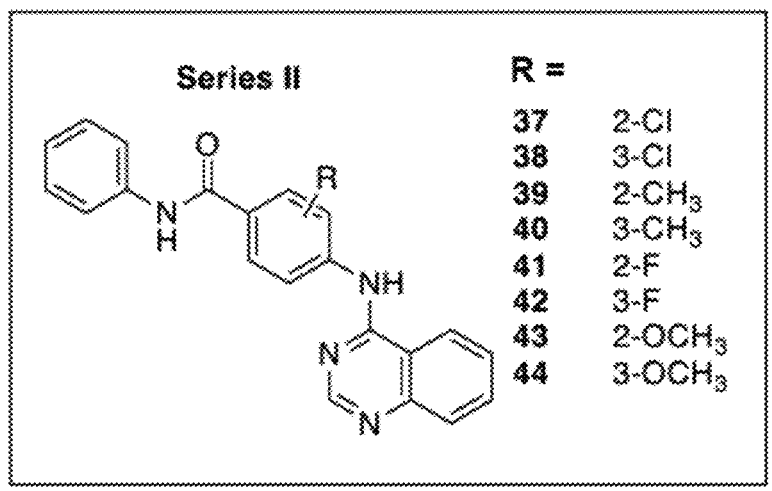
Figure 4C:
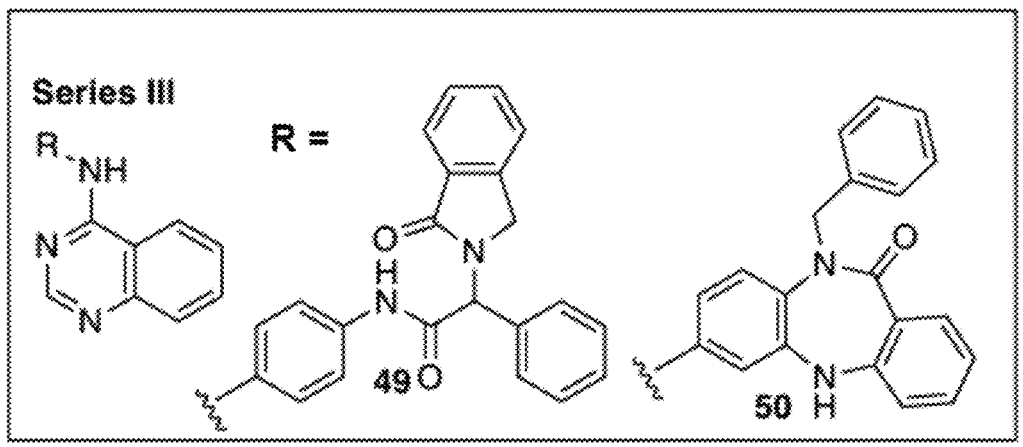
Figure 4D:
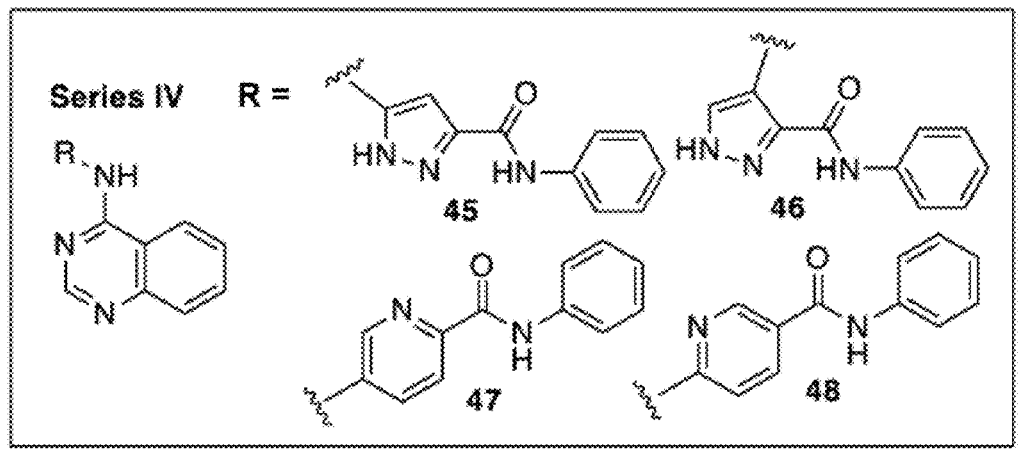
FIGS. 4D-4F are representations of chemical structures illustrating other non-limiting embodiments of the compound.
Figure 4E:
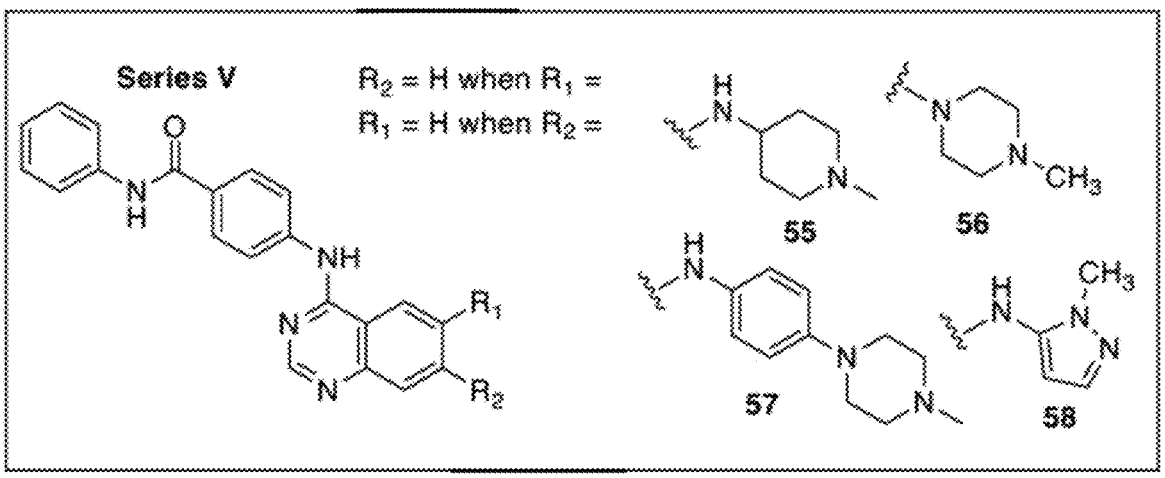
Figure 4F:
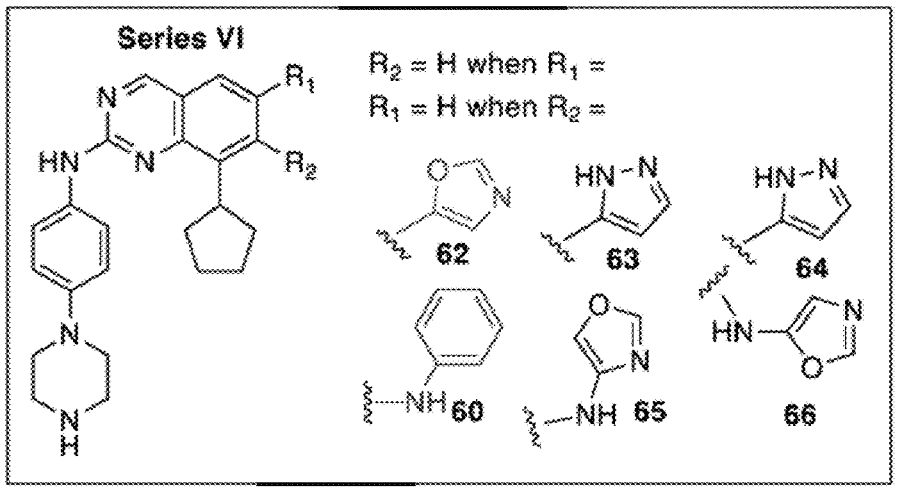
Figure 5A:
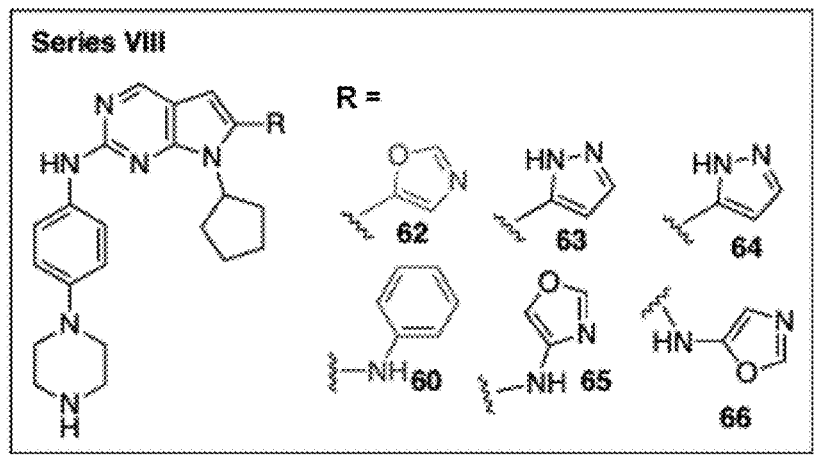
FIGS. 5A-5E are representations of chemical structures illustrating other non-limiting embodiments of the compound.
Figure 5B:
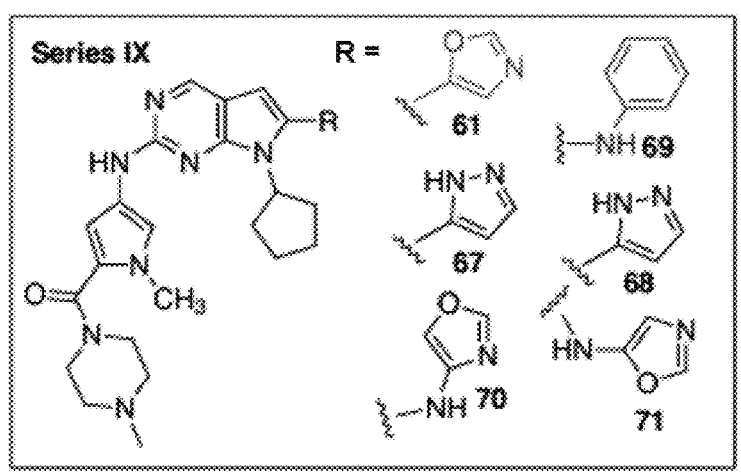
Figure 5C:
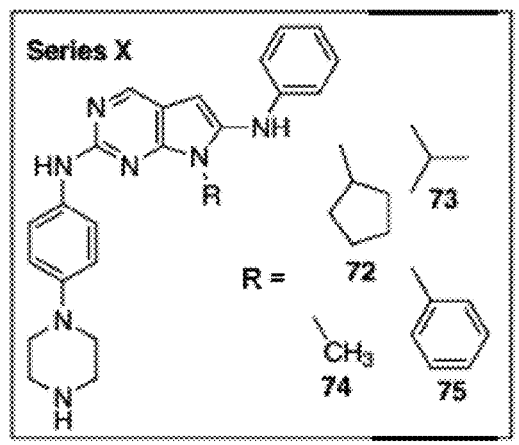
Figure 5D:
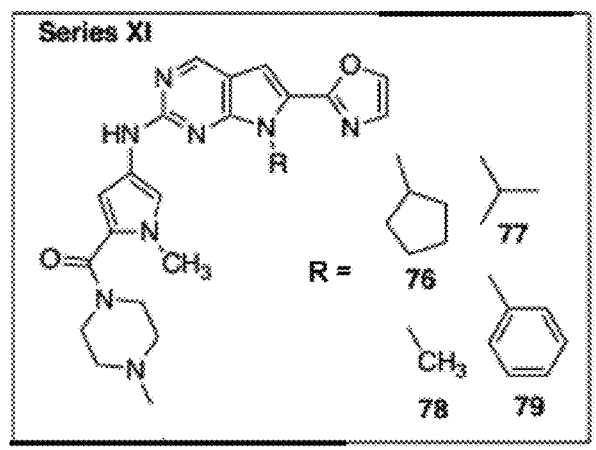
Figure 5E:
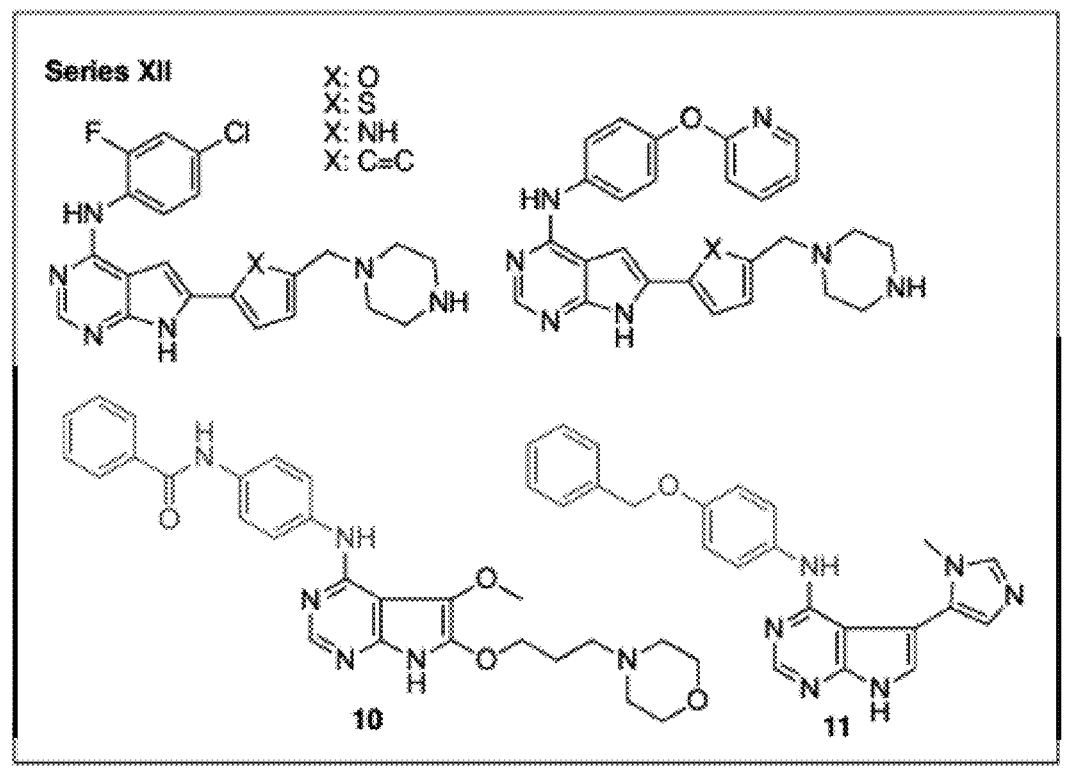

Except in the examples, or where otherwise expressly indicated, all numerical quantities in this description indicating amounts of material or conditions of reaction and/or use are to be understood as modified by the word "about" in describing the broadest scope of the disclosure. In various embodiments, the terms "about" and "approximately", when referring to a specified, measurable value (such as a parameter, an amount, a temporal duration, and the like), is meant to encompass the specified value and variations of and from the specified value, such as variations of +/−10% or less, alternatively+/−5% or less, alternatively+/−1% or less, alternatively +/−0.1% or less of and from the specified value, insofar as such variations are appropriate to perform in the disclosed embodiments. Thus the value to which the modifier "about" or "approximately" refers is itself also specifically disclosed.

Practice within the numerical limits stated is generally preferred. Also, unless expressly stated to the contrary: percent, "parts of," and ratio values are by weight; the description of a group or class of materials as suitable or preferred for a given purpose in connection with the invention implies that mixtures of any two or more of the members of the group or class are equally suitable or preferred; description of constituents in chemical terms refers to the constituents at the time of addition to any combination specified in the description, and does not necessarily preclude chemical interactions among the constituents of a mixture once mixed; the first definition of an acronym or other abbreviation applies to all subsequent uses herein of the same abbreviation and applies mutatis mutandis to normal grammatical variations of the initially defined abbreviation; and, unless expressly stated to the contrary, measurement of a property is determined by the same technique as previously or later referenced for the same property.

It must also be noted that, as used in the specification and the appended claims, the singular form "a," "an," and "the" comprise plural referents unless the context clearly indicates otherwise. For example, reference to a component in the singular is intended to comprise a plurality of components.

As used herein, an "embodiment" means that a particular feature, structure or characteristic is included in at least one or more manifestations, examples, or implementations of this invention. Furthermore, the particular features, structures or characteristics may be combined in any suitable manner, as would be apparent to a person skilled in the art.

Combinations of features of different embodiments are all meant to be within the scope of the invention, without the need for explicitly describing every possible permutation by example.

Thus, any of the claimed embodiments can be used in any combination.

As used herein, the term "weight percent" (and thus the associated abbreviation "wt. %") typically refers to a percent by weight expressed in terms of a weight of dry matter. As such, it is to be appreciated that a wt. % can be calculated on a basis of a total weight of a composition, or calculated from a ratio between two or more components/parts of a mixture (e.g. a total weight of dry matter).

Throughout this disclosure, where publications are referenced, the disclosures of these publications in their entireties are hereby incorporated by reference into this disclosure to more fully describe the state of the art to which this disclosure pertains.

The following detailed description is merely exemplary in nature and is not intended to limit the invention or the application and uses of the invention. Furthermore, there is no intention to be bound by any theory presented in the preceding background or the following detailed description.

In certain embodiments, compounds useful for treating, ameliorating, or preventing disorders relating to at least one of aurora kinase A (AURKA), aurora kinase B (AURKB), and epidermal growth factor (EGFR) are provided herein. In these and other embodiments, a method for inhibiting AURK A and/or AURK B activity and EGFR activity is provided herein. Further, a method of treating, ameliorating, or preventing cancer is also provided herein.

In various embodiments, the compounds provided herein are useful for treating, ameliorating, or preventing disorders, such as cancers, that are EGFR positive. The disorders, such as cancers, may exhibit over expression of wild-type EGFR, activated L858R, or del19 EGFR. It is believed that the compounds described herein are effective for inhibiting both AURK B activity and EGFR activity. Non-limiting examples of disorders suitable for treatment with the compounds described herein include, but are not limited to, lung cancer, prostate cancer, breast cancer, colon cancer, rectum cancer, head cancer, neck cancer, esophagogastric cancer, liver cancer, glioblastoma, cervical cancer, ovarian cancer, bladder cancer, kidney cancer, pancreatic cancer, or combinations thereof.

Compounds and Related Methods:

The present disclosure provides a compound. In certain embodiments, the method includes administering an effective amount of a compound of Formula (I) or a pharmaceutically acceptable salt thereof,

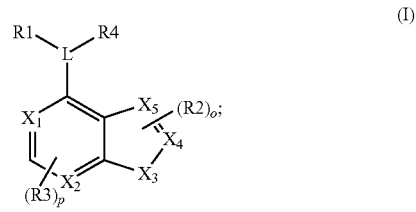

an effective amount of compound of Formula (II) or a pharmaceutically acceptable salt thereof,

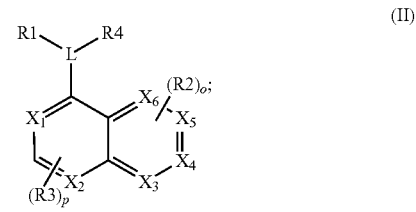

an effective amount of compound of Formula (III) or a pharmaceutically acceptable salt thereof,

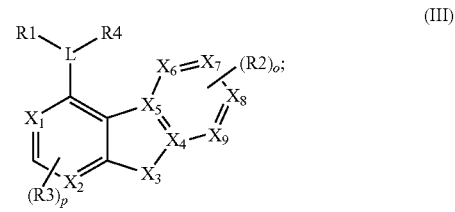

or combinations thereof;
wherein,
L is CH, N, O, or S;
each of $X_3$, $X_4$, $X_5$, $X_6$, $X_7$, $X_8$, and $X_9$, independently, is CR2, N, NR2, O, or S;
each of $X_1$ and $X_2$, independently, is CR3, or N;
each of R1, R2, R3, and R4, independently, is H, halo, alkylamino, arylamino, heteroalkylamino, heteroarylamino, alkylthio, arylthio, heteroalkylthio, heteroarylthio, heteroalkyloxy, heteroaryloxy, alkoxy, aryloxy, haloalkyl, haloalkoxyl, oxo, CN, OH, SH, $NO_2$, $NH_2$, acetyl, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl, $C(O)C_{1-6}$-alkyl, —NH-aryl-C(O)NH$C_{1-6}$-alkyl, —NH-heteroaryl-C(O)NH$C_{1-6}$-alkyl, —NH-alkyl-C(O)NH$C_{1-6}$-alkyl, —NH-aryl-C(O)NH$C_{1-6}$-aryl, —NH-aryl-C(O)NH$C_{1-6}$-heteroaryl, —NH-aryl-C(O)NH$C_{1-6}$-heteroalkyl, —NH-arylNHC(O)$C_{1-6}$-alkyl, —NH-alkyl, —NH-aryl, —NH-heteroaryl, —NH-haloaryl, —NH— haloheteroaryl, —NH-aryl-S(O)$C_{1-6}$-alkyl, —NH-aryl-S(O)$_2$NH$C_{1-6}$-alkyl, —NH-alkyl-S(O)$_2$NH$C_{1-6}$-alkyl, —NH-heteroaryl-S(O)$_2$NH$C_{1-6}$- alkyl, —NH-heteroalkyl-S(O)₂NHC₁₋₆-alkyl, —NH-aryl-S(O)₂NHC₁₋₆-aryl, —NH-alkyl-S(O)₂NHC₁₋₆-aryl, —NH-heteroalkyl-S(O)₂NHC₁₋₆-aryl, —NH-aryl-S(O)₂NHC₁₋₆-heteroaryl, —NH-alkyl-S(O)₂NHC₁₋₆-heteroaryl, —NH-heteroaryl-S(O)₂NHC₁₋₆-heteroaryl, —NH— heteroalkyl-S(O)₂NHC₁₋₆-heteroaryl, —NH-aryl-NHC(O)—C₁₋₆-alkyl, —NH-heteroarylNHC(O)—C₁₋₆-alkyl, —NH-alkyl-NHC(O)—C₁₋₆-alkyl, —NH-aryl-NHC(O)—C₁₋₆-aryl, —NH-aryl-NHC(O)—C₁₋₆-heteroaryl, —NH-aryl-NHC(O)—C₁₋₆-heteroalkyl, —NH-arylNHC(O)—C₁₋₆-alkyl, —NH-alkyl, —NH-aryl, —NH-haloaryl, —NH-haloheteroaryl, —NH-aryl-S(O)C₁₋₆-alkyl, —NH-aryl-NHS(O)₂C₁₋₆-alkyl, —NH-alkyl-NHS(O)₂C₁₋₆-alkyl, —NH-heteroaryl-NHS(O)₂C₁₋₆-alkyl, —NH— heteroalkyl-NHS(O)₂C₁₋₆-alkyl, —NH-aryl-NHS(O)₂C₁₋₆-aryl, —NH-alkyl-NHS(O)₂C₁₋₆-aryl, —NH-heteroaryl-NHS(O)₂C₁₋₆-aryl, —NH-heteroalkyl-NHS(O)₂C₁₋₆-aryl, —NH-aryl-NHS(O)₂C₁₋₆-heteroaryl, —NH-alkyl-NHS(O)₂C₁₋₆-heteroaryl, —NH-heteroaryl-NHS(O)₂C₁₋₆-heteroaryl, —NH-heteroalkyl-NHS(O)₂C₁₋₆-heteroaryl, —NHS(O)₂C₁₋₁₀-alkyl or a fully saturated or partially or fully unsaturated 3-8 membered monocyclic or 6-12 membered bicyclic ring system, the ring system formed of carbon atoms optionally including 1-3 heteroatoms if monocyclic or 1-6 heteroatoms if bicyclic, the heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of the ring system is optionally substituted independently with 1-5 substituents of halo, haloalkyl, haloalkoxyl, CN, NO₂, NH₂, OH, oxo, $C_{1-6}$-alkyl, $C_{1-6}$-alkoxyl, $C_{3-6}$-cycloalkyl, $C_{1-10}$-alkylamino-, $C_{1-10}$-dialkylamino-, benzyl, phenyl, or is a multi-ring moiety comprising at least one substituted or unsubstituted aromatic ring and at least one substituted or unsubstituted nonaromatic ring, or comprises at least one substituted or unsubstituted heteroaromatic ring; and each of p and o, independently, is 1, 2, 3, 4, 5, or 6.

In various embodiments, R1 is:

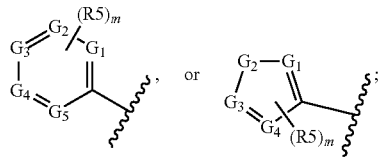

wherein, each of $G_1$, $G_2$, $G_3$, $G_4$ and $G_5$, independently, is CR5, N, NR5, O, or S;

R5 is H, halo, haloalkyl, haloalkoxyl, oxo, CN, OH, SH, NO₂, NH₂, acetyl, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl, C(O)C₁₋₆-alkyl, —C(O)NHC₁₋₆-alkyl, —NHC(O)C₁₋₆-alkyl, —S(O)C₁₋₆-alkyl, —S(O)₂NHC₁₋₆-alkyl, —NHS(O)₂C₁₋₁₀-alkyl or a fully saturated or partially or fully unsaturated 3-8 membered monocyclic or 6-12 membered bicyclic ring system, the ring system formed of carbon atoms optionally including 1-3 heteroatoms if monocyclic or 1-6 heteroatoms if bicyclic, the heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of the ring system is optionally substituted independently with 1-5 substituents of halo, haloalkyl, haloalkoxyl, CN, NO₂, NH₂, OH, oxo, $C_{1-6}$-alkyl, $C_{1-6}$-alkoxyl, $C_{3-6}$-cycloalkyl, $C_{1-10}$-alkylamino-, $C_{1-10}$-dialkylamino-, benzyl or phenyl, or is a multi-ring moiety comprising at least one substituted or unsubstituted aromatic ring and at least one substituted or unsubstituted nonaromatic ring, or comprises at least one substituted or unsubstituted heteroaromatic ring; and m is 1, 2, 3, 4, or 5.

In some embodiments, R5 is:

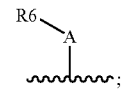

wherein,

A is a single bond or comprises —CH₂R6, —CHR6R6, NHR6, O, S, alkenyl(-C=C—R₆), alkynyl-R₆ (≡R₆), —CONH—R₆; —NHCO—R₆; —SO₂NH—R₆; —NHSO₂—R₆; —NHCONH—R₆; O—R6; S—R6;

R6 is H, halo, haloalkyl, haloalkoxyl, oxo, CN, OH, SH, NO₂, NH₂, acetyl, $C_{1-10}$-alkyl, $C_{2-10}$-alkenyl, $C_{2-10}$-alkynyl, $C_{1-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl, C(O)C₁₋₆-alkyl, —C(O)NHC₁₋₆-alkyl, —NHC(O)C₁₋₆-alkyl, —S(O)C₁₋₆-alkyl, —S(O)₂NHC₁₋₆-alkyl, —NHS(O)₂C₁₋₁₀-alkyl or a fully saturated or partially or fully unsaturated 3-8 membered monocyclic or 6-12 membered bicyclic ring system, the ring system formed of carbon atoms optionally including 1-3 heteroatoms if monocyclic or 1-6 heteroatoms if bicyclic, the heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of the ring system is optionally substituted independently with 1-5 substituents of halo, haloalkyl, haloalkoxyl, CN, NO₂, NH₂, OH, oxo, $C_{1-6}$-alkyl, $C_{1-6}$-alkoxyl, $C_{3-6}$-cycloalkyl, $C_{1-10}$-alkylamino-, $C_{1-10}$-dialkylamino-, benzyl or phenyl, or is a multi-ring moiety comprising at least one substituted or unsubstituted aromatic ring and at least one substituted or unsubstituted nonaromatic ring, or comprises at least one substituted or unsubstituted heteroaromatic ring; and n is 1, 2, 3, 4, or 5.

In various embodiments, A comprises:

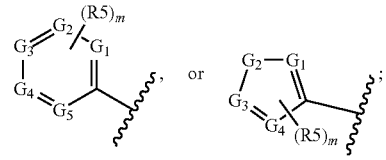

wherein, each of $G_1$, $G_2$, $G_3$, $G_4$ and $G_5$, independently, is CR5, N, NR5, O, or S;

R5 is H, halo, haloalkyl, haloalkoxyl, oxo, CN, OH, SH, NO$_2$, NH$_2$, acetyl, C$_{1-10}$-alkyl, C$_{2-10}$-alkenyl, C$_{2-10}$-alkynyl, C$_{3-10}$-cycloalkyl, C$_{4-10}$cycloalkenyl, C$_{1-10}$-alkylamino-, C$_{1-10}$-dialkylamino-, C$_{1-10}$-alkoxyl, C$_{1-10}$-thioalkoxyl, C(O)C$_{1-6}$-alkyl, —C(O)NHC$_{1-6}$-alkyl, —NHC(O)C$_{1-6}$-alkyl, —S(O)C$_{1-6}$-alkyl, —S(O)$_2$NHC$_{1-6}$-alkyl, —NHS(O)$_2$C$_{1-10}$-alkyl or a fully saturated or partially or fully unsaturated 3-8 membered monocyclic or 6-12 membered bicyclic ring system, the ring system formed of carbon atoms optionally including 1-3 heteroatoms if monocyclic or 1-6 heteroatoms if bicyclic, the heteroatoms selected from O, N, or S, wherein each of the C$_{1-10}$-alkyl, C$_{2-10}$-alkenyl, C$_{2-10}$-alkynyl, C$_{3-10}$-cycloalkyl, C$_{4-10}$-cycloalkenyl, C$_{1-10}$-alkylamino-, C$_{1-10}$-dialkylamino-, C$_{1-10}$-alkoxyl, C$_{1-10}$-thioalkoxyl and ring of the ring system is optionally substituted independently with 1-5 substituents of halo, haloalkyl, haloalkoxyl, CN, NO$_2$, NH$_2$, OH, oxo, C$_{1-6}$-alkyl, C$_{1-6}$-alkoxyl, C$_{3-6}$-cycloalkyl, C$_{1-10}$-alkylamino-, C$_{1-10}$-dialkylamino-, benzyl or phenyl, or is a multi-ring moiety comprising at least one substituted or unsubstituted aromatic ring and at least one substituted or unsubstituted nonaromatic ring, or comprises at least one substituted or unsubstituted heteroaromatic ring; and m is 1, 2, 3, 4, or 5.

In various embodiments, R5 is:

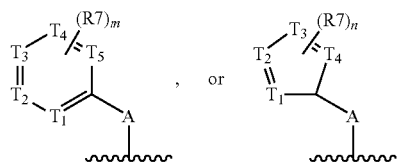

wherein,

A is a single bond or comprises —CH$_2$R6, —CHR6-, NHR6, O, S, alkenyl(-C=C—R$_6$), alkynyl-R$_6$, (=R$_6$), —CONH—R$_6$, —NHCO—R$_6$, —SO$_2$NH—R$_6$, —NHSO$_2$—R$_6$; —NHCONH—R$_6$, O—R6, or S—R6;

each of T$_1$, T$_2$, T$_3$, T$_4$ and T$_5$, independently, is CR6, N, NR6, O, or S;

each of R6 and R7 is, independently, H, halo, haloalkyl, haloalkoxyl, oxo, CN, OH, SH, NO$_2$, NH$_2$, acetyl, C$_{1-10}$-alkyl, C$_{2-10}$-alkenyl, C$_{2-10}$-alkynyl, C$_{3-10}$-cycloalkyl, C$_{4-10}$-cycloalkenyl, C$_{1-10}$-alkylamino-, C$_{1-10}$-dialkylamino-, C$_{1-10}$-alkoxyl, C$_{1-10}$-thioalkoxyl, C(O)C$_{1-6}$-alkyl, —C(O)NHC$_{1-6}$-alkyl, —NHC(O)C$_{1-6}$-alkyl, —S(O)C$_{1-6}$-alkyl, —S(O)$_2$NHC$_{1-6}$-alkyl, —NHS(O)$_2$C$_{1-10}$-alkyl or a fully saturated or partially or fully unsaturated 3-8 membered monocyclic or 6-12 membered bicyclic ring system, the ring system formed of carbon atoms optionally including 1-3 heteroatoms if monocyclic or 1-6 heteroatoms if bicyclic, the heteroatoms selected from O, N, or S, wherein each of the C$_{1-10}$-alkyl, C$_{2-10}$-alkenyl, C$_{2-10}$-alkynyl, C$_{3-10}$-cycloalkyl, C$_{4-10}$-cycloalkenyl, C$_{1-10}$-alkylamino-, C$_{1-10}$-dialkylamino-, C$_{1-10}$-alkoxyl, C$_{1-10}$-thioalkoxyl and ring of the ring system is optionally substituted independently with 1-5 substituents of halo, haloalkyl, haloalkoxyl, CN, NO$_2$, NH$_2$, OH, oxo, C$_{1-6}$-alkyl, C$_{1-6}$-alkoxyl, C$_{3-6}$-cycloalkyl, C$_{1-10}$-alkylamino-, C$_{1-10}$-dialkylamino-, benzyl or phenyl, or is a multi-ring moiety comprising at least one substituted or unsubstituted aromatic ring and at least one substituted or unsubstituted nonaromatic ring, or comprises at least one substituted or unsubstituted heteroaromatic ring; and n is 1, 2, 3, 4, or 5.

In some embodiments, R5 is:

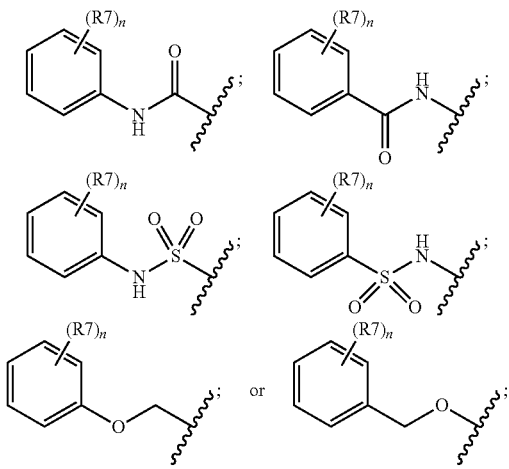

wherein,

R7 is H, halo, haloalkyl, haloalkoxyl, oxo, CN, OH, SH, NO$_2$, NH$_2$, acetyl, C$_{1-10}$-alkyl, C$_{2-10}$-alkenyl, C$_{2-10}$-alkynyl, C$_{3-10}$-cycloalkyl, C$_{4-10}$-cycloalkenyl, C$_{1-10}$-alkylamino-, C$_{1-10}$-dialkylamino-, C$_{1-10}$-alkoxyl, C$_{1-10}$-thioalkoxyl, C(O)C$_{1-6}$-alkyl, —C(O)NHC$_{1-6}$-alkyl, —NHC(O)C$_{1-6}$-alkyl, —S(O)C$_{1-6}$-alkyl, —S(O)$_2$NHC$_{1-6}$-alkyl, —NHS(O)$_2$C$_{1-10}$-alkyl or a fully saturated or partially or fully unsaturated 3-8 membered monocyclic or 6-12 membered bicyclic ring system, the ring system formed of carbon atoms optionally including 1-3 heteroatoms if monocyclic or 1-6 heteroatoms if bicyclic, the heteroatoms selected from O, N, or S, wherein each of the C$_{1-10}$-alkyl, C$_{2-10}$-alkenyl, C$_{2-10}$-alkynyl, C$_{3-10}$-cycloalkyl, C$_{4-10}$-cycloalkenyl, C$_{1-10}$-alkylamino-, C$_{1-10}$-dialkylamino-, C$_{1-10}$-alkoxyl, C$_{1-10}$-thioalkoxyl and ring of the ring system is optionally substituted independently with 1-5 substituents of halo, haloalkyl, haloalkoxyl, CN, NO$_2$, NH$_2$, OH, oxo, C$_{1-6}$-alkyl, C$_{1-6}$-alkoxyl, C$_{3-6}$-cycloalkyl, C$_{1-10}$-alkylamino-, C$_{1-10}$-dialkylamino-, benzyl or phenyl, or is a multi-ring moiety comprising at least one substituted or unsubstituted aromatic ring and at least one substituted or unsubstituted nonaromatic ring, or comprises at least one substituted or unsubstituted heteroaromatic ring; and n is 1, 2, 3, 4, or 5.

In other embodiments, R5 of each of two of G$_1$, G$_2$, G$_3$, G$_4$, or G$_5$ taken together form a fully saturated or partially or fully unsaturated 3-8 membered monocyclic or 6-12 membered bicyclic ring system, the ring system formed of carbon atoms optionally including 1-3 heteroatoms if monocyclic or 1-6 heteroatoms if bicyclic, the heteroatoms selected from O, N, or S.

In various embodiments, the compound is a pyrrolo[2,3-d]pyrimidine. The pyrrolo[2,3-d]pyrimidine may be a compound of Formula (IV):

(IV)

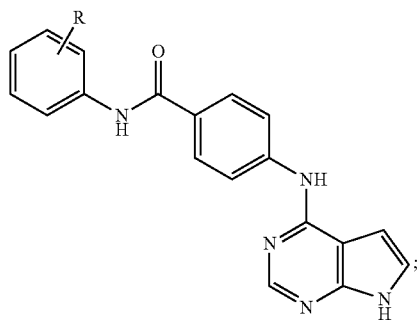

wherein R is 2'-ClPh, 3'-ClPh, 4'-ClPh, 2'CH₃Ph, 3'CH₃Ph, 4'CH₃Ph, 2'-OCH₃Ph, 3'-OCH₃Ph, 4'-OCH₃Ph, 2'FPh, 3'FPh, 4'FPh, 2'-C₆H₅N, 3'-C₆H₅N, 4'-C₆H₅N, 2'-C₄H₆N₂, 3'-C₄H₆N₂, 4'-C₄H₆N₂, cyclohexyl, cyclopentyl, or tert-butyl.

The pyrrolo[2,3-d]pyrimidine may be a compound of Formula (V):

(V)

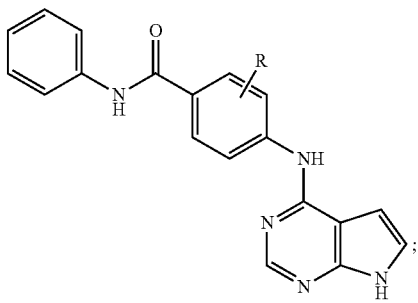

wherein R is 2-Cl, 3-Cl, 2-CH₃, 3-CH₃, 2-F, 3-F, 2-OCH₃, or 3-OCH₃.

The pyrrolo[2,3-d]pyrimidine may be a compound of Formula (VI):

(VI)

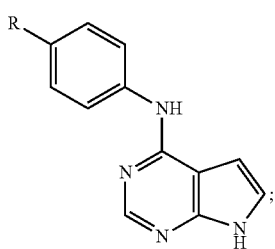

wherein R is:

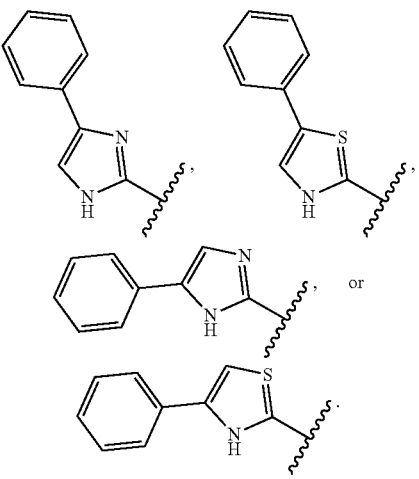

The pyrrolo[2,3-d]pyrimidine may be a compound of Formula (VII):

(VII)

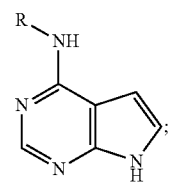

wherein R is:

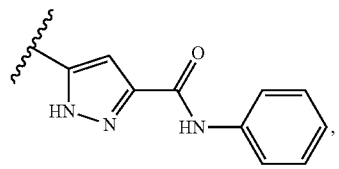

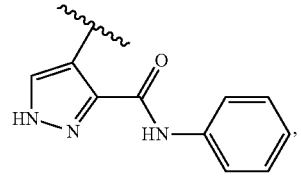

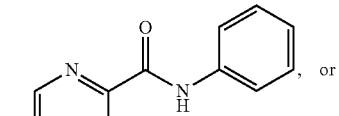, or

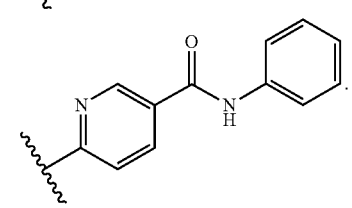

The pyrrolo[2,3-d]pyrimidine may be a compound of Formula (VIII):

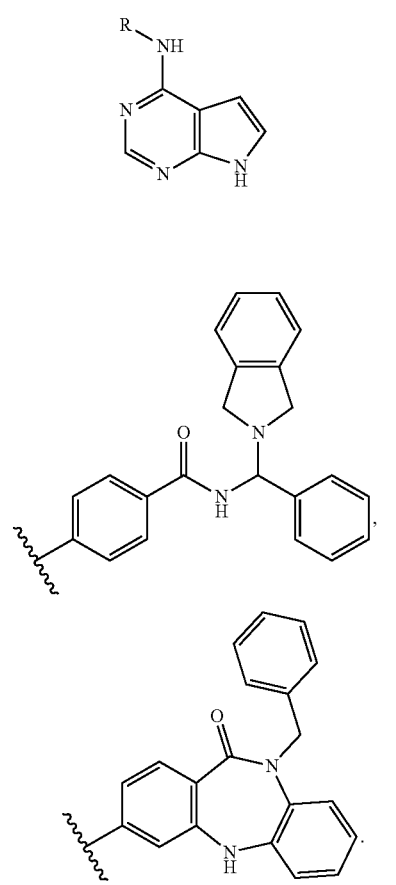

The pyrrolo[2,3-d]pyrimidine may be a compound of Formula (IX):

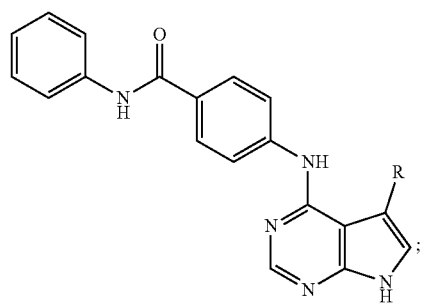

wherein R is:

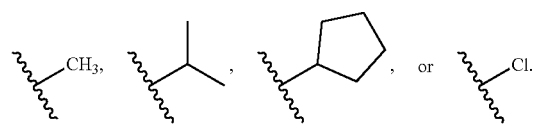

The pyrrolo[2,3-d]pyrimidine may be a compound of Formula (X):

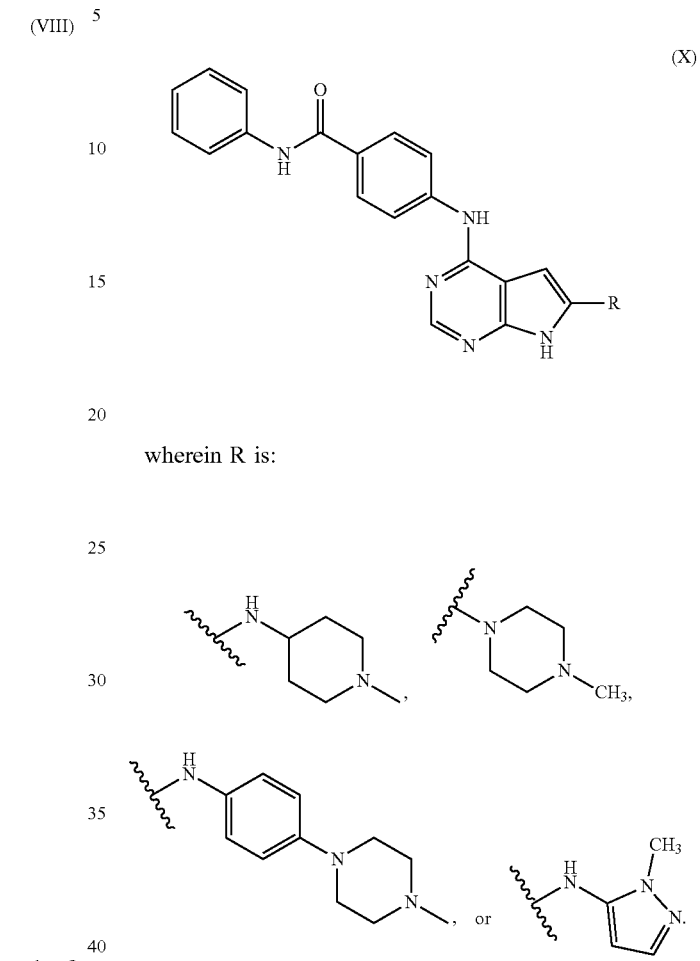

wherein R is:

The pyrrolo[2,3-d]pyrimidine may be a compound of Formula (XI):

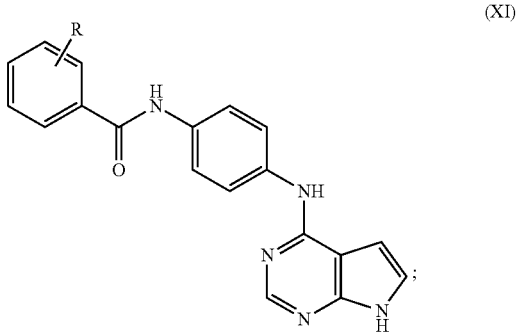

wherein R is 2'-ClPh, 3'-ClPh, 4'-ClPh, 2'CH$_3$Ph, 3'CH$_3$Ph, 4'CH$_3$Ph, 2'-OCH$_3$Ph, 3'-OCH$_3$Ph, 4'-OCH$_3$Ph, 2'FPh, 3'FPh, 4'FPh, 2'-C$_6$H$_5$N, 3'-C$_6$H$_5$N, 4'-C$_6$H$_5$N, 2'-C$_4$H$_6$N$_2$, 3'-C$_4$H$_6$N$_2$, 4'-C$_4$H$_6$N$_2$, NHC$_6$H$_5$, CH$_2$C$_6$H$_5$, or CH$_2$CH$_2$C$_6$H$_5$.

The pyrrolo[2,3-d]pyrimidine may be a compound of Formula (XII):
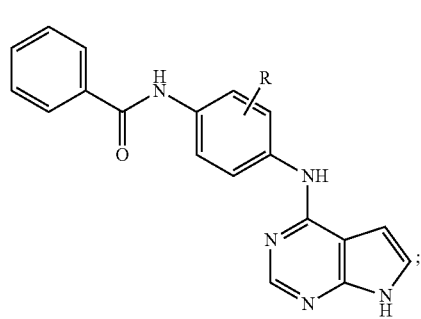
(XII)
wherein R is 2-Cl, 3-Cl, 2-CH₃, 3-CH₃, 2-F, 3-F, 2-OCH₃, or 3-OCH₃.
The pyrrolo[2,3-d]pyrimidine may be a compound of Formula (XIII):
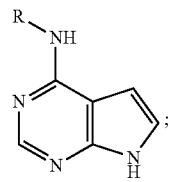
(XIII)
wherein R is:
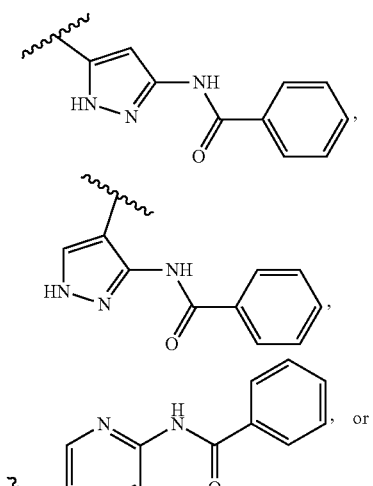
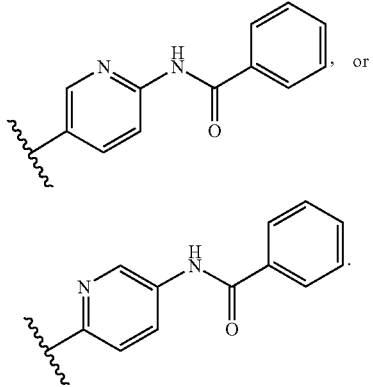
, or
The pyrrolo[2,3-d]pyrimidine may be a compound of Formula (XIV):
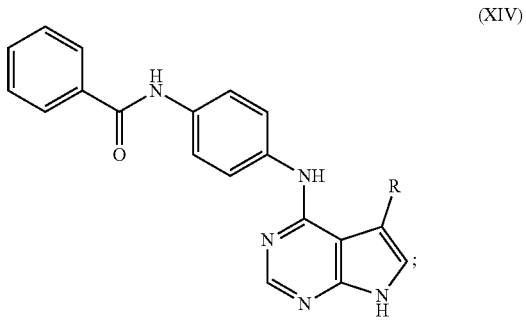
(XIV)
wherein R is:
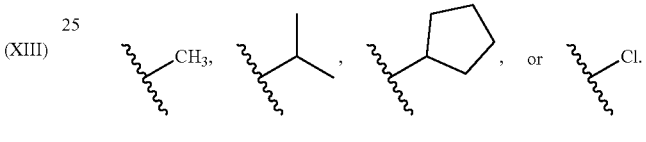
The pyrrolo[2,3-d]pyrimidine may be a compound of Formula (XV):
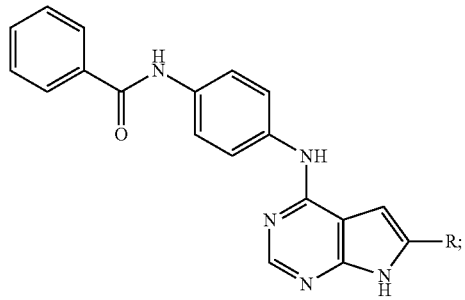
(XV)
wherein R is:
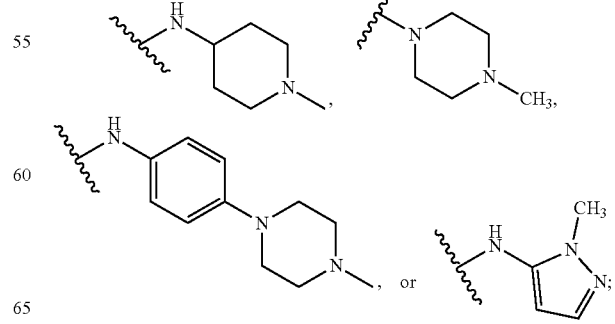

The pyrrolo[2,3-d]pyrimidine may be a compound of Formula (XVI):

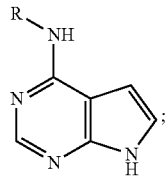
(XVI)

wherein R is:

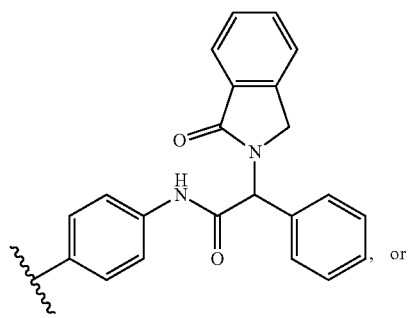
, or

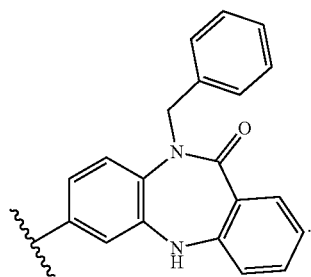

In various embodiments, the compound is a pyrazolopyrimidine. The pyrazolopyrimidines may be a compound of Formula (XVII):

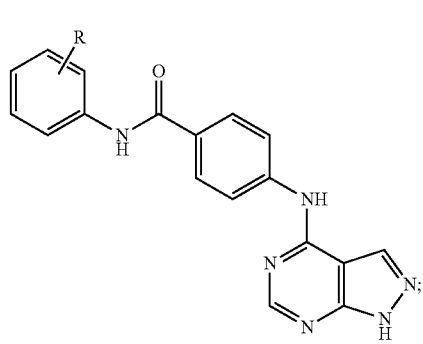
(XVII)

wherein R is 2'-ClPh, 3'-ClPh, 4'-ClPh, 2'CH₃Ph, 3'CH₃Ph, 4'CH₃Ph, 2'-OCH₃Ph, 3'-OCH₃Ph, 4'-OCH₃Ph, 2'FPh, 3'FPh, 4'FPh, 2'-C₆H₅N, 3'-C₆H₅N, 4'-C₆H₅N, 2'-C₄H₆N₂, 3'-C₄H₆N₂, 4'-C₄H₆N₂, cyclohexyl, cyclopentyl, or tert-butyl.

The pyrazolopyrimidine may be a compound of Formula (XVIII):

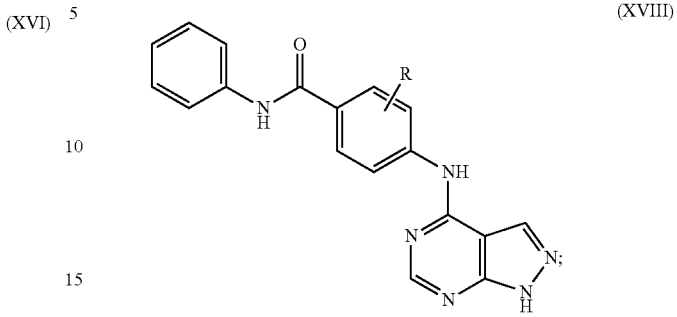
(XVIII)

wherein R is 2-Cl, 3-Cl, 2-CH3, 3-CH3, 2-F, 3-F, 2-OCH₃, or 3-OCH₃.

The pyrazolopyrimidine may be a compound of Formula (XIX):

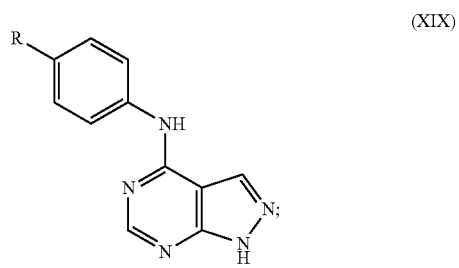
(XIX)

wherein R is:

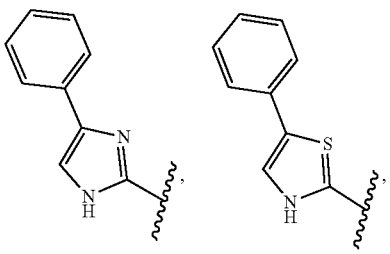
, or

The pyrazolopyrimidine may be a compound of Formula (XX):

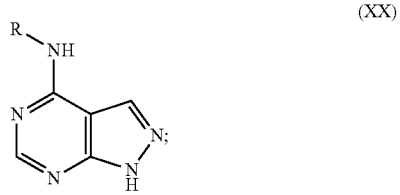
(XX)

wherein R is:
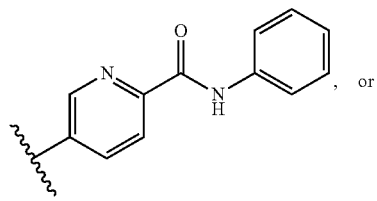, or
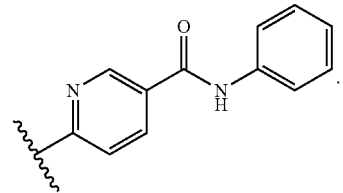.
The pyrazolopyrimidine may be a compound of Formula (XXI):
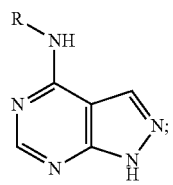 (XXI)
wherein R is:
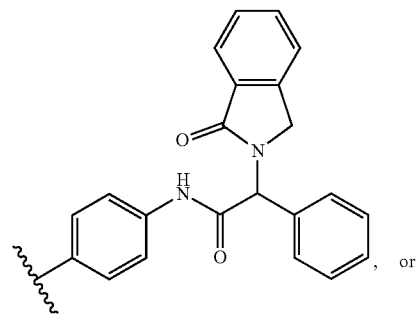, or
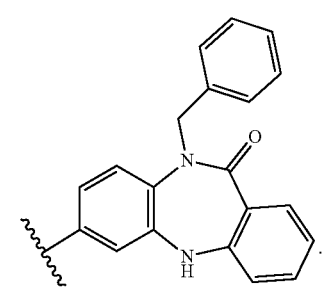.
The pyrazolopyrimidine may be a compound of Formula (XXII):
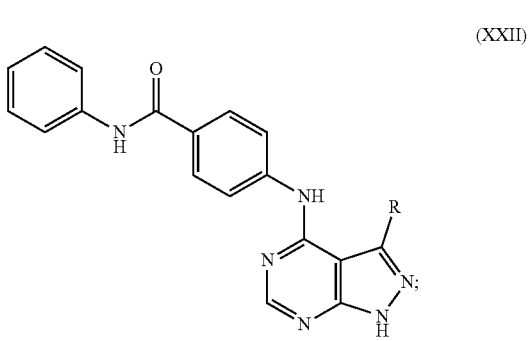 (XXII)
wherein R is:
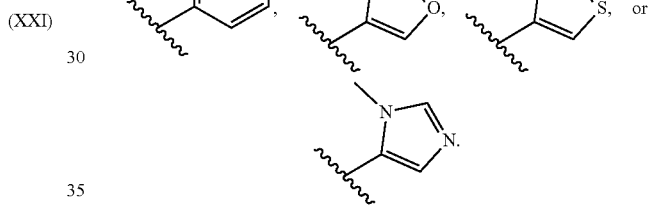
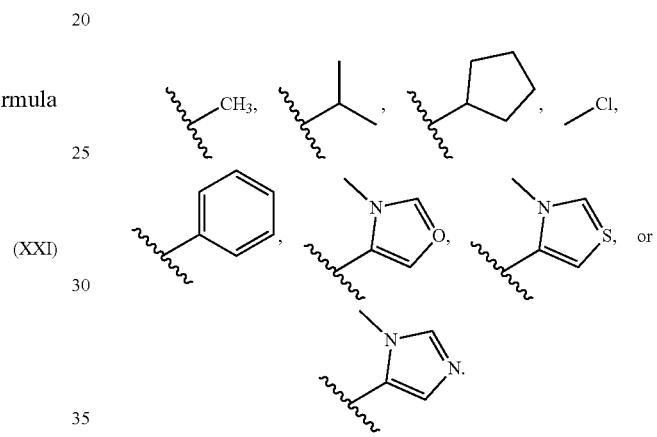
The pyrazolopyrimidine may be a compound of Formula (XXIII):
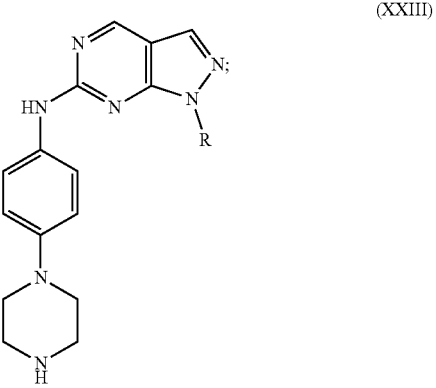 (XXIII)
wherein R is:
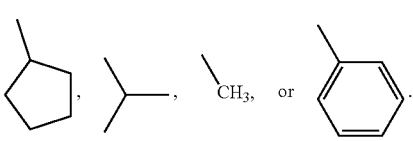

In some exemplary embodiments, the pyrazolopyrimidine is:

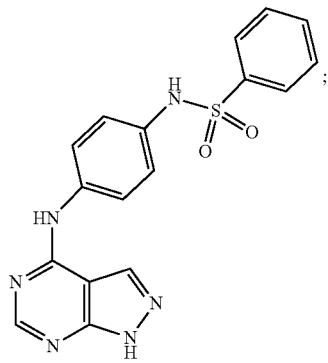

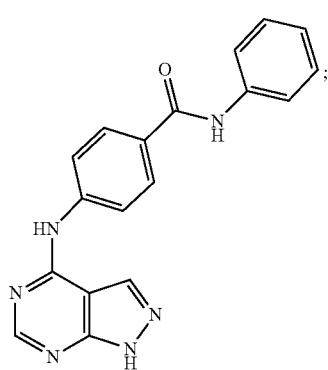

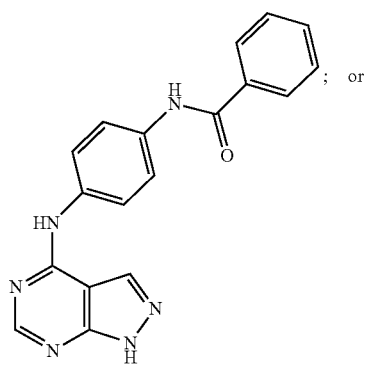 ; or

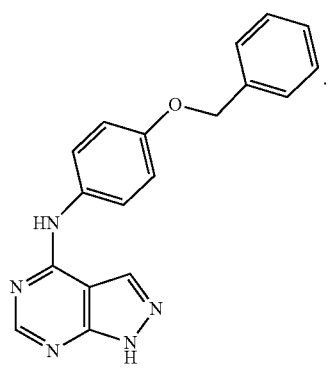

In various embodiments, the compound is a quinazolines. The quinazolines may be a compound of Formula (XXIV):

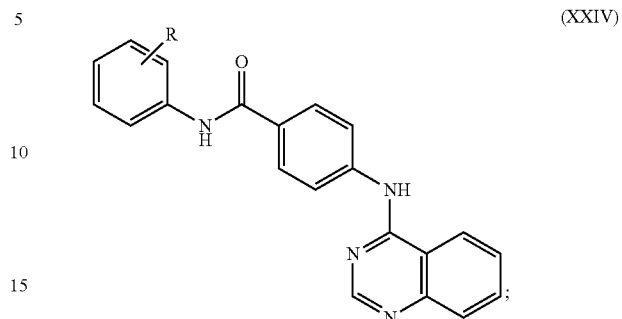
(XXIV)

wherein R is 2'-ClPh, 3'-ClPh, 4'-ClPh, 2'CH$_3$Ph, 3'CH$_3$Ph, 4'CH$_3$Ph, 2'-OCH$_3$Ph, 3'-OCH$_3$Ph, 4'-OCH$_3$Ph, 2'FPh, 3'FPh, 4'FPh, 2'-C$_6$H$_5$N, 3'-C$_6$H$_5$N, 4'-C$_6$H$_5$N, 2'-C$_4$H$_6$N$_2$, 3'-C$_4$H$_6$N$_2$, 4'-C$_4$H$_6$N$_2$, cyclohexyl, cyclopentyl, or tert-butyl.

The quinazolines may be a compound of Formula (XXV):

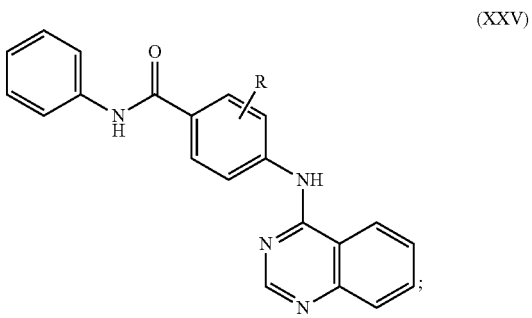
(XXV)

wherein R is 2-Cl, 3-Cl, 2-CH$_3$, 3-CH$_3$, 2-F, 3-F, 2-OCH$_3$, or 3-OCH$_3$.

The quinazolines may be a compound of Formula (XXVI):

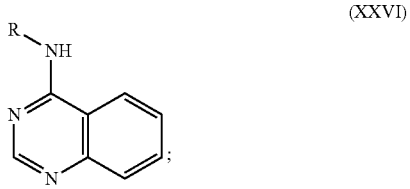
(XXVI)

wherein R is:

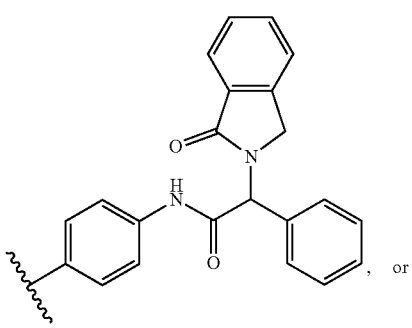 , or

-continued
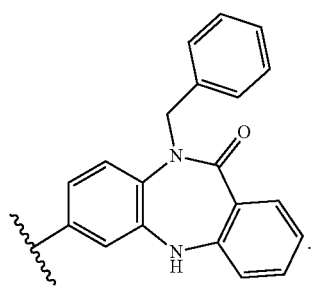
The quinazolines may be a compound of Formula (XXVII):
(XXVII)
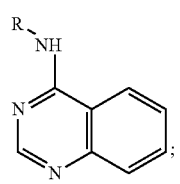
wherein R is:
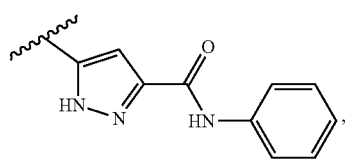,
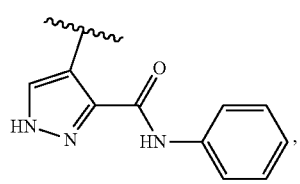,
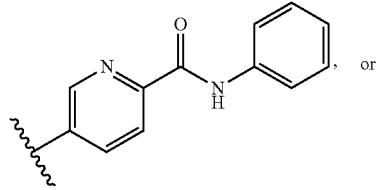, or
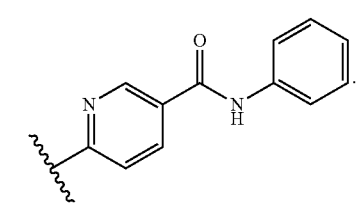.
The quinazolines may be a compound of Formula (XXVIII):
(XXVIII)
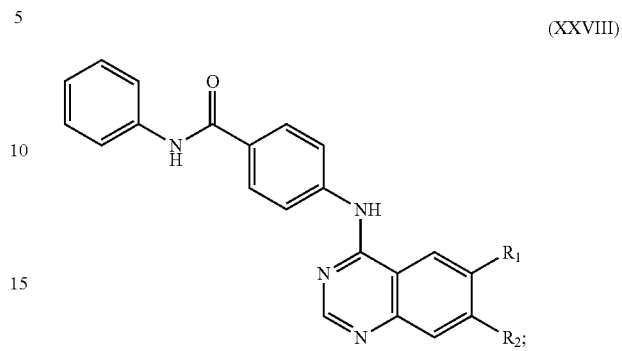
wherein one of R1 and R2 is:
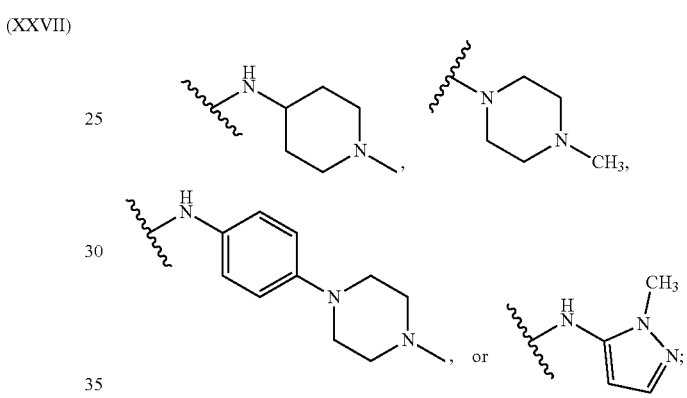
with the proviso that the other of R1 and R2 is H.
The quinazolines may be a compound of Formula (XXIX):
(XXIV)
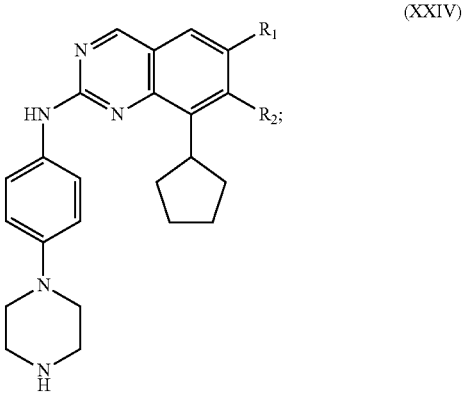
wherein one of R1 and R2 is:
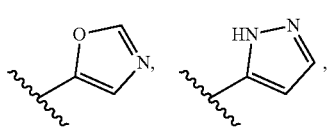

-continued

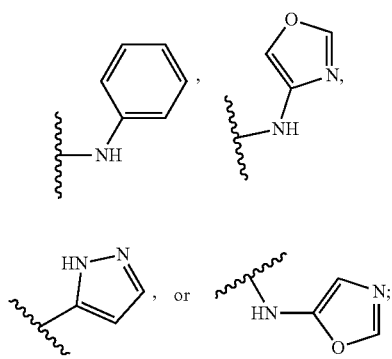

with the proviso that the other of R1 and R2 is H.

In various embodiments, the compound is a 2,6,7-trisubstituted pyrrolo[2,3-d]pyrimidines. The 2,6,7-trisubstituted pyrrolo[2,3-d]pyrimidines may be a compound of Formula (XXX):

(XXX)

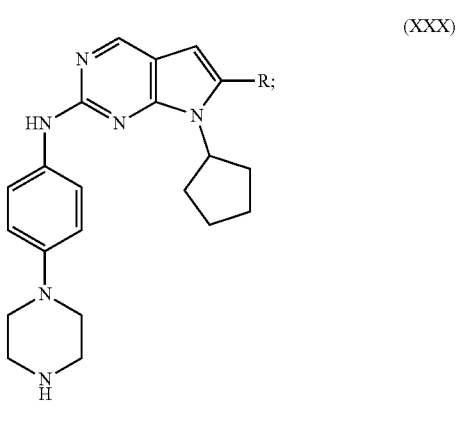

wherein R is:

The 2,6,7-trisubstituted pyrrolo[2,3-d]pyrimidines may be a compound of Formula (XXXI):

(XXXI)

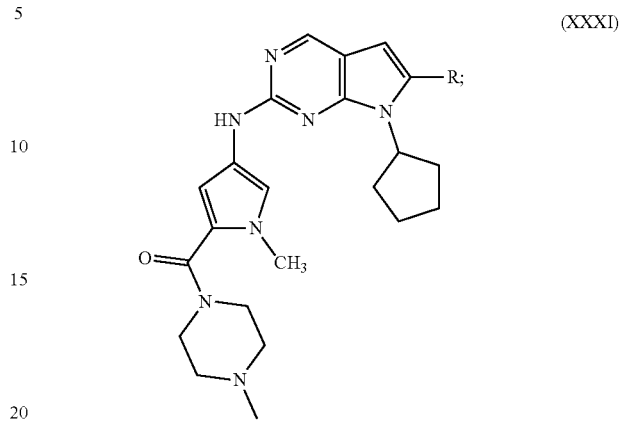

wherein R is:

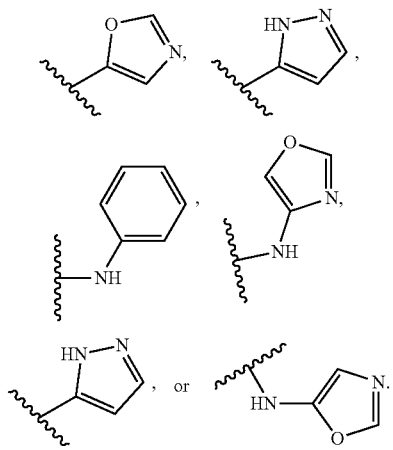

The 2,6,7-trisubstituted pyrrolo[2,3-d]pyrimidines may be a compound of Formula (XXXII):

(XXXII)

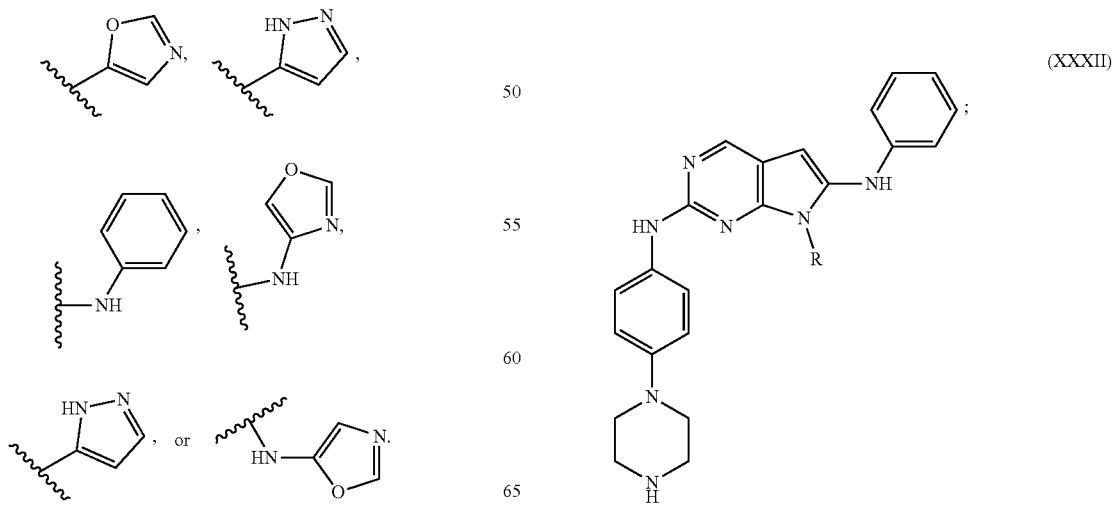

wherein R is:

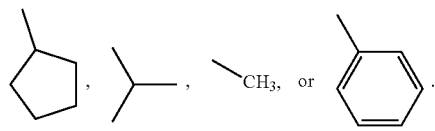

The 2,6,7-trisubstituted pyrrolo[2,3-d]pyrimidines may be a compound of Formula (XXXIII):

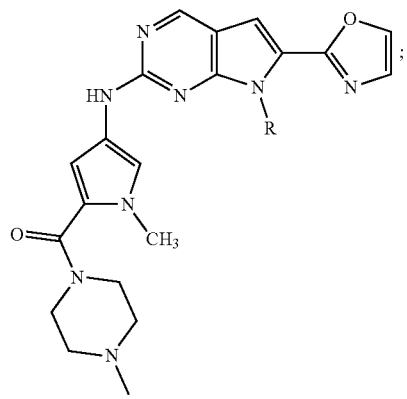

(XXXIII)

wherein R is:

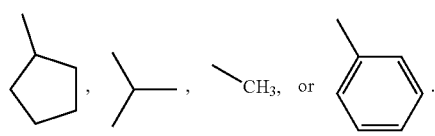

The 2,6,7-trisubstituted pyrrolo[2,3-d]pyrimidines may be a compound of Formula (XXXIV):

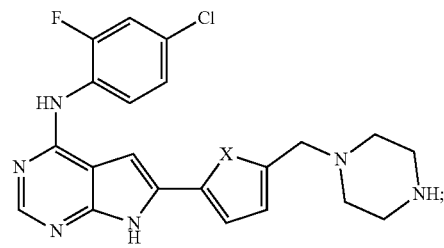

(XXXIV)

wherein X is O, S, NH, or C=C.

The 2,6,7-trisubstituted pyrrolo[2,3-d]pyrimidines may be a compound of Formula (XXXV):

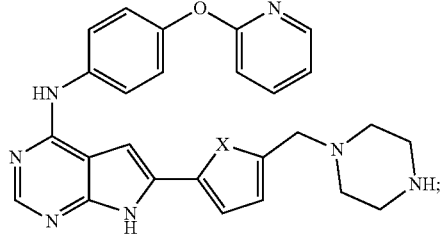

(XXXV)

wherein X is O, S, NH, or C=C.

In some exemplary embodiments, the 2,6,7-trisubstituted pyrrolo[2,3-d]pyrimidines is:

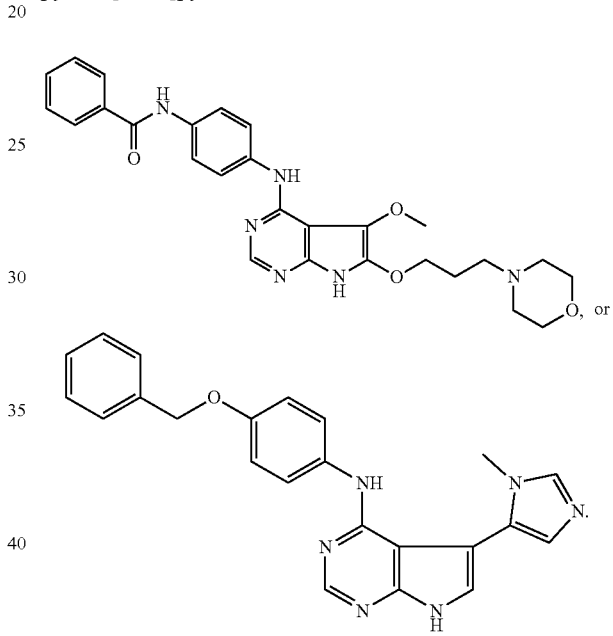

In various embodiments, the compound is a 2,4,7-trisubstituted pyrrolo[2,3-d]pyrimidines. The 2,4,7-trisubstituted pyrrolo[2,3-d]pyrimidines may be a compound of Formula (XXXVI):

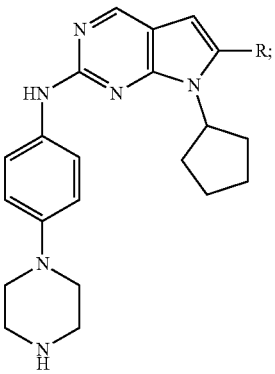

(XXXVI)

wherein R is:

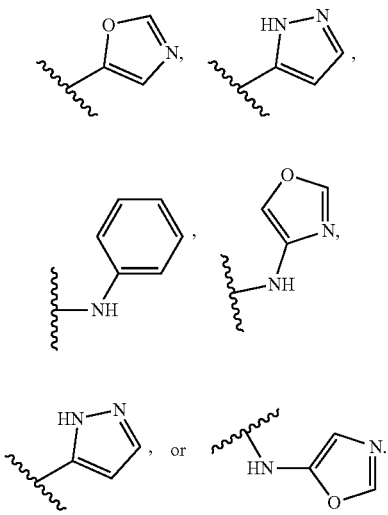

The 2,4,7-trisubstituted pyrrolo[2,3-d]pyrimidines may be a compound of Formula (XXXVI):

(XXXVI)

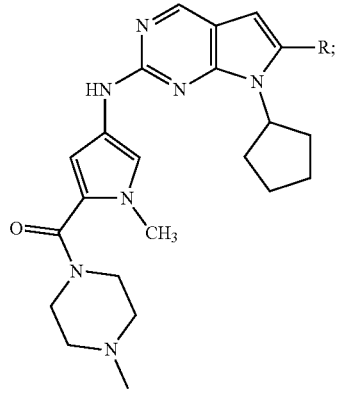

wherein R is:

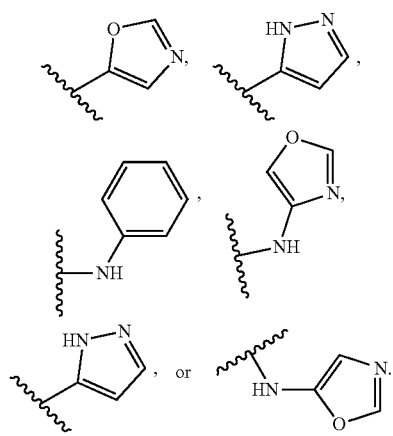

The 2,4,7-trisubstituted pyrrolo[2,3-d]pyrimidines may be a compound of Formula (XXXVII):

(XXXVII)

wherein R is:

The 2,4,7-trisubstituted pyrrolo[2,3-d]pyrimidines may be a compound of Formula (XXXVIII):

(XXXVIII)

wherein R is:

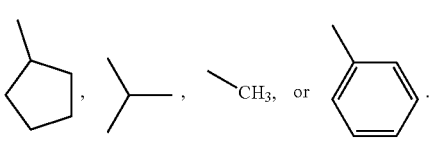

In various embodiments, the compound is a 2,7,8-trisubstituted quinazoline. The 2,7,8-trisubstituted quinazoline may be substituted as described in Formulas I to XXXVIII above.

In some exemplary embodiments, the compound is:
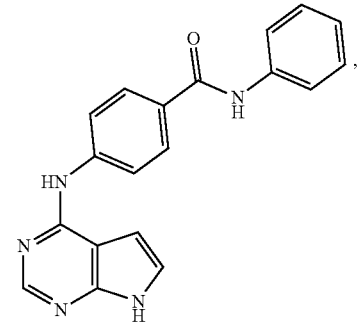,
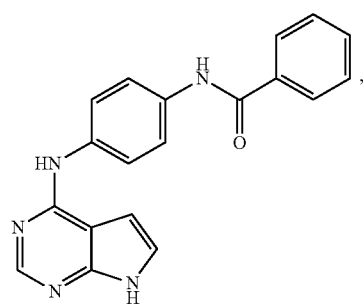,
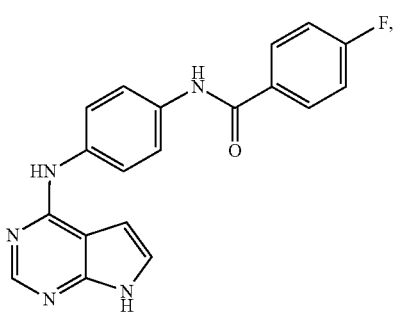,
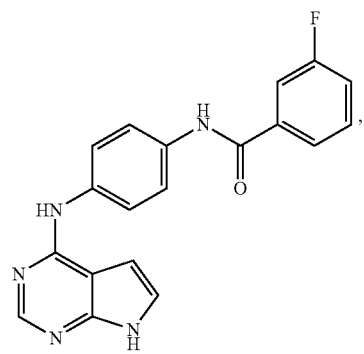,
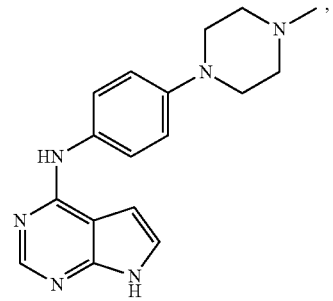,
-continued
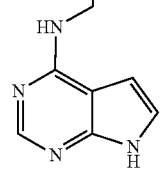
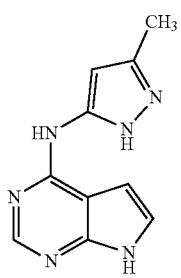,
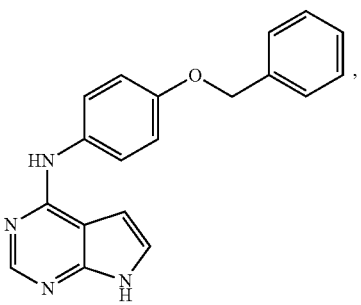,
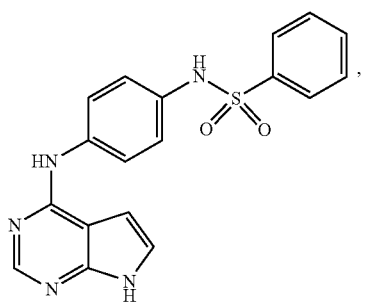,
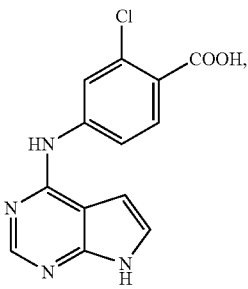,
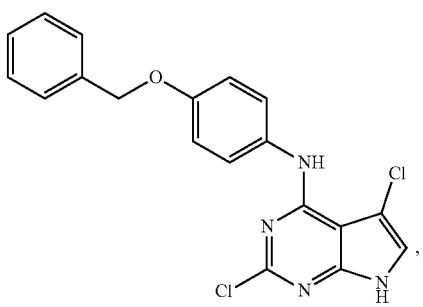, 37
-continued

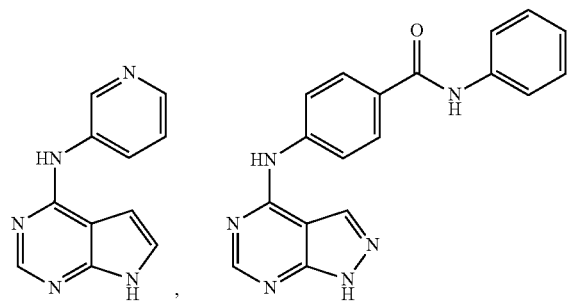

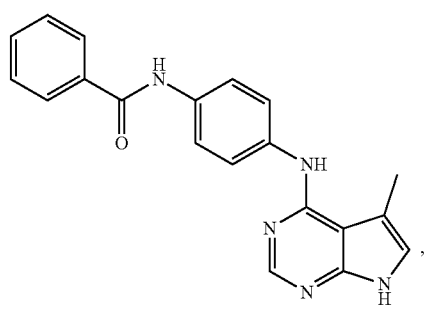

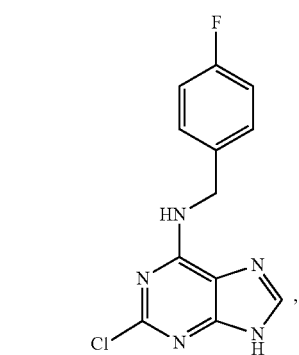

38
-continued

[chemical structures]

, or

[chemical structure]

In some exemplary embodiments, the compound is a compound of Formula (I-2):

$$\begin{array}{c}\text{(I-2)}\\ \text{[structure with } L^1, L^2, X^1, X^2, X^3, X^4, X^5\text{]}\end{array}$$

or a pharmaceutically acceptable salt thereof;
wherein:
  $X^1$ is N;
  $X^2$ is N;
  $X^3$ is NH;
  $X^4$ is N or $CR^2$;
    wherein $R^2$ is H, COOH, a 5-membered heteroaryl, or $X^6R^3$;
      wherein the 5-membered heteroaryl contains 1 N heteroatom and 1 additional heteroatom selected from the group consisting of N, O, and S;
      wherein the 5-membered heteroaryl is optionally substituted with 1, 2, or 3 substituents independently selected from the group consisting of halo, CN, $NO_2$, $C_{1-6}$ alkyl, $C_{1-6}$ haloalkyl, $CH_2$-phenyl, $NH_2$, $NHC_{1-10}$ alkyl, $N(C_{1-10}$ alkyl$)_2$, OH, $OC_{1-6}$ alkyl, $OC_{1-6}$ haloalkyl, $C_{3-6}$ cycloalkyl, and phenyl;
      wherein $X^6$ is $CONH(CH)_m$, $NHCO(CH)_m$, $CH_2CH_2$, C=C, C≡C, $CH_2$, S, $NH(CH)_m$, or COO;
    wherein $R^3$ is a 5-membered heteroaryl, 6-membered heteroaryl, or substituted phenyl;
      wherein the 5-membered or 6-membered heteroaryl contains 1 N heteroatom and 1-3 additional heteroatoms selected from the group consisting of N, O, and S, and is optionally substituted with 1, 2, or 3 substituents independently selected from the group consisting of halo, $C_{1-6}$ alkyl, $C_{1-6}$ haloalkyl, $C_{1-6}$ alkylamino, $C_{1-6}$ cycloalkylamino, $NH_2$, $NHC_{1-10}$ alkyl, $NHC_{1-10}$ aryl, $NHC_{1-10}$ alkenyl, $NHC_{1-10}$ alkynyl $N(C_{1-10}$ alkyl$)_2$, OH, COOH, $CH_2COOH$, $OC_{1-6}$ alkyl, $OC_{1-6}$ haloalkyl, $C_{3-6}$ cycloalkyl, and phenyl, $CONHC_{1-10}$, CONHalkyl, $CONH(C_{1-10}$ alkyl$)_2$, CONHalkenyl, $CH_2CONHalkenyl$, $CONHC_{1-6}$ cycloalkyl, $CONHC_{1-10}$, $CONHC_{3-6}$ cycloalkylamine, $CONHC_{3-6}$ aminophenyl, $CONHC_{1-6}$ heteroarylamine, $CONHC_{1-6}$ alkylcarboxylate, $CONHC_{1-6}$ cycloalkylcarboxylate, $CONHC_{1-6}$ heteroarylcarboxylate, $CONHC_{1-6}$ phenylcarboxylate, $NHCOC_{1-10}$ NHCOalkyl, NHCO$(C_{1-10}$ alkyl$)_2$, NHCOalkenyl, NHCOalkenyl$(C_{1-6}$alkyl$)N(C_{1-10}$alkyl$)_2$, $CH_2NHCOalkenyl$, $NHCOC_{1-6}$ cycloalkyl, $NHCOC_{1-10}$, $NHCOC_{3-10}$cycloalkylamine, $NHCOC_{1-10}$ aminophenyl, $NHCOC_{1-6}$ heteroarylamine, $NHCOC_{1-6}$ alkylcarboxylate, $NHCOC_{1-6}$ cycloalkylcarboxylate, $NHCOC_{1-6}$ heteroarylcarboxylate;

wherein the heteroaryl is a pyrimidine, a pyridine, a pyrazole, an isoxazole, or a tetrazole;

wherein the cycloalkylamine is an aminopyrrolidine, an aminopiperidine, or an aminopiperazine;

wherein the substituted phenyl is optionally substituted with 1, 2, or 3 substituents independently selected from the group consisting of halo, $C_{1-6}$ alkyl, $C_{1-6}$ haloalkyl, $C_{1-6}$ alkylamino, $C_{1-6}$ cycloalkylamino, $NH_2$, $NHC_{1-10}$ alkyl, $NHC_{1-10}$ aryl, $NHC_{1-10}$ alkenyl, $NHC_{1-10}$ alkynyl $N(C_{1-10}$ alkyl$)_2$, OH, COOH, $CH_2COOH$, $OC_{1-6}$ alkyl, $OC_{1-6}$ haloalkyl, $C_{3-6}$ cycloalkyl, and phenyl, $CONHC_{1-10}$, CONHalkyl, $CONH(C_{1-10}$ alkyl$)_2$, CONHalkenyl, $CH_2CONHalkenyl$, $CONHC_{1-6}$ cycloalkyl, $CONHC_{1-10}$, $CONHC_{3-6}$ cycloalkylamine, $CONHC_{3-6}$ aminophenyl, $CONHC_{1-6}$ heteroarylamine, $CONHC_{1-6}$ alkylcarboxylate, $CONHC_{1-6}$ cycloalkylcarboxylate, $CONHC_{1-6}$ heteroarylcarboxylate, $CONHC_{1-6}$ phenylcarboxylate, $NHCOC_{1-10}$ NHCOalkyl, NHCO$(C_{1-10}$ alkyl$)_2$, NHCOalkenyl, NHCOalkenyl$(C_{1-6}$alkyl$)N(C_{1-10}$alkyl$)_2$, $CH_2NHCOalkenyl$, $NHCOC_{1-6}$ cycloalkyl, $NHCOC_{1-10}$, $NHCOC_{3-10}$ cycloalkylamine, $NHCOC_{1-10}$ aminophenyl, $NHCOC_{1-6}$ heteroarylamine, $NHCOC_{1-6}$ alkylcarboxylate, $NHCOC_{1-6}$ cycloalkylcarboxylate, $NHCOC_{1-6}$ heteroarylcarboxylate;

$X^5$ is CH, $C(CH_3)$, CCOOH, or $CX^7R^8$;

wherein $X^7$ is C, C—CONH$(CH)_m$, C—NHCO$(CH)_m$, C—$CH_2CH_2$, C—C=C, C—C≡C, C—$CH_2$, C—S, C—NH$(CH)_m$, C—C, C—COO; and wherein $R^8$ is a 5-membered heteroaryl, a 6-membered heteroaryl, or substituted phenyl;

wherein the 5-membered or 6-membered heteroaryl contains 1 N heteroatom and 1-3 additional heteroatom selected from the group consisting of N, O, and S, and is optionally substituted with 1, 2, or 3 substituents independently selected from the group consisting of halo, $C_{1-6}$ alkyl, $C_{1-6}$ haloalkyl, $C_{1-6}$ alkylamino, $C_{1-6}$ cycloalkylamino, $NH_2$, $NHC_{1-10}$ alkyl, $NHC_{1-10}$ aryl, $NHC_{1-10}$ alkenyl, $NHC_{1-10}$alkynyl $N(C_{1-10}$ alkyl$)_2$, OH, COOH, $CH_2COOH$, $OC_{1-6}$ alkyl, $OC_{1-6}$ haloalkyl, $C_{3-6}$ cycloalkyl, and phenyl, $CONHC_{1-10}$, CONHalkyl, $CONH(C_{1-10}$ alkyl$)_2$, CONHalkenyl, $CH_2CONHalkenyl$, $CONHC_{1-6}$ cycloalkyl, $CONHC_{1-10}$, $CONHC_{3-6}$ cycloalkylamine, $CONHC_{3-6}$ aminophenyl, $CONHC_{1-6}$ heteroarylamine, $CONHC_{1-6}$ alkylcarboxylate, $CONHC_{1-6}$ cycloalkylcarboxylate, $CONHC_{1-6}$ heteroarylcarboxylate, $CONHC_{1-6}$ phenylcarboxylate, $NHCOC_{1-10}$ NHCOalkyl, NHCO$(C_{1-10}$ alkyl$)_2$, NHCOalkenyl, NHCOalkenyl$(C_{1-6}$alkyl$)N(C_{1-10}$alkyl$)_2$, $CH_2NHCOalkenyl$, $NHCOC_{1-6}$ cycloalkyl, $NHCOC_{1-10}$, $NHCOC_{3-10}$ cycloalkylamine, $NHCOC_{1-10}$ aminophenyl, $NHCOC_{1-6}$ heteroarylamine, $NHCOC_{1-6}$ alkylcarboxylate, $NHCOC_{1-6}$ cycloalkylcarboxylate, $NHCOC_{1-6}$ heteroarylcarboxylate;

$L^1$ is —$NR^4$—$R^1$;

$R^4$ is H; and $R^1$ is:

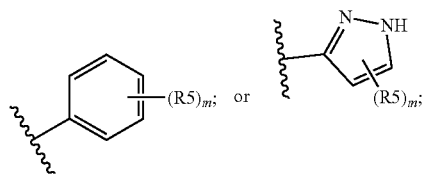

wherein:
(i) each R5 is independently Br, F, COOH, $CH_2COOH$, NHCOalkenyl, NHC(O)$C_{1-6}$ alkenyl, NHCOalkenyl$(C_{1-6}$alkyl$)N(C_{1-10}$ alkyl$)_2$, $CH_2CONHalkenyl$, $CH_2NHCOalkenyl$ $CH_2$- phenyl, $C_{3-6}$ alkylamine, $C_{3-6}$ cycloalkylamine, $C_{3-6}$ alkylcarboxylate, $C_{3-6}$ cycloalkylcarboxylate or phenyl; or (ii) each R5 is independently:

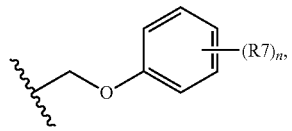
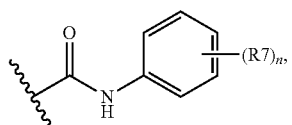
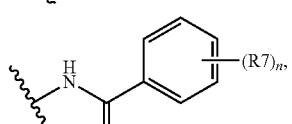
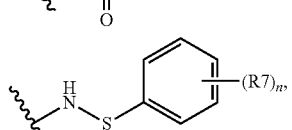
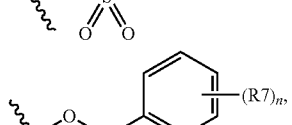
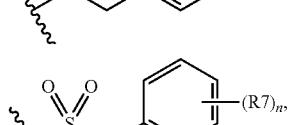
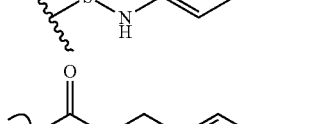
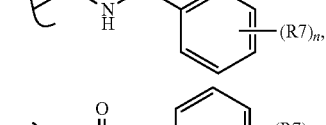
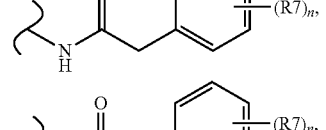
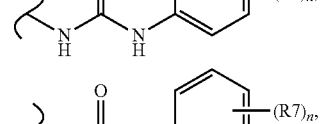
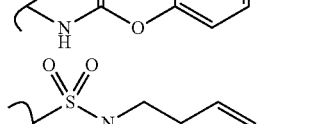
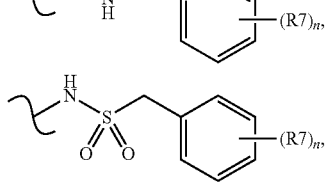
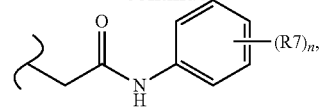
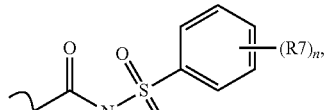
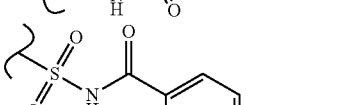
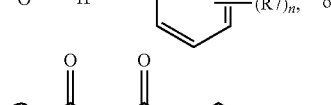

each R7 is independently H, halo, CN, $NO_2$, $C_{1-10}$ alkyl, $C_{1-10}$ haloalkyl, $C_{2-10}$ alkenyl, $C_{2-10}$ alkynyl, $C(O)C_{1-6}$ alkyl, $C(O)NHC_{1-6}$ alkyl, $NH_2$, $NHC_{1-10}$ alkyl, $N(C_{1-10}$ alkyl$)_2$, $NHC(O)$ $C_{1-6}$ alkyl, $NHC(O)C_{1-6}$ alkenyl, NHCOalkenyl, $NHC(O)C_{1-6}$ alkenyl, NHCOalkenyl($C_{1-6}$ alkyl)$N(C_{1-10}$ alkyl$)_2$, $NHS(O)_2C_{1-10}$ alkyl, OH, $OC_{1-10}$ alkyl, $OC_{1-10}$ haloalkyl, SH, $SC_{1-10}$ alkyl, $S(O)C_{1-6}$ alkyl, $S(O)_2NHC_{1-6}$ alkyl, $C_{3-10}$ cycloalkyl, $C_{4-10}$ cycloalkenyl, a monocyclic 3- to 8-membered ring, or a bicyclic 6- to 12-membered ring;

wherein each monocyclic 3- to 8-membered ring or bicyclic 6- to 12-membered ring is fully saturated, partially unsaturated, or fully unsaturated;

wherein each monocyclic 3- to 8-membered ring independently contains carbon atoms and optionally and independently contains 1, 2, or 3 heteroatoms independently selected from the group consisting of N, O, and S;

wherein each bicyclic 6- to 12-membered ring independently contains carbon atoms and optionally and independently contains 1, 2, 3, 4, 5, or 6 heteroatoms independently selected from the group consisting of N, O, and S;

wherein each $C_{1-10}$ alkyl, $C_{2-10}$ alkenyl, $C_{2-10}$ alkynyl, $NHC_{1-10}$ alkyl, $N(C_{1-10}$ alkyl$)_2$, $OC_{1-10}$ alkyl, and $SC_{1-10}$ alkyl is optionally and independently substituted with 1, 2, 3, 4, or 5 substituents independently selected from the group consisting of halo, CN, $NO_2$, $CH_2$-phenyl, $NH_2$, $NHC_{1-10}$ alkyl, $N(C_{1-10}$alkyl$)_2$, OH, $OC_{1-6}$alkyl, $OC_{1-10}$ haloalkyl, =O, $C_{3-6}$ cycloalkyl, phenyl, and a multicyclic ring system;

wherein each $C_{3-10}$ cycloalkyl, $C_{4-10}$ cycloalkenyl, monocyclic 3- to 8-membered ring, or bicyclic 6- to 12-membered ring is optionally and independently substituted with 1, 2, 3, 4, or 5 substituents independently selected from the group consisting of halo, CN, $NO_2$, $CH_2$-phenyl, $NH_2$, $NHC_{1-10}$ alkyl, $N(C_{1-10}$alkyl$)_2$, OH, OC$_{1-6}$alkyl, OC$_{1-10}$ haloalkyl, =O, C$_{3-6}$ cycloalkyl, phenyl, and a multicyclic ring system; and wherein each multicyclic ring system contains at least one nonaromatic ring and at least one aromatic ring; or wherein each multicyclic ring system contains at least one heteroaromatic ring;

wherein each m is independently 1, 2, 3, 4, or 5;

wherein each n is independently 1, 2, 3, 4, or 5; and

L$^2$ is H or NH$_2$.

The following exemplary compounds of Formula (I-2) and pharmaceutically acceptable salts thereof are disclosed:

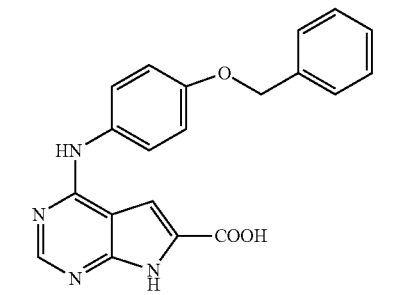

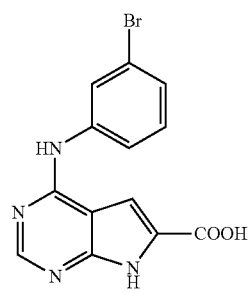

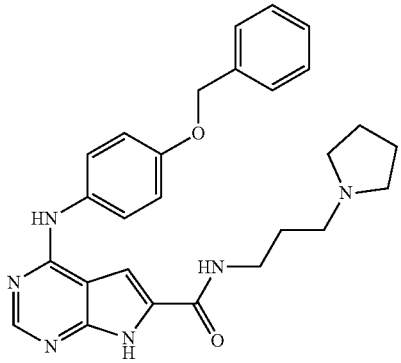

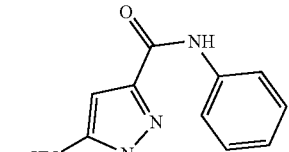

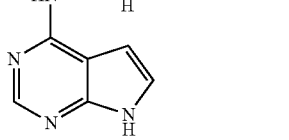

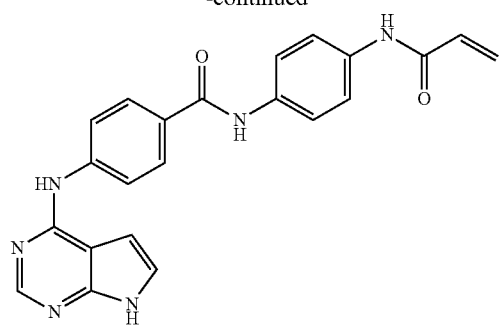

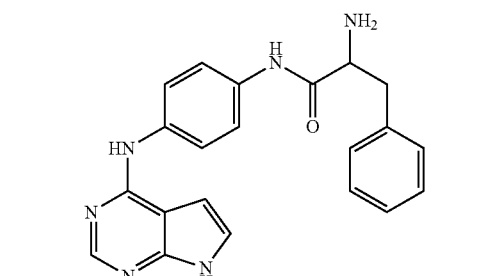

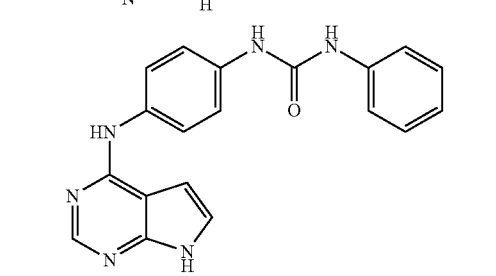

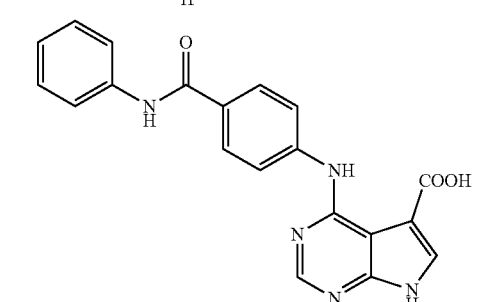

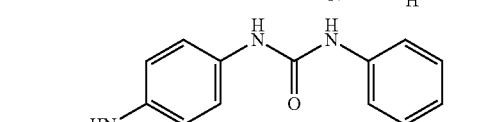

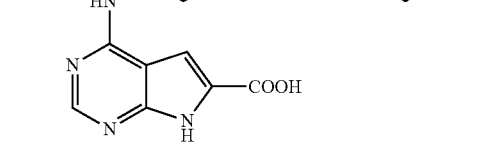

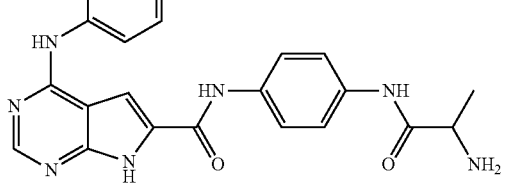

45
-continued
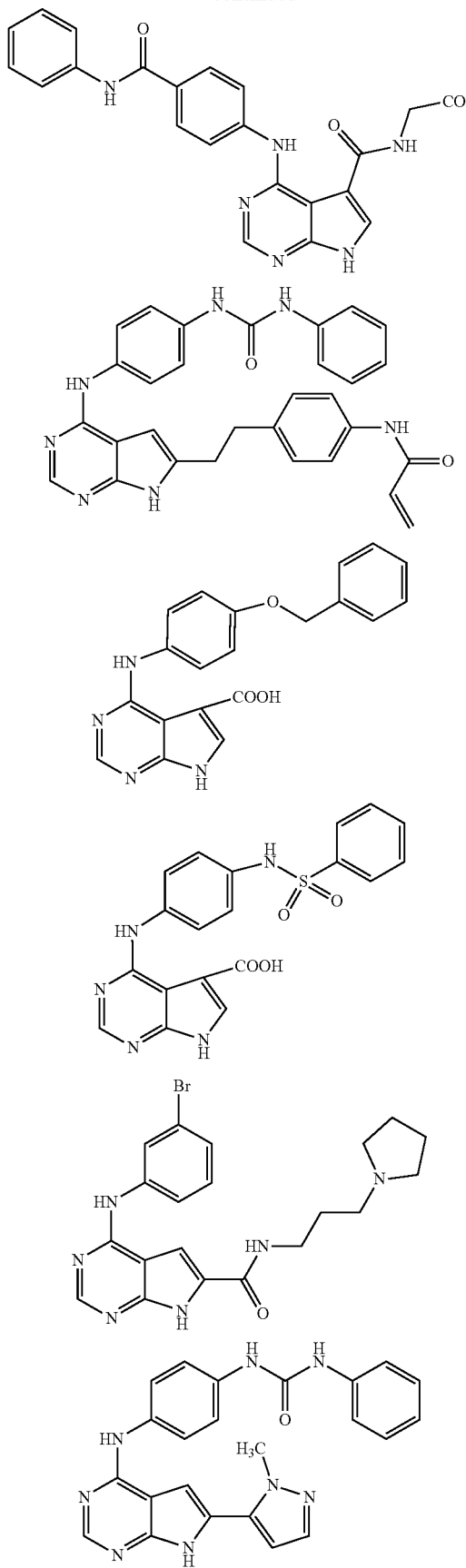
46
-continued
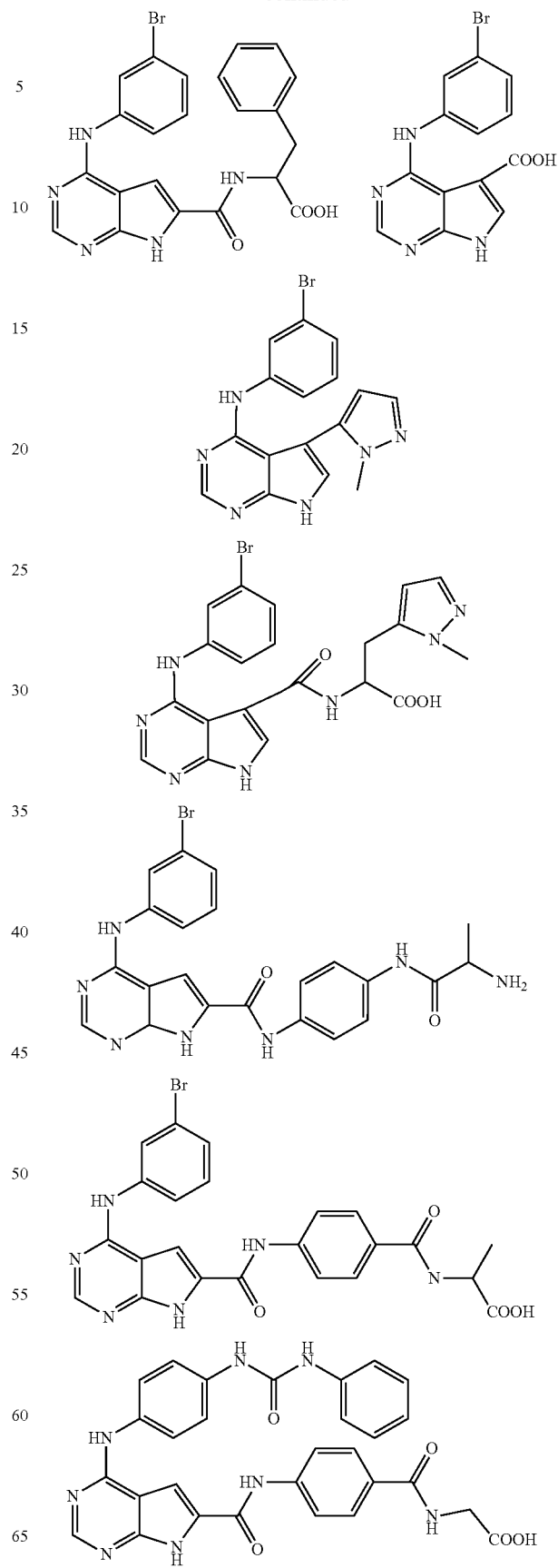

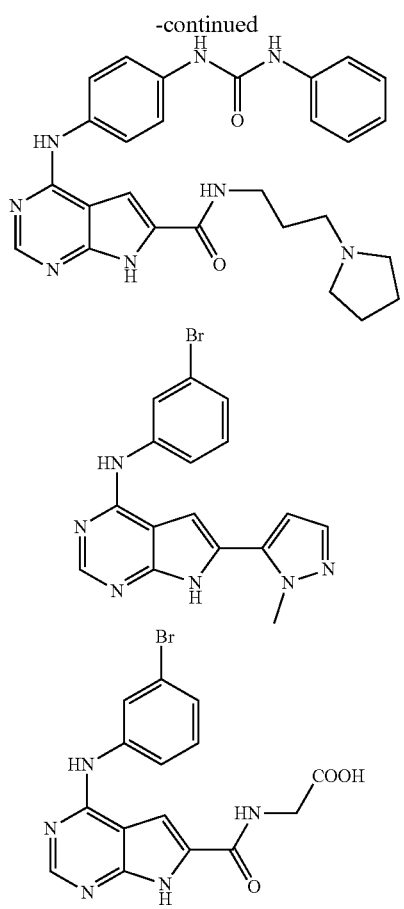

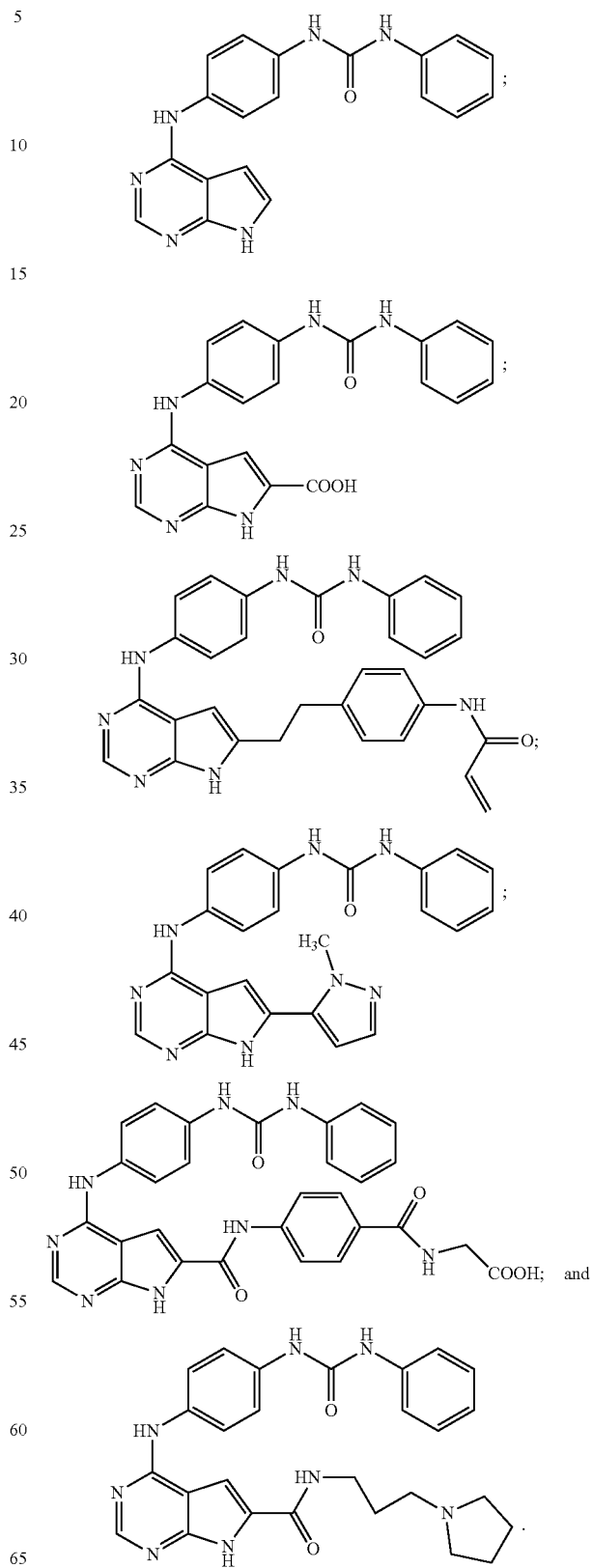

The compounds of Formula (I-2) including the compounds set forth above, are dual-targeted mutant EGFR and aurora kinase inhibitors that are effective in cancers with dysfunctional RAS-RAF-MEK pathways. These include mutant EGFR and mutant KRAS driven cancers. The compounds are effective in overcoming resistance to approved ATP-competitive EGFR inhibitors due to the dual-targeted mutant EGFR and aurora kinase mechanism of inhibition and are effective in cancers with aberrant BIM, c-Myc and FoxM1 signaling and in retinoblastoma-deficient cancers due to aurora kinase inhibition.

In some embodiments of the compounds of Formula (I-2):
L$^1$ is —NH—R$^1$,
wherein R$^1$ is Br or

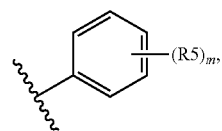

wherein R5 is

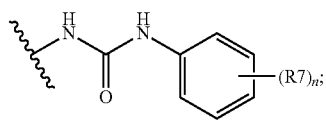

and
wherein R7 is H and N=1.

Examples of such embodiments, include, but are not limited to, the following compounds:

Of course, the compound of Formula (I-2) can also be a pharmaceutically acceptable salt of the exemplary compounds set forth above.

In other embodiments of the compounds of Formula (I-2):

L² is H,

X⁴ is CR² and R² is COOH, and/or

X⁵ is CCOOH.

These embodiments can be described as having a carboxylic acid group in the X4 position (pendent X⁴) or the X⁵ position (pendent X⁵). Likewise, although not illustrated above but claimed in Formula (I-2) a carboxylic acid group can also be incorporated into the CX⁷R⁸ pendant X⁵ to create polarity and/or ionic character for targeting purposes.

In many such embodiments, the compound of Formula (I-2) has a carboxylic acid in the X⁴ position or the X⁵ position and:

L¹ is —NH—R¹, wherein R¹ is Br or

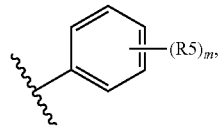

wherein R5 is independently:

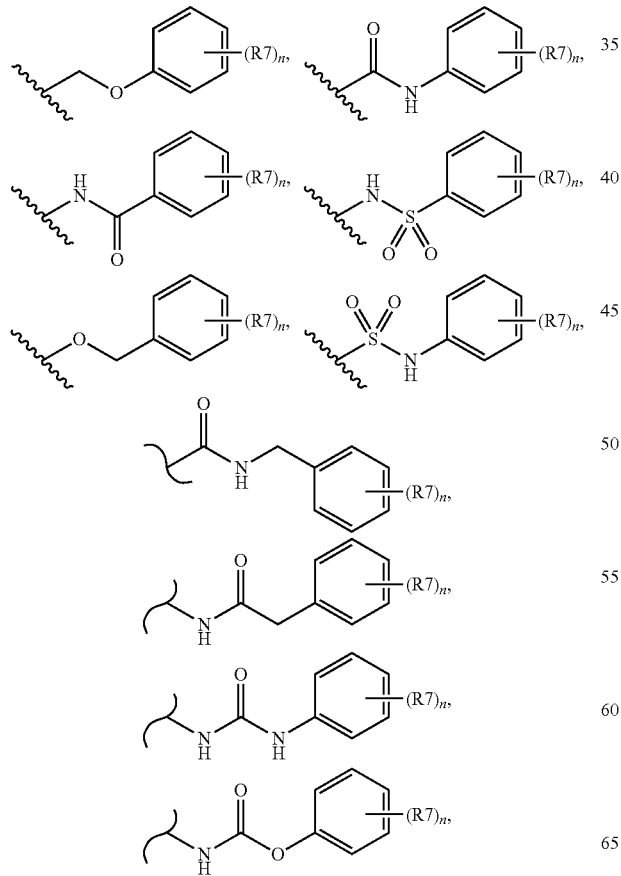

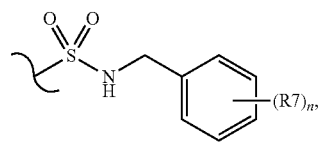

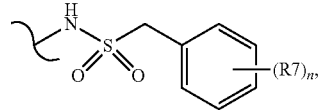

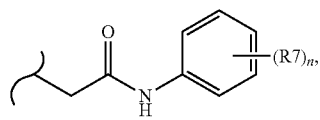

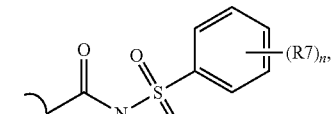

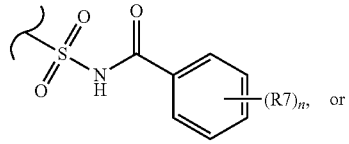

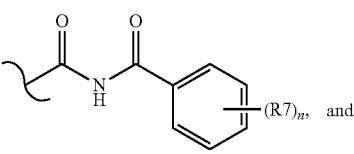

wherein each R7 is independently H and m is 1.

In many such embodiments, X⁴ is CR², R² is COOH, and X⁵ is CH. Examples of such exemplary embodiments of the compound of Formula (I-2), include, but are not limited to, the following compounds:

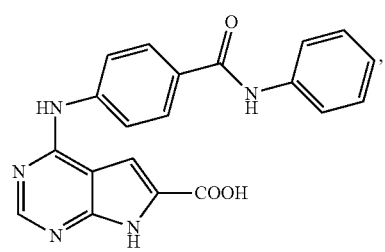

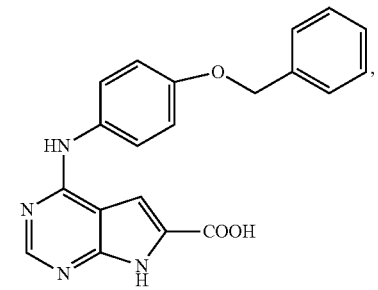

-continued

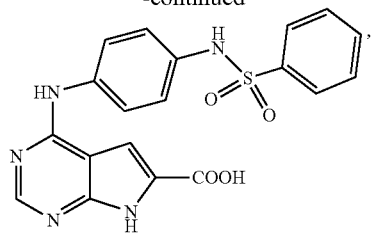

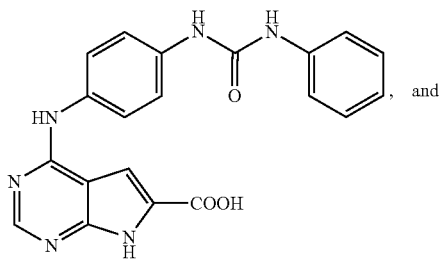

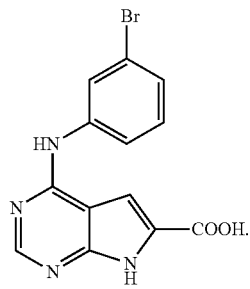

Of course, the compound of Formula (I-2) can also be a pharmaceutically acceptable salt of the exemplary compounds set forth above.

As a first example, the following compound:

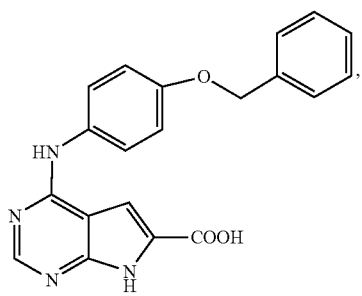

(I-2-1)

which is illustrated in the examples above, can be referred to as Compound (I-2-1) and is discussed from a functional perspective immediately below.

Compound (I-2-1) is a mutant EGFR and AURKB inhibitor. In this embodiment, the $L^1$ is —NH—$R^1$, $R^1$ is phenyl-$R^5$, and $R^5$ is a benzyloxy side chain ($C_6H_5CH_2O$—) that binds with the alpha C-helix out pocket, and $X^4$ is $CR^2$ and $R^2$ is COOH (a carboxylic acid group) that interacts with the hinge region of AURKB and mutant EGFR. A relatively large $L^1$ substitution due to the benzyloxy sidechain at $R^5$ of the $R^1$ phenyl reduces AURKA binding and drives a preference for AURKB. This translates to an increase in potency for mutant KRAS and mutant EGFR. Similar larger substitutions at $L^1$ as defined by Formula (I-2) are adopted at R7 through different alkyl, aryl and heteroaryl sidechains for interactions within the alpha helix out pocket of EGFR and AURKB to drive potency. The COOH at $R^2$ of X4 as defined by Formula (I-2) is well tolerated within mutant EGFR and interact through hydrogen bonds to residues close to the hinge region of EGFR.

As a second example, the following compound:

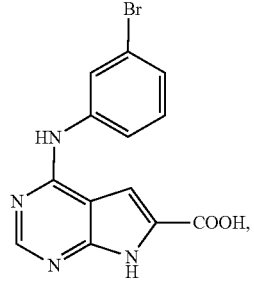

(I-2-2)

which is illustrated in the examples above, can be referred to as Compound (I-2-2) and is discussed from a functional perspective immediately below.

Compound (I-2-2) is a dual-targeted mutant EGFR and AURKA inhibitor that binds to mutant EGFR in a Type I mode of binding. In this example, the $L^1$ is —NH—$R^1$ and $R^1$ is 3-bromophenyl, and the $X^4$ is $CR^2$ and $R^2$ is COOH (a carboxylic acid group) that interacts with an arginine residue in AURKA through an ionic bond. The COOH substitution at $R^2$ interacts ionically with arginine 137 and drives selectivity for AURKA over AURKB.

Figure 15:
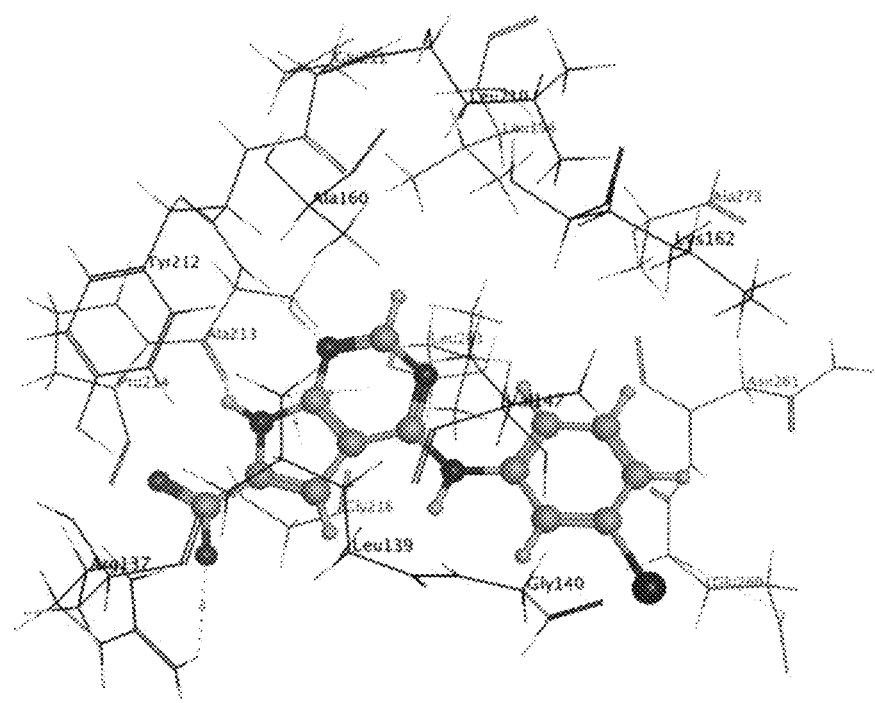
FIG. 15 is another representation of a chemical structure illustrating a non-limiting embodiment of the compound in a binding pocket.
Figure 16:
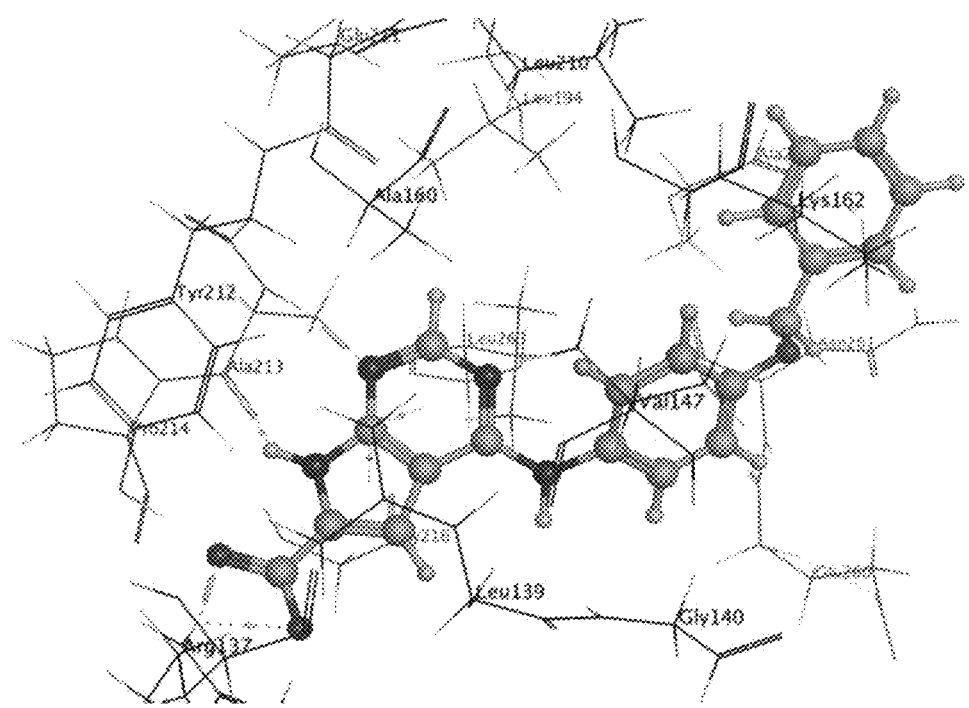
FIG. 16 is another representation of a chemical structure illustrating a non-limiting embodiment of the compound in a binding pocket.
Figure 17:
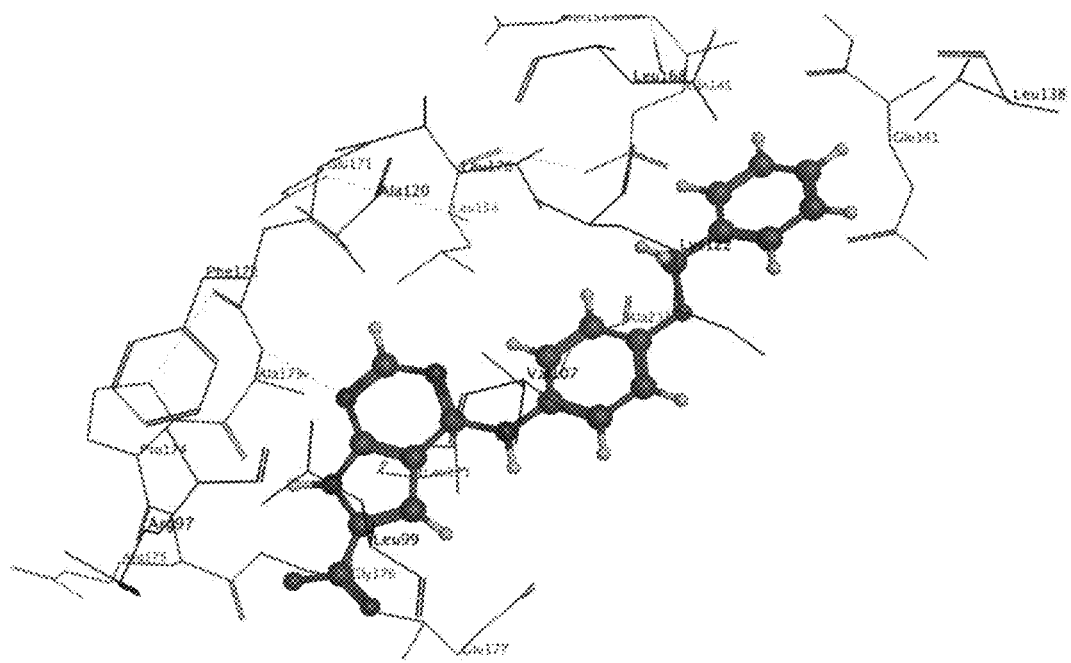
FIG. 17 is another representation of a chemical structure illustrating a non-limiting embodiment of the compound in a binding pocket.

FIGS. 15-17 illustrate interactions of Compounds (I-2-1) and (I-2-2) with AURKA and AURKB. FIG. 15 illustrates the interactions for Compound (I-2-2) within AURKA. Interactions are observed with the hinge region residues Ala213. The L1 substitution is accommodated well within AURKA and the COOH as pendent X4 interacts with Arg 137 of AURKA. FIG. 16 shows the interactions for Compound (I-2-1) within AURKA. Interactions are observed with the hinge region residues Ala213. The L1 substitution is accommodated within the back pocket of AURKA, however the pocket is much smaller in AURKA compared to AURKB. The L1 substitution in Compound (I-2-1) is in an opposite orientation compared to Compound (I-2-2) (FIG. 15) within AURKA. The COOH as pendent X4 in Compound (I-2-1) interacts with Arg 137 of AURKA similar to I-2-2.

FIG. 17 shows the interactions for Compound (I-2-1) within AURKB. Interactions are observed with the hinge region residues Ala173. The L1 substitution is accommodated well within the back pocket of AURKB. The back pocket is larger for AURKB compared to AURKA. The COOH as pendent X4 is in close proximity to Arg 175 of AURKB.

In other embodiments of the compounds of Formula (I-2) $X^4$ is $CR^2$, $R^2$ is H, and $X^5$ is CCOOH. Examples of such embodiments, include, but are not limited to, the following compounds:

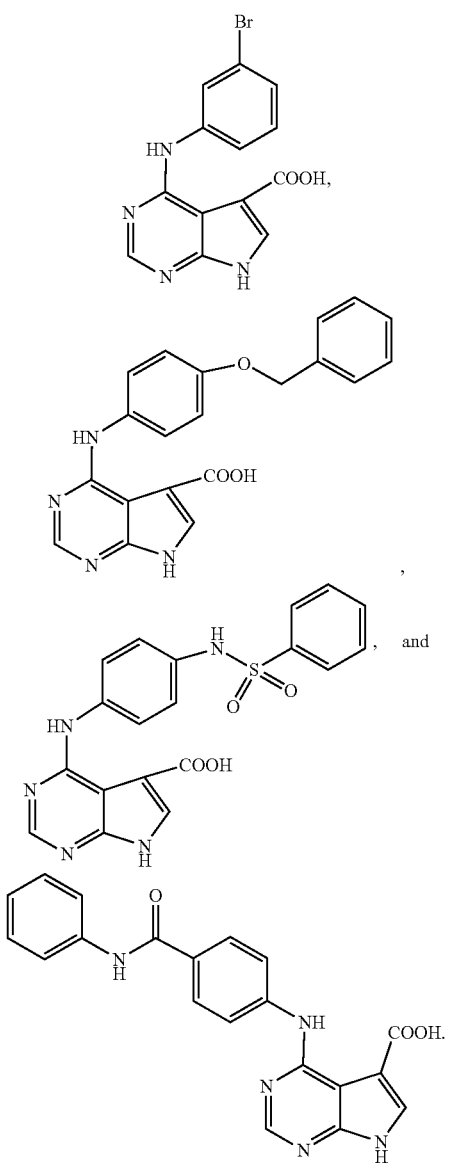

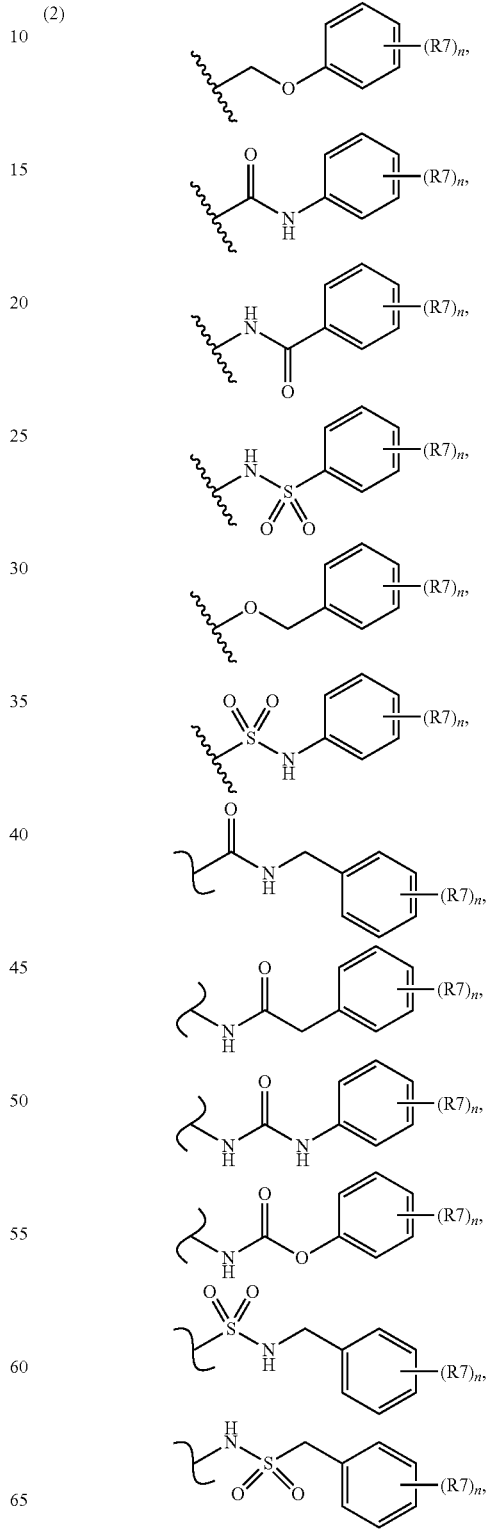

Of course, the compound of Formula (I-2) can also be a pharmaceutically acceptable salt of the exemplary compounds set forth above.

From a functional perspective, the compounds illustrated above have a COOH (a carboxylic acid group) pendent group at $X^5$ that controls the orientation and positioning of the $L^1$ substitution within the back pocket of mEGFR, AURKA and AURKB. By controlling the orientation of the $L^1$ substitution with a carboxylic acid group pendent $X^5$, the compounds illustrated above have a fixed mode of binding within EGFR, AURKA and AURKB. The carboxylic acid group at $X^5$ is a polar substitution that allows for additional polar interactions within the ATP pocket and improves water solubility of the compound. Additional polar substitutions such as a heteroarylamines, alkylamines and cycloalkylamines at $X^5$ where $X^5$ is $CX^7R^8$, allow for interactions with polar residues such as serine 797 and aspartate 800 in the front pocket of the ATP site of mutant EGFR. The substitutions at $X^5$ are well tolerated within AURKA and AURKB and occupy the same front pocket as EGFR allowing for dual EGFR and AURK inhibition. The $X^5$ substitution includes hydrophilic groups that balance out the hydrophobic properties of the parent compound and provide optimal properties for oral bioavailability.

In still other embodiments of the compounds of Formula (I-2) can be further defined wherein $R^5$ is selected from:

(1) Br, Cl, or COOH; or

55
-continued

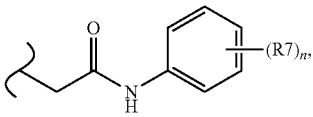

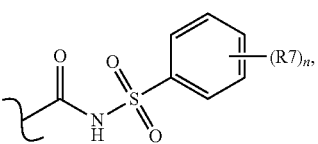

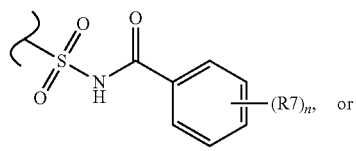

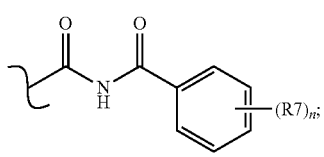

wherein each R7 is independently H, halo, CN, $NO_2$, $C_{1-10}$ alkyl, $C_{1-10}$ haloalkyl, $C_{2-10}$ alkenyl, $C_{2-10}$ alkynyl, $C(O)C_{1-6}$ alkyl, $C(O)NHC_{1-6}$ alkyl, $NH_2$, $NHC_{1-10}$ alkyl, $N(C_{1-10}$ alkyl$)_2$, $NHC(O)C_{1-6}$ alkyl, $NHC(O)C_{1-6}$ alkenyl, $NHS(O)_2C_{1-10}$ alkyl, OH, $OC_{1-10}$ alkyl, $OC_{1-10}$ haloalkyl, SH, $SC_{1-10}$ alkyl, $S(O)C_{1-6}$ alkyl, $S(O)_2NHC_{1-6}$ alkyl, $C_{3-10}$ cycloalkyl, $C_{4-10}$ cycloalkenyl, a monocyclic 3- to 8-membered ring, or a bicyclic 6- to 12-membered ring. In such embodiments, n is independently 1, 2, 3, 4, or 5. In these embodiments, $X^4$ is CR2, R2 is H, $X^5$ is CH, and $L^2$ is H. Varied substitutions can be adopted at $R^7$ of $L^1$ as defined by Formula (I-2) to optimize positioning in the back pocket and interactions with Lys 745 and Asp 855 in the alpha C-helix out pocket of mutant EGFR.

In many such embodiments, each R7 is H, halo, CN, $NO_2$, $C_{1-10}$ alkyl, O $C_{1-10}$ alkyl, NHCOalkenyl, $NHC(O)C_{1-6}$ alkenyl, or an NHCOalkenyl($C_{1-6}$alkyl)N($C_{1-10}$alkyl)$_2$. Examples of such exemplary embodiments, include, but are not limited to, the following compounds:

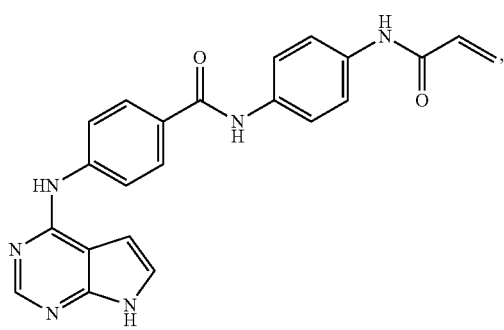

56
-continued

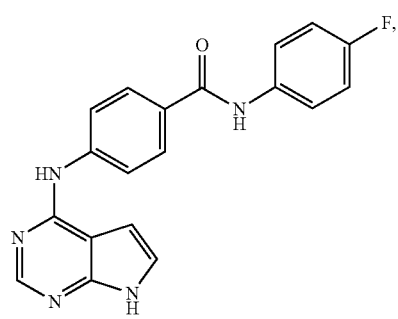

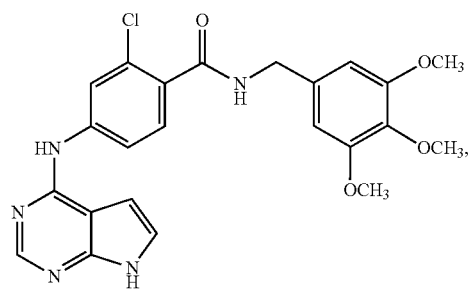

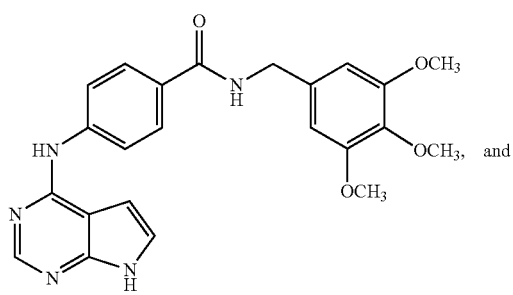

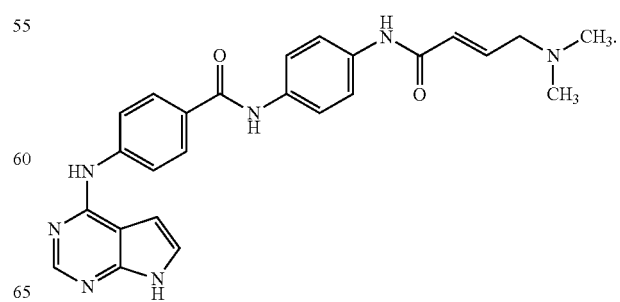

As an example, the following compounds:

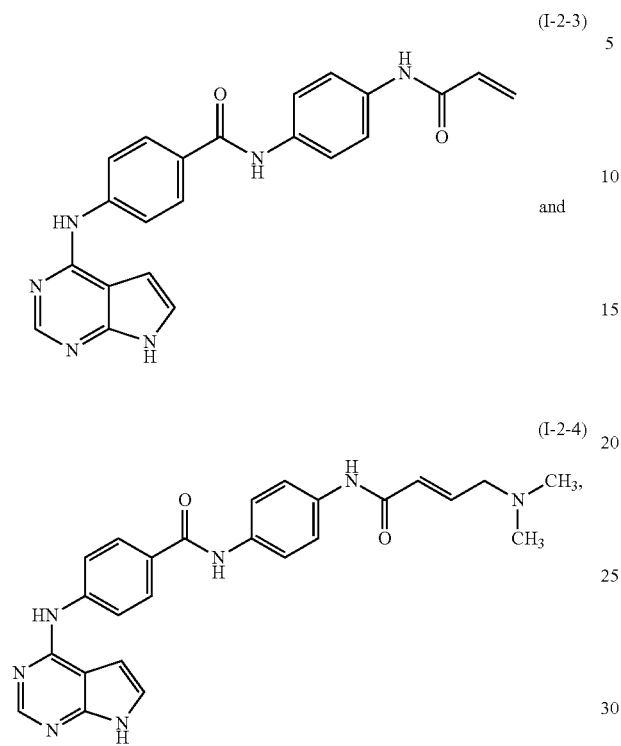

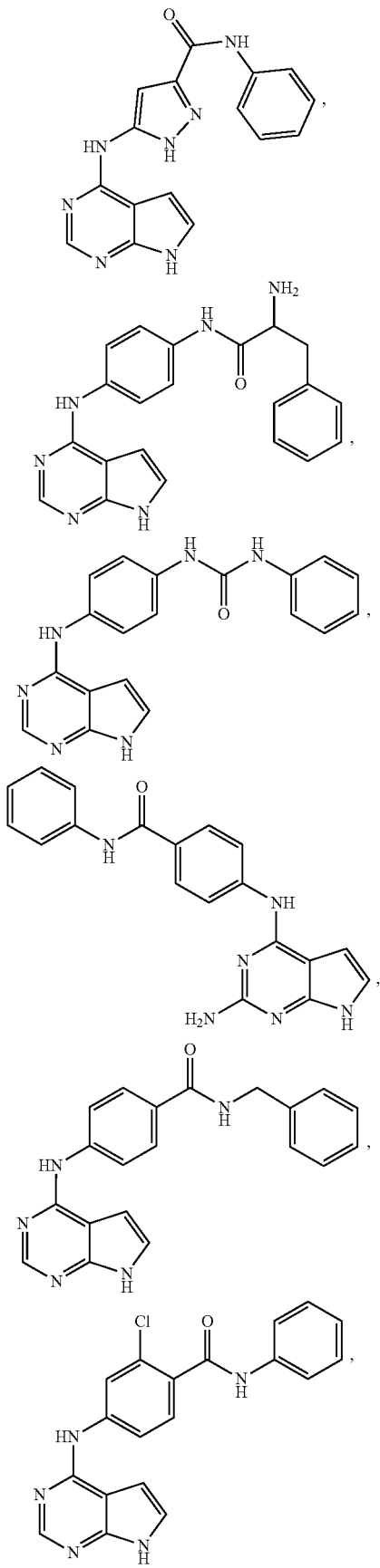

which are illustrated in the examples above, can be referred to as Compound (I-2-3) and Compound (I-2-4), respectively, and are discussed from a functional perspective immediately below.

Compound (I-2-3) is developed as an irreversible mutant EGFR inhibitor that incorporates a Michael acceptor as part of its sidechain. Compound (I-2-3) binds to mutant EGFR through a covalent bond with a cysteine residue (Cys 797) in the front pocket. In this embodiment, $R^7$ is an acrylamide. In this particular example, the structure of R7 can be described as NHCOalkenyl. In this example, the acrylamide improves mutant EGFR inhibition with Compound (I-2-3) while being tolerated in aurora kinases A and B. Compound (I-2-3) demonstrates sub-micromolar potency in mutant EGFR expressing cells (0.033 micromolar). In additional examples include R7 can be an acrylamide with pendant $C_{1-6}$ alkylamine, such as Compound (I-2-4) above. In this additional example, the structure of R7 can be described as a NHCOalkenyl($C_{1-6}$alkyl)N($C_{1-10}$ alkyl)$_2$. The acrylamide will form a covalent bond with cysteine 797 while the alkylamines will allow for additional ionic bonds and hydrogen bonds with Asp 800 in the front pocket. A common mutation in the front pocket is a cysteine to serine replacement (C797S). The dual targeted EGFR and AURK inhibition will reduce the development of the C797S mutation, and the presence of pendant $C_{1-6}$ alkylamines in the side chain will allow for ionic and hydrogen bonding in the front pocket despite the loss of a covalent bond.

In further embodiments of the compounds of Formula (I-2), each $R^7$ is H and N=1. Examples of such embodiments, include, but are not limited to, the following compounds:

-continued

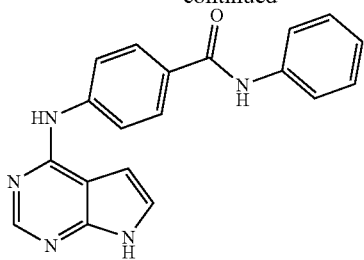

, and

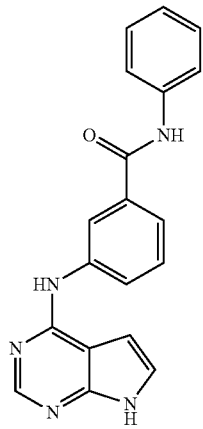

As a first example, the following compound:

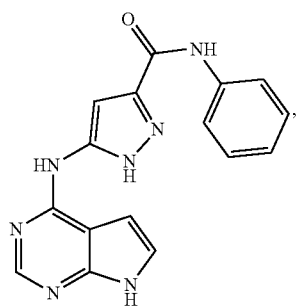

(I-2-5)

which is illustrated in the examples above, can be referred to as Compound (I-2-5) and is discussed from a functional perspective immediately below.

Compound (I-2-5) is a dual AURKA and AURKB inhibitor that incorporates a polar sidechain that allows for improved cell penetration. This translates to submicromolar effects in mutant KRAS positive NSCLC and mutant EGFR-positive NSCLC cells.

As a second and third examples, the following compounds:

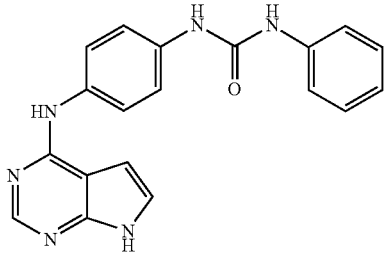

(I-2-6)

and

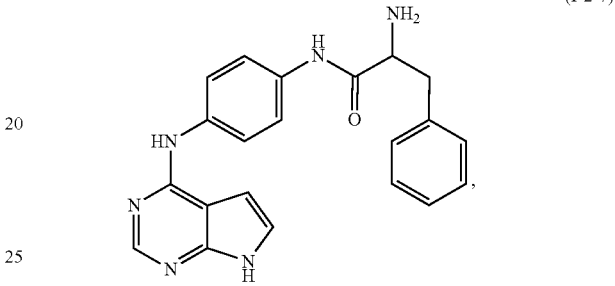

(I-2-7)

which are illustrated in the examples above, can be referred to as compound (I-2-6) and compound (I-2-7), respectively, and are discussed from a functional perspective immediately below.

Compounds (I-2-6) and (I-2-7) incorporate spacers and polar substitutions such as the —NHCO— spacer shown above to optimize interactions with Lys 745 and Asp 855 in the alpha C-helix out pocket of mutant EGFR. A similar improvement is observed within aurora kinase B which also adopts a conformation similar to the alpha C-helix out conformation of mutant EGFR.

In still other embodiments of the compound of Formula (I-2), $X^4$ is $X^6R^3$. In these embodiments, $X^6$ is $CONH(CH)_m$, $NHCO(CH)_m$, $CH_2CH_2$, C≡C, C=C, $CH_2$, S, $NH(CH)_m$, or COO. In these embodiments, $R^3$ is a 5-membered heteroaryl, 6-membered heteroaryl, or substituted phenyl. The 5-membered or 6-membered heteroaryl contains 1 N heteroatom and 1-3 additional heteroatoms selected from the group consisting of N, O, and S, and is optionally substituted with 1, 2, or 3 substituents independently selected from the group consisting of halo, $C_{1-6}$ alkyl, $C_{1-6}$ haloalkyl, $C_{1-6}$ alkylamino, $C_{1-6}$ cycloalkylamino, $NH_2$, $NHC_{1-10}$ alkyl, $NHC_{1-10}$ aryl, $NHC_{1-10}$ alkenyl, $NHC_{1-10}$ alkynyl $N(C_{1-10}$ alkyl$)_2$, OH, COOH, $CH_2COOH$, $OC_{1-6}$ alkyl, $OC_{1-6}$ haloalkyl, $C_{3-6}$ cycloalkyl, and phenyl, $CONHC_{1-10}$, CONHalkyl, $CONH(C_{1-10}$ alkyl$)_2$, CONHalkenyl, CONHalkenyl($C_{1-6}$ alky)N($C_{1-10}$ alkyl$)_2$, $CH_2CONHalkenyl$, $CONHC_{1-6}$ cycloalkyl, $CONHC_{1-10}$, $CONHC_{3-6}$ cycloalkylamine, $CONHC_{3-6}$ aminophenyl, $CONHC_{1-6}$ heteroarylamine, $CONHC_{1-6}$ alkylcarboxylate, $CONHC_{1-6}$ cycloalkylcarboxylate, $CONHC_{1-6}$ heteroarylcarboxylate, $CONHC_{1-6}$ phenylcarboxylate, $NHCOC_{1-10}$ NHCOalkyl, $NHCO(C_{1-10}$ alkyl$)_2$, NHCOalkenyl, NHCOalkenyl($C_{1-6}$alkyl)N($C_{1-10}$ alkyl$)_2$, $CH_2NHCOalkenyl$, $NHCOC_{1-6}$ cycloalkyl, $NHCOC_{1-10}$, $NHCOC_{3-10}$ cycloalkylamine, $NHCOC_{1-10}$ aminophenyl, $NHCOC_{1-6}$ heteroarylamine, $NHCOC_{1-6}$ alkylcarboxylate, $NHCOC_{1-6}$ cycloalkylcarboxylate, $NHCOC_{1-6}$ heteroarylcarboxylate. The phenyl is optionally substituted with 1, 2, or 3 substituents independently selected from the group consisting of halo, $C_{1-6}$ alkyl, $C_{1-6}$ haloalkyl, $C_{1-6}$ alkylamino, $C_{1-6}$ cycloalkylamino, $NH_2$, $NHC_{1-10}$ alkyl, $NHC_{1-10}$ aryl, $NHC_{1-10}$ alkenyl, $NHC_{1-10}$ alkynyl $N(C_{1-10}$ alkyl$)_2$, OH, COOH, $CH_2COOH$, $OC_{1-6}$ alkyl, $OC_{1-6}$ haloalkyl, $C_{3-6}$ cycloalkyl, and phenyl, $CONHC_{1-10}$, CONHalkyl, $CONH(C_{1-10} alkyl)_2$, CONHalkenyl, $CH_2CONHalkenyl$, $CONHC_{1-6}$ cycloalkyl, $CONHC_{1-10}$, $CONHC_{3-6}$ cycloalkylamine, $CONHC_{3-6}$ aminophenyl, $CONHC_{1-6}$ heteroarylamine, $CONHC_{1-6}$ alkylcarboxylate, $CONHC_{1-6}$ cycloalkylcarboxylate, $CONHC_{1-6}$ heteroarylcarboxylate, $CONHC_{1-6}$ phenylcarboxylate, $NHCOC_{1-10}$ NHCOalkyl, $NHCO(C_{1-10} alkyl)_2$, NHCOalkenyl, $NHCOalkenyl(C_{1-6}alkyl)N(C_{1-10}$ $alkyl)_2$, $CH_2NHCOalkenyl$, $NHCOC_{1-6}$ cycloalkyl, $NHCOC_{1-10}$, $NHCOC_{3-10}$ cycloalkylamine, $NHCOC_{1-10}$ aminophenyl, $NHCOC_{1-6}$ heteroarylamine, $NHCOC_{1-6}$ alkylcarboxylate, $NHCOC_{1-6}$ cycloalkylcarboxylate, $NHCOC_{1-6}$ heteroarylcarboxylate. Each m is independently 1, 2, 3, 4, or 5. An example of this embodiment, include, but are not limited to, the following compound:

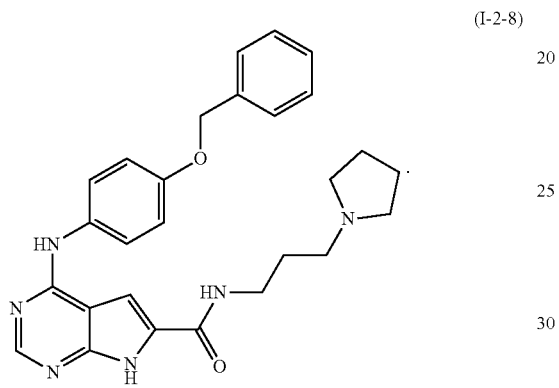

(I-2-8)

Further examples of this embodiment include analogs of Compound (I-2-8) including, but not limited to, the following compounds:

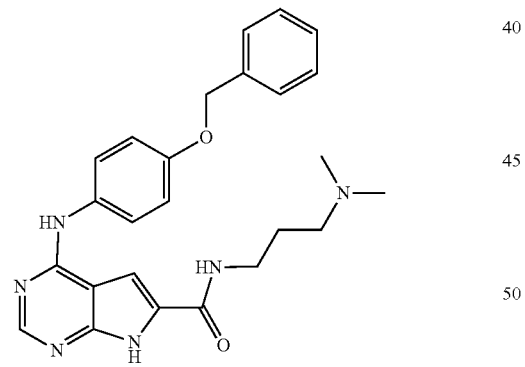

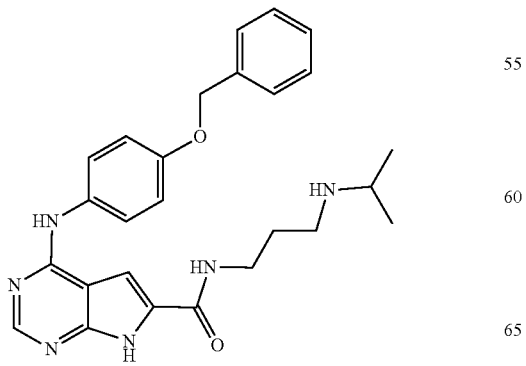

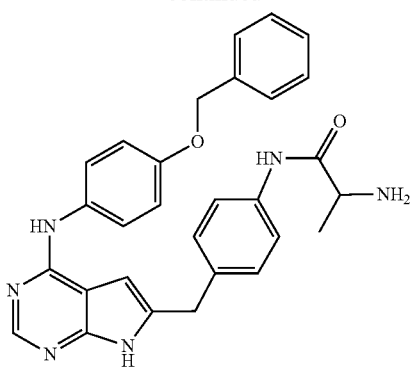

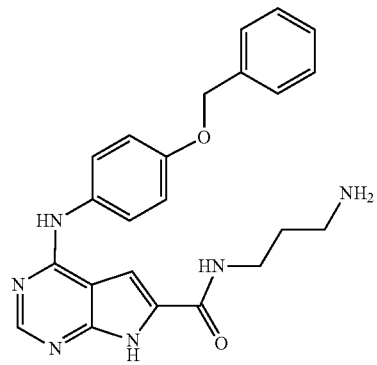

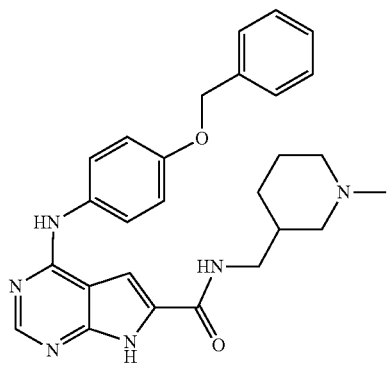

63
-continued

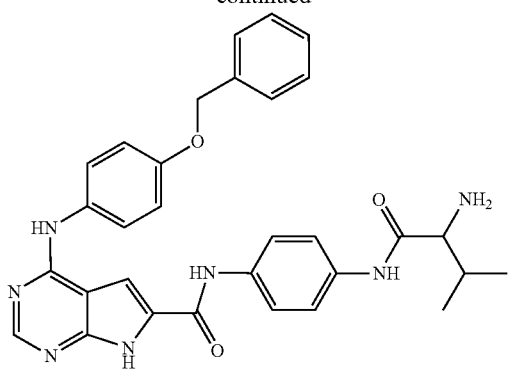

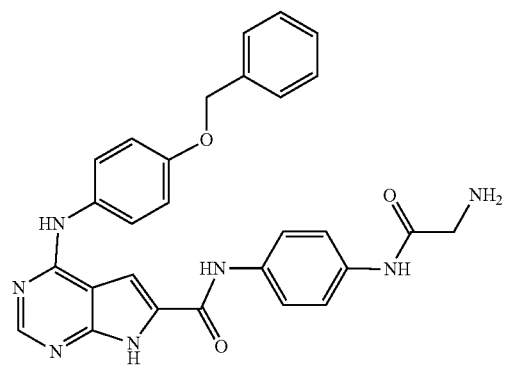

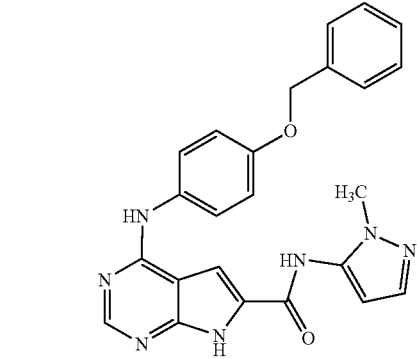

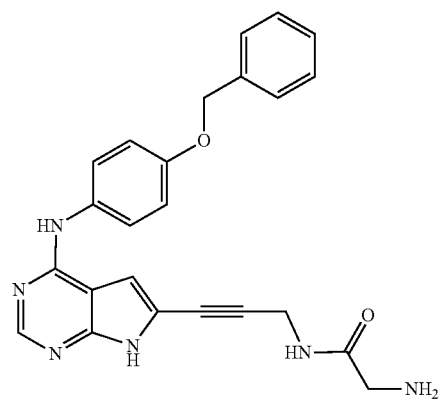

64
-continued

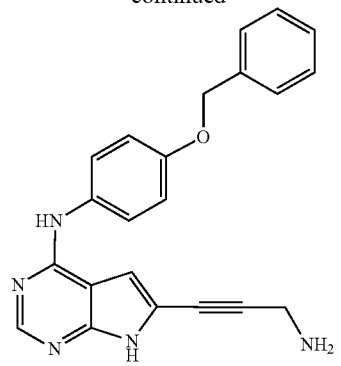

From a functional perspective, Compound (I-2-8) is a nanomolar, dual-targeted mutant EGFR and AURKB inhibitor with demonstrated anticancer effects in mutant KRAS positive non-small cell lung cancer, mutant EGFR positive non-small cell lung cancer, and multiple cancer cells with aberrant RAS-RAF-MEK pathways including melanoma, renal cancer, breast cancer and CNS tumors. The pyrrolidinyl moiety at the end of the $X^6R^3$ pendent group is appropriately spaced and positioned to interact with an aspartate residue (Asp 800) in the front pocket of mutant EGFR and also interact within the front pocket of AURKB. The amide and the three carbon spacer at $X^6R^3$ provides the optimal orientation and flexibility for the pyrrolidinyl moiety to interact within the front pocket. The pyrrolidinyl moiety is a polar functional group that improves aqueous solubility and improves transport in to cancer cells. Additional analogs with polar substitutions at $X^6R^3$ such as a heteroarylamines, alkylamines and cycloalkylamines are being developed to optimize interactions with polar residues such as serine 797 and aspartate 800 in the front pocket of the ATP site of mutant EGFR. Varied linker lengths (e.g. 3 carbons in the case of Compound (I-2-8)) can be adopted to appropriately orient the polar functional group for additional polar interactions that drive potency and provide optimal properties for cell penetration and oral bioavailability.

In some embodiments of the compound of Formula (I-2) R5 is Br. One non-limiting example is the following compound:

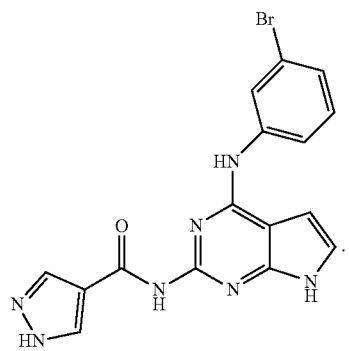 [SMILES: O=C(Nc1nc(Nc2cccc(Br)c2)c2cc[nH]c2n1)c1cn[nH]c1]
In still other embodiments of the compound of Formula (I-2) R5 is Br and $L^2$ is H. Examples of such exemplary embodiments, include, but are not limited to, the following compounds:
In still other embodiments of the compound of Formula (I-2) R5 is Br, L2 is H, and $X^5$ is CH. Examples of such embodiments, include, but are not limited to, the following compounds:
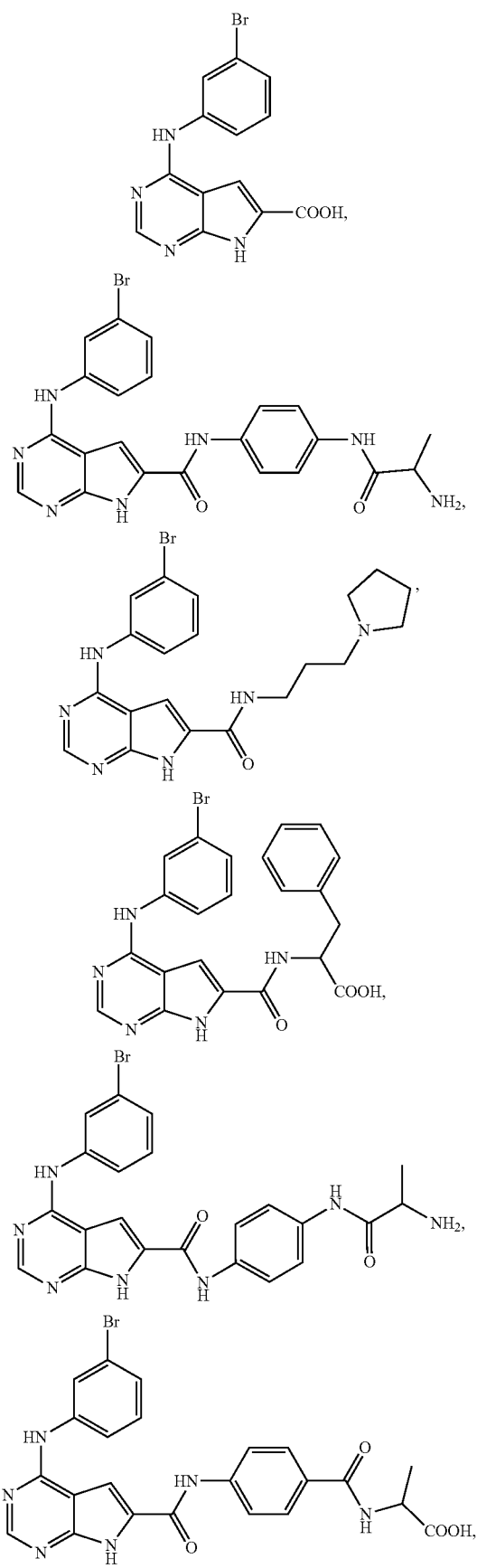

-continued

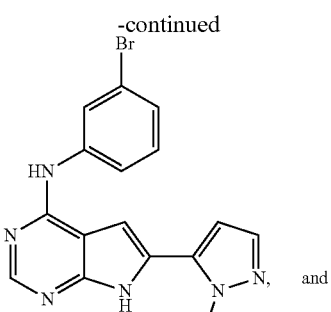

and

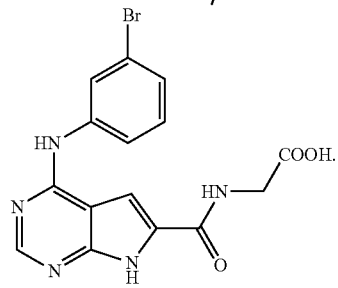

In some exemplary embodiments, the compound is a compound of Formula (I-3):

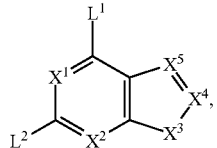
(I-3)

or a pharmaceutically acceptable salt thereof;
wherein:
$X^1$ is N;
$X^2$ is N;
$X^3$ is —NH—;
$X^4$ is CH or COOH;
$X^5$ is CH or COOH;
$L^1$ is —NH—$R^1$;
$R^1$ is:
Br;

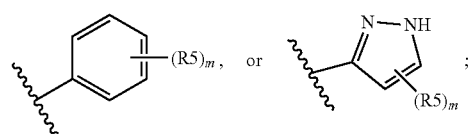

$R^5$ is:

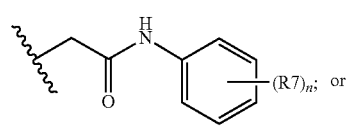

-continued

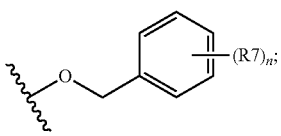

$R^7$ is H or NHC(O)CHCH$_2$; and
$L^2$ is H.

Examples of such embodiments of compounds of Formula (I-3), include, but are not limited to, the following compounds:

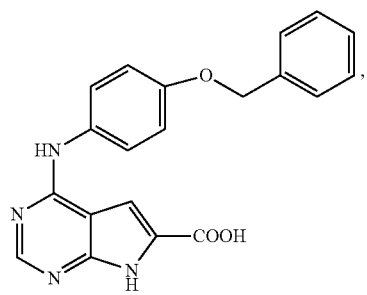

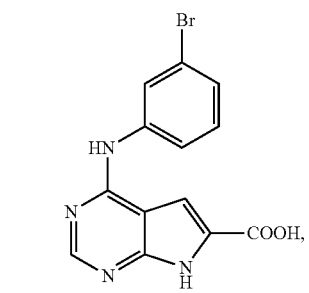

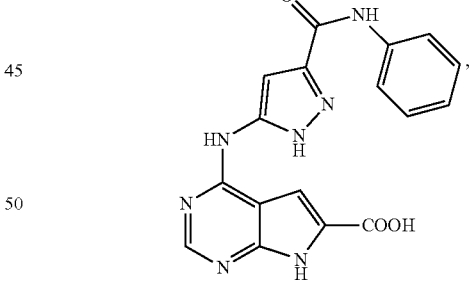

, and

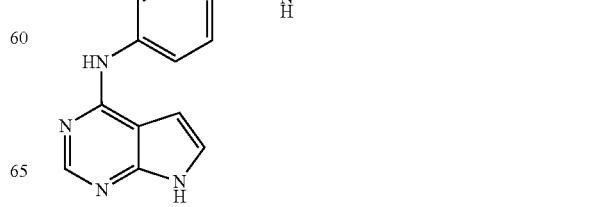

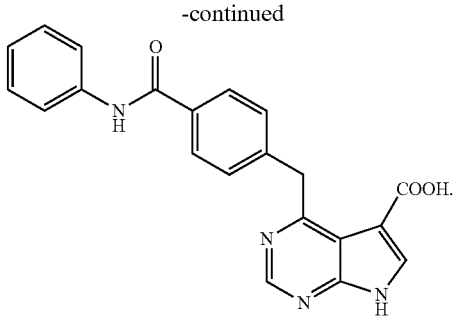

Of course, all of the embodiments and the examples of the compounds of Formulas (I-2) and (I-3) can also be a pharmaceutically acceptable salt of the compounds described.

Further, a method for inhibiting aurora kinase A, aurora kinase B activity, and/or epidermal growth factor activity with the compound of Formula (I-2) or (I-3), wherein the method comprises the step of administering a therapeutically effective amount of the compound of Formula (I-2) or (I-3) to subject (e.g. a mammal) in need thereof is disclosed and described herein in greater detail below.

Method of Forming Compounds:

With reference to FIGS. 1-5, the synthesis for various compounds of Series I-XII are described in Schemes 1-9 below. The synthetic procedures utilized are adapted from well documented protocols such as organometallic couplings and can be applied to the pyrrolo[2,3-d]pyrimidine scaffold. Synthetic routes that have been well established have been incorporated for compound synthesis. The reactions can be monitored via thin layer chromatography for reaction completion and purified using normal phase flash chromatography (Teledyne Isco) with gradient elution (10% methanol/chloroform). Percent yields can be determined for each reaction. To ensure rigor, compound identity can be confirmed by $^1$H, $^{13}$C, $^{19}$F nuclear magnetic resonance (NMR) and LC-MS analysis using the Shimadzu research core. For accurate mass determination, high-resolution mass analysis (HRMS) can be utilized. Percent purity can be determined by analytical HPLC (Shimadzu Core). All synthetic reagents can be purchased from Millipore Sigma. The purchased chemicals can be authenticated in lab using NMR and mass analysis. All novel compounds and products of novel reactions can be authenticated using NMR, melting point determination, HRMS and elemental analysis.

Series I and II can be synthesized in two ways, as shown in Scheme 1 below. One approach may involve the nucleophilic displacement of 80 (commercially available from Millipore Sigma) with the amino substituted benzoic acid 81. The carboxylic acid 82 may be converted to the corresponding acid chloride 83 with thionyl chloride. Phosphorus oxychloride may also be used as an alternate for acid chloride synthesis. Displacement with the appropriate aniline under basic conditions may yield Series I and II. Another approach may involve the synthesis of the appropriate amino benzanilide, first followed by nucleophilic substitution of as shown in Scheme 1. In the event that nucleophilic displacement is not suitable, a palladium catalyzed Buchwald-Hartwig coupling protocol may be utilized. In the event that the acid chloride displacement between 83 and 84 is not suitable, a standard peptide coupling protocol may be utilized. The acid in 85 may be activated using hydroxybenzotriazole (HOBt), hexafluorophosphate benzotriazole tetramethyl uronium (HBTU) in dimethylformamide (DMF) as solvent followed by reaction with the appropriate aniline 84 in the presence of diethylamine to yield Series I and II.

Figure 18:
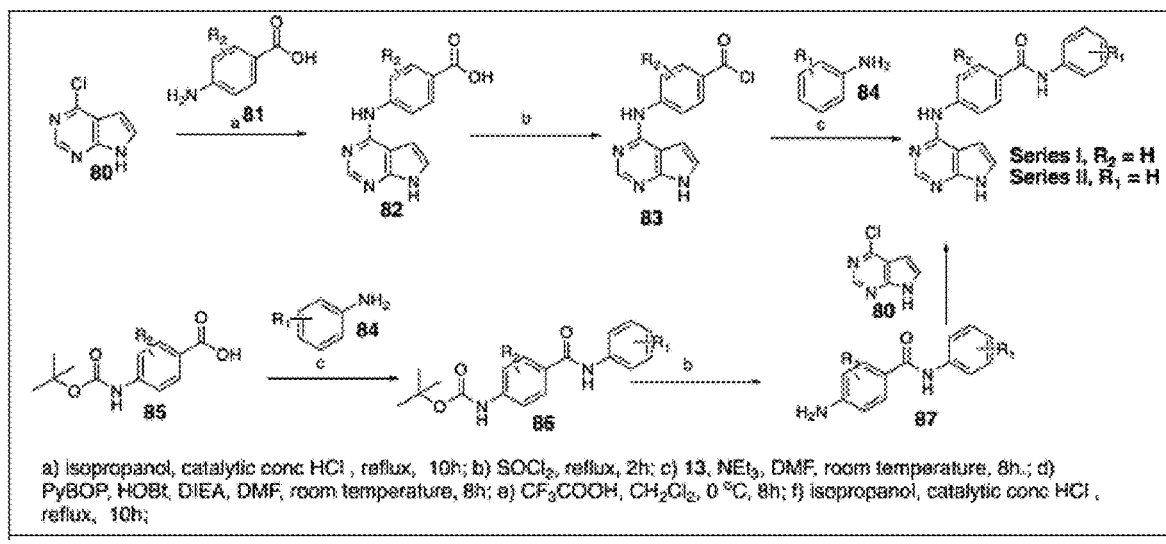
FIGS. 18-24 are synthesis schemes illustrating non-limiting embodiments of methods of forming compounds.

Scheme 1: Synthesis of Compounds in Series I and II. See FIG. 18.

Series III may be synthesized as described in Scheme 2 below using similar methods as described in Scheme 1 above. The appropriate heteroaromatic iodides may be purchased from Millipore Sigma. Reaction with bispinacolborane using the Miyaura borylation protocol may yield the corresponding boronates. Suzuki coupling with commercially available tert-butyloxycarbonyl (Boc) protected aryl bromide may yield 91.

Protection of the NH in 88 may be necessary to prevent side reactions and lower yields. The amine may be protected by 2-(trimethylsilyl)ethoxymethyl (SEM) chloride. Alternate bases, reaction conditions and palladium catalysts may be attempted. In the event that the Miyaura borylation or Suzuki coupling does not proceed as expected, we can attempt alternate direct coupling protocols such as Heck coupling or nickel catalyzed Negishi coupling. Deprotection of the Boc group in 91 under acidic conditions followed by nucleophilic substitution of 80 may yield Series III. Deprotection of 91 to yield 92, followed by nucleophilic substitution of 80 as described under preliminary studies should afford Series III.

Figure 19:
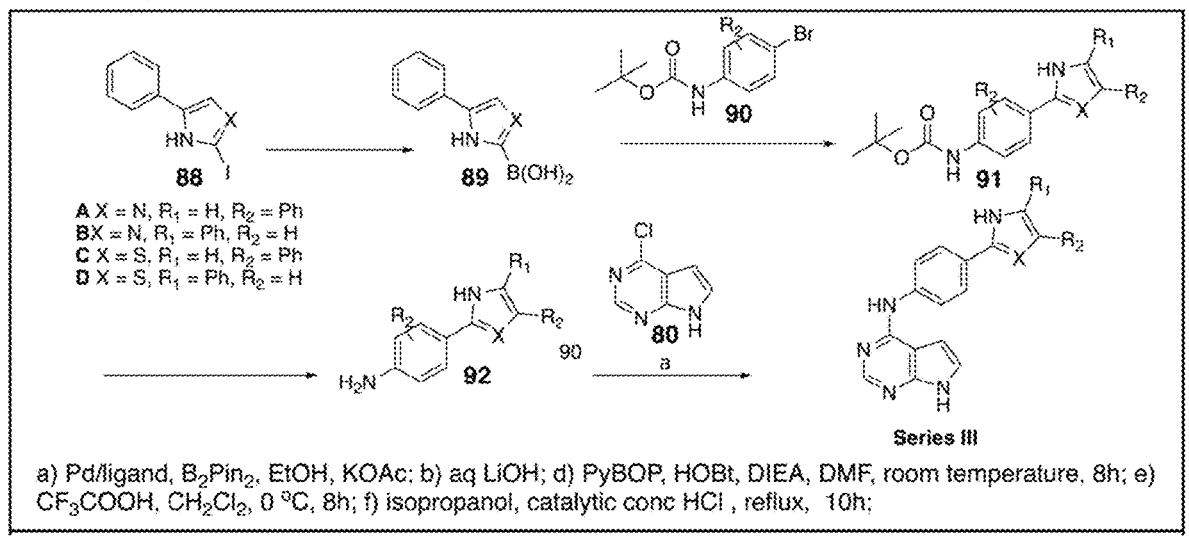

Scheme 2: Synthesis of Series III. See FIG. 19.

Series IV may be synthesized similar to Scheme 1 above using the appropriately substituted amino pyrrazole or aminopyridine. A nucleophilic substitution reaction on 80 with 3-aminopyrazole may yield 94. The acid group may be further reacted with aniline, using 1-(3-dimethylaminopropyl)-3-ethylcarbodiimide hydrochloride (EDC) to give the corresponding acetanilide, or alternatively converted to the corresponding acid chloride using thionyl chloride followed by displacement by aniline in pyridine to 47. Aminopyrazole or aminopyridine may be utilized to synthesize 93-97 as described for 47.

Figure 20:
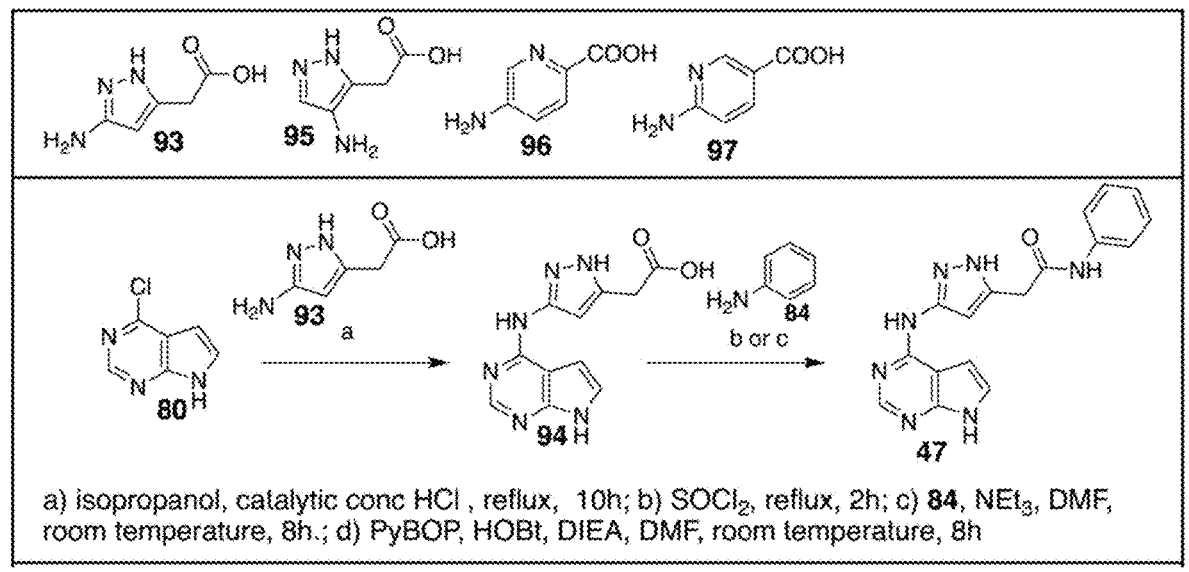

Scheme 3: Synthesis of Series IV. See FIG. 20.

Series V may be synthesized as described in Scheme 4 below. Synthesis of 51 may involve a nucleophilic displacement of 80 with the appropriately substituted amine 99. Starting material 80 for Series V may also be commercially available from Millipore Sigma.

Figure 21:
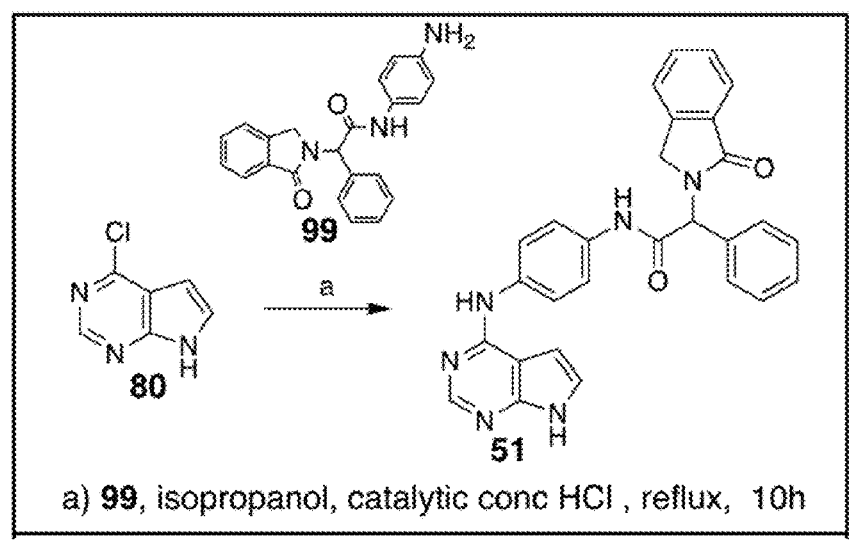

Scheme 4: Synthesis of Series V. See FIG. 21.

Series VI may be synthesized as described in Scheme 5 below. The reaction of starting material 100 with SEM chloride may yield 101. In the event that SEM chloride is not suitable, trityl chloride may be utilized. Suzuki coupling with the appropriate alkyl/aryl boronates may be utilized to yield 102. The protocol may involve reaction for 20 hours at 100° C. or reaction under microwave catalyzed conditions, such as microwave catalyzed organometallic coupling reactions.

Figure 22:
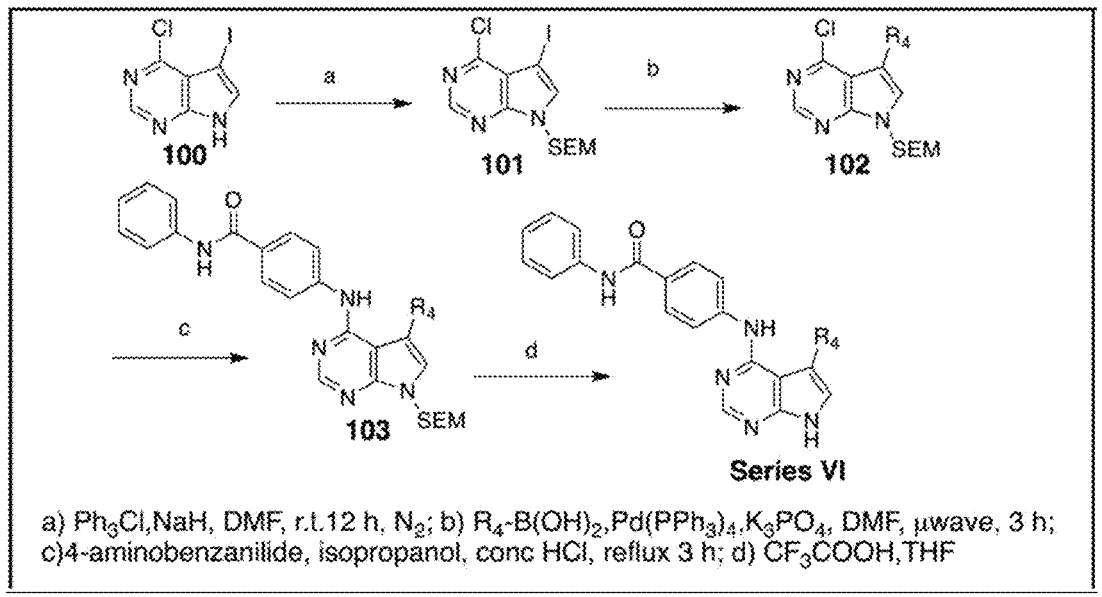

Scheme 5: Synthesis of Series VI. See FIG. 22.

Series VII may be synthesized similar to Series I using nucleophilic displacement of 102 with the appropriate aniline followed by acid catalyzed deprotection of the SEM group may be utilized to yield Series VII. Nucleophilic displacement with the appropriate aniline followed by SEM deprotection may be used to yield Series VII as shown in Scheme 6 below.

Figure 23:
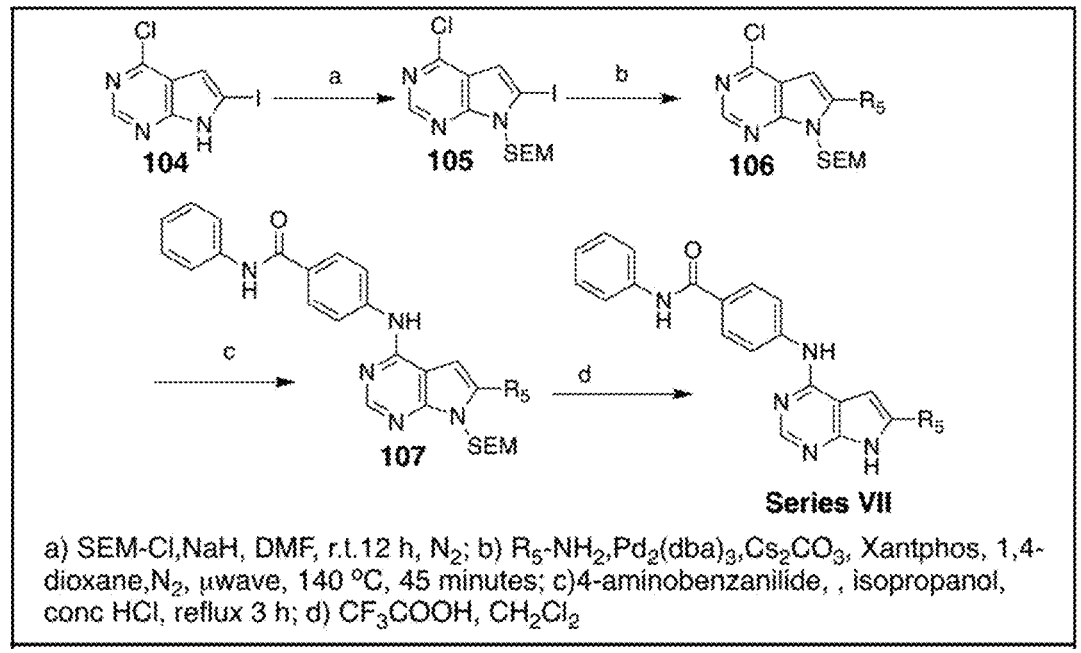

Scheme 6: Synthesis of Series VII. See FIG. 23.

Series VIII-XI may be synthesized as described in Scheme 7 below. For example, compounds in Series X and XI are close analogs of pyrrolopyrimidines reported by Le Brazidec et al. Structure-based design of 2,6,7-trisubstituted-7H-pyrrolo[2,3-d]pyrimidines as Aurora kinases inhibitors. Bioorg Med Chem Lett 2012, 22, 4033-4037, which is hereby incorporated by reference in its entirety, and can be synthesized as reported. An alternate synthetic protocol as described by Skelton et al. Preparation of bicyclic heteroaryl derivatives as AKT protein kinase inhibitors. World Intellectual Property Organization, WO2013078254 A1 (2013-05-30), which is hereby incorporated by reference in its entirety, could also be utilized as described in Scheme 7 starting from commercially available 108. Base catalyzed alkylation of the pyrrole nitrogen using the procedure described by Planken et al. Discovery of N-((3R,4R)-4-Fluoro-1-(6-((3-methoxy-1-methyl-1H-pyrazol-4-yl)amino)-9-methyl-9H-purin-2-yl)pyrrolidine-3-yl)acrylamide (PF-06747775) through Structure-Based Drug Design: A High Affinity Irreversible Inhibitor Targeting Oncogenic EGFR Mutants with Selectivity over Wild-Type EGFR. *J. Med. Chem.* 2017, 60, 3002-3019, which is hereby incorporated by reference in its entirety, or using a Mitsunobu alkylation as an alternate route for N7 alkylation. Suzuki coupling of the 6-iodo followed by palladium catalyzed coupling of the 2-chloro under inert conditions can yield Series VIII-IX. This has been previously described by Miyaura et al. Palladium-Catalyzed Cross-Coupling Reactions of Organoboron Compounds. *Chem. Rev.* 1995, 95, 2457-2483 for aryl iodides, and Zhang et al. Palladium-Imidazol-2-ylidene Complexes as Catalysts for Facile and Efficient Suzuki Cross-Coupling Reactions of Aryl Chlorides with Arylboronic Acids. *J. Org. Chem.* 1999, 64, 3804-3805 for aryl chlorides, which are hereby incorporated by reference in their entirety.

Figure 24:
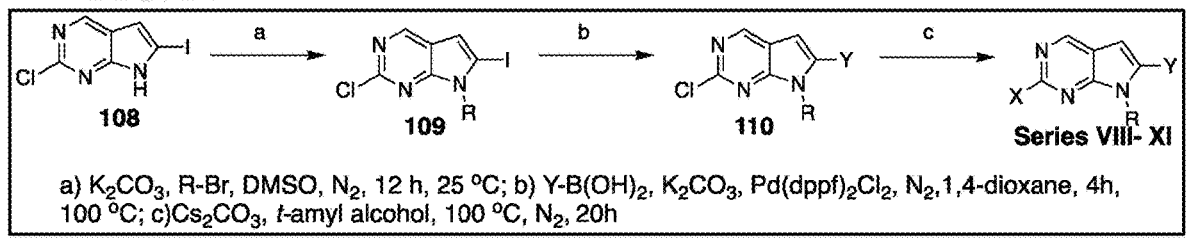

Scheme 7: Synthesis of Series VIII-XI. See FIG. 24.

Series XII may be synthesized similar to Scheme 6 described previously for Series VII using the appropriately substituted boronic acid and 105. Compound 11 of Series XII can be synthesized using modification of the protocol reported for Series VI. Other pyrazolopyrimidine-based compounds may be formed in accordance with Radi et al. J. Med. Chem. 2013, 56, 5382-5394 and Gehringer et al. ChemMedChem 2014, 9, 2516-2527, which are hereby incorporated by reference in their entirety. Tricyclic-based compounds may be formed in accordance with Gehringer et al. ChemMedChem 2014, 9, 2516-2527 and Zhang et al. Bioorganic & Medicinal Chemistry 19 (2011) 3585-3594, which are hereby incorporated by reference in their entirety.

Figure 6:
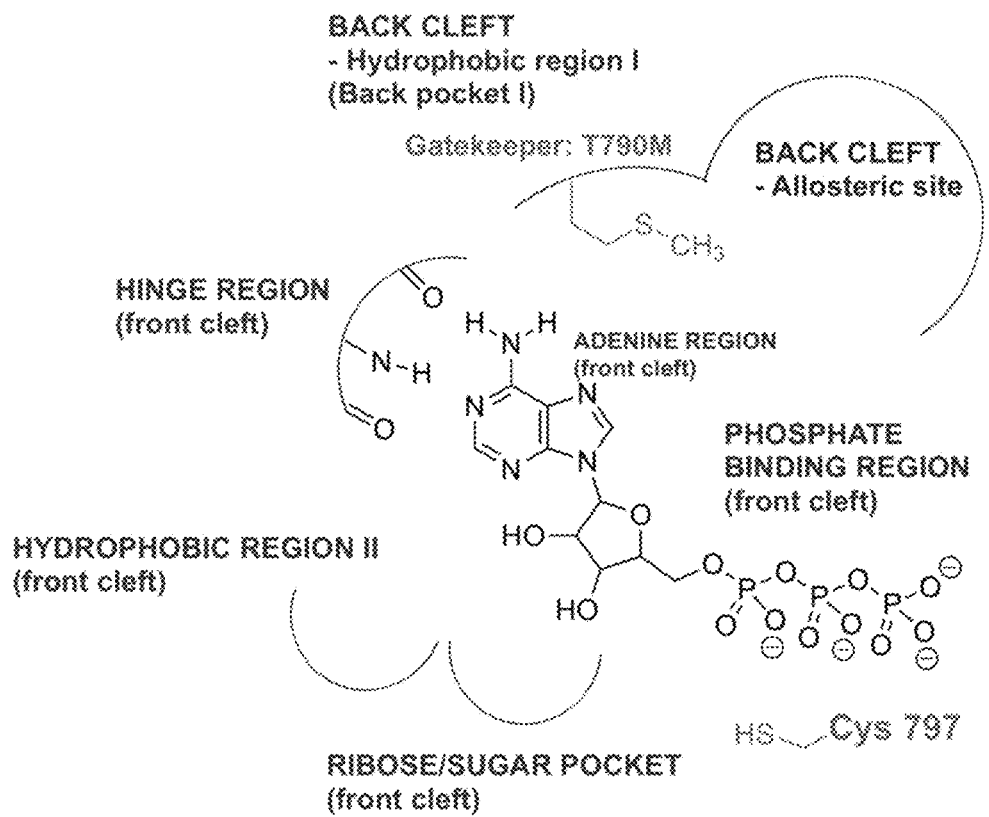
FIG. 6 is a representation of a chemical structure illustrating a non-limiting embodiment of the compound in a binding pocket.

Method of Identifying Compounds:

With reference to FIG. 6, the ATP pocket of kinases may be made up of different regions. The first-generation EGFR inhibitors, erlotinib and gefitinib may be reversible. Type I inhibitors may bind to the active state of EGFR and interact with the ATP site and the smaller hydrophobic pocket (hydrophobic region I) of the back cleft. Afatinib and osimertinib may bind within the ATP pocket of EGFR similar to Type I inhibitors and may target a cysteine residue adjacent to the ATP site. Type II EGFR inhibitors, lapatinib and neratinib are also EGFR inhibitors. These Type II EGFR inhibitors may demonstrate allosteric as well as ATP-competitive kinase inhibition. These Type II EGFR include long hydrophobic sidechains that extend deep within hydrophobic pocket of the back cleft accessing the allosteric site.

Figure 7:
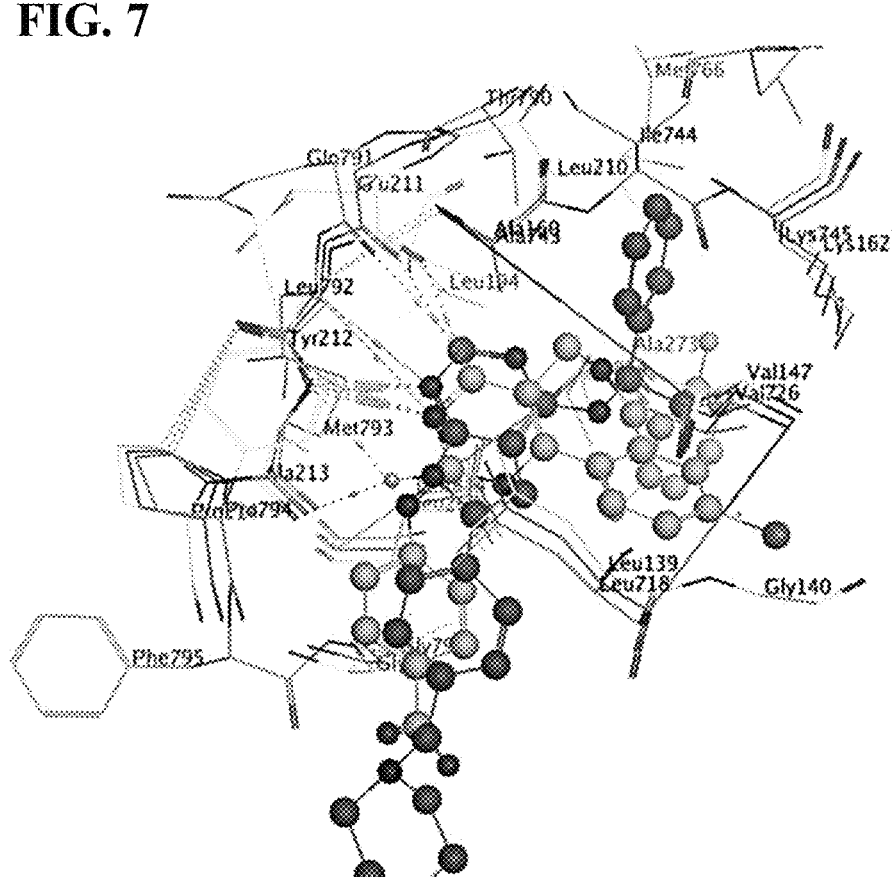
FIG. 7 is another representation of a chemical structure illustrating a non-limiting embodiment of the compound in a binding pocket.
Figure 8:
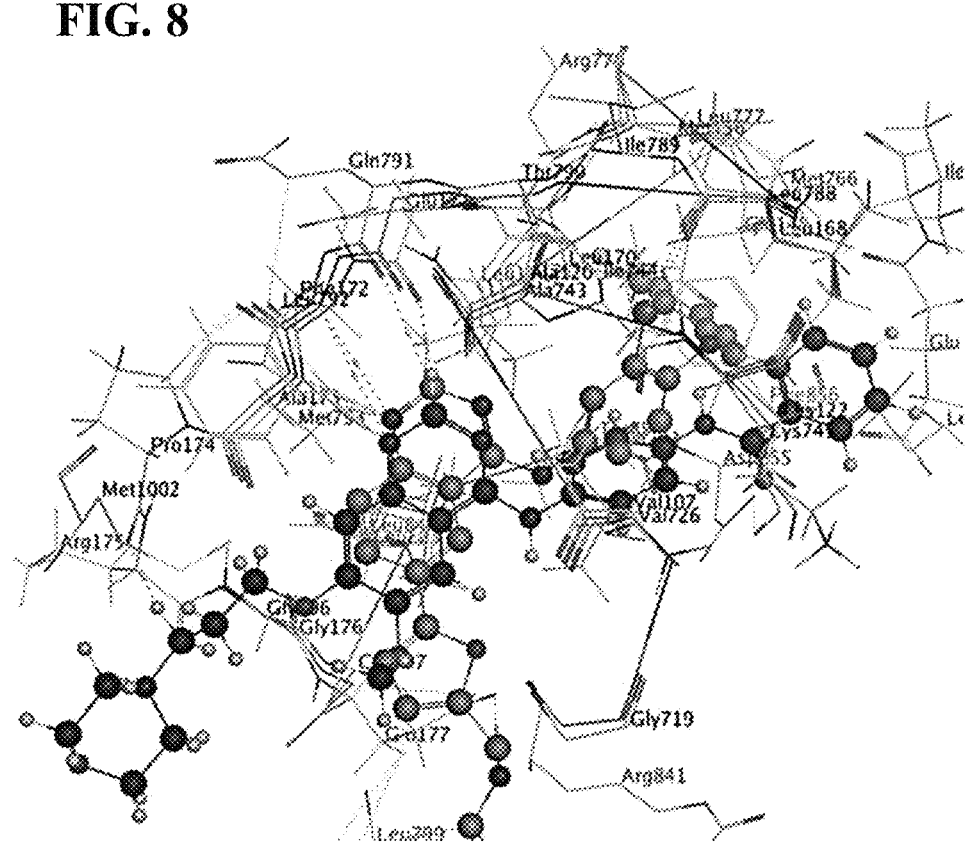
FIG. 8 is another representation of a chemical structure illustrating a non-limiting embodiment of the compound in a binding pocket.

With reference to FIGS. 7 and 8, the AURK inhibitors may be ATP-competitive with distinct modes of binding to the ATP pocket of AURKA and AURKB. Alisertib, a selective AURKA inhibitor, may bind predominantly in the front cleft with interactions observed with the hinge region residues, Ala 213 and Met 793 and interactions within the ribose pocket, adenine region and phosphate binding region, and minimal interactions in Hydrophobic region I and the back pocket. Selective AURKB inhibitors such as barasertib and ZM 447439 may bind within the hinge region, adenine region and incorporate sidechains that interact within hydrophobic region I and extend further into the back cleft of AURKB.

The ATP binding site from reported crystal structures of EGFR in the inactive Type II conformation (PDB code: 2JIV), EGFR in the Type I active conformation (PDB code: 1M17), L858R EGFR (PDB code: 2ITT), AURKA from (PDB code: 3E5A) and AURKB (PDB code: 2VRX) and the computational software, Molecular Operating Environment (MOE 2019.10) suite may be utilized as starting points for modeling experiments. Alignment may be conducted using the Align/minimize feature in MOE to determine similarities and differences in the pockets. Aligned poses may be viewed to note any major geometrical changes and deviations from the crystallized pose.

With particular reference to FIG. 7, the ATP pocket of EGFR (active conformation) overlapped with the ATP pocket of AURKA is shown. With particular reference to FIG. 8, the ATP pocket of EGFR in the inactive conformation overlapped with AURKB is shown. In various embodiments, the pockets show several similarities among the different regions both based on size and sequence homology. The sequence similarity between the ATP pockets of EGFR and AURK may be calculated using the program in MOE and root mean square deviation (rmsd) may be 0.87 for EGFR in the inactive conformation and AURKB and may be 0.83 for EGFR in the active conformation and AURKA. In certain embodiments, values of rmsd<1 indicate high similarity. The amino acids in the hydrophobic region I and ribose pocket may largely overlap between EGFR and AURK. The allosteric pocket shown in FIG. 8 having the inactive conformation of EGFR may overlay on the back pocket of AURKB. Variations may be found in the amino acids of the hinge region of EGFR and AURKs, however the hinge region amino acids may interact through their common peptide backbone and may be found to overlay in their interaction pattern of one hydrogen bond donor and one hydrogen bond acceptor. This may be seen through the backbone carbonyl and amide NH for AURKA (through Ala 213), EGFR (through Met793 and Leu 792) and AURKB (through Ala 173). As a result, variations in binding may not be expected for the hinge region of EGFR and AURK. To ensure rigor, the alignment protocols may be repeated with different reported crystal structures for EGFR including (1XKK, 3W33), AURKA (4DHF, 2X81), and AURKB (4AF3,5EYK) and may yield similar results for sequence similarity and orientation of residues in the ATP pocket.

Although the invention has been described in connection with specific preferred embodiments, it should be understood that the invention as claimed should not be unduly limited to these specific embodiments. While at least one exemplary embodiment has been presented in the foregoing detailed description of the disclosure, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention. It being understood that various changes may be made in the function and arrangement of elements described in an exemplary embodiment without departing from the scope of the disclosure as set forth in the appended claims.

EXAMPLES

The following examples are included to demonstrate various embodiments as contemplated herein. It should be appreciated by those of skill in the art that the techniques disclosed in the examples which follow represent techniques discovered by the inventor(s) to function well in the practice of the invention, and thus can be considered to constitute desirable modes for its practice. However, those of skill in the art should, in light of the present disclosure, appreciate that many changes can be made in the specific embodiments which are disclosed and still obtain a like or similar result without departing from the spirit and scope of the invention. All percentages are in wt. % and all measurements are conducted at 23° C. unless indicated otherwise.

The pyrrolo[2,3-d]pyrimidine heterocycle is a scaffold that may exhibit varied kinase inhibition. The pyrrolo[2,3-d]pyrimidine heterocycle may exhibit reversible and irreversible EGFR inhibition. In various embodiments, a 4,6-disubstituted pyrrolo[2,3-d]pyrimidines may be a multi-targeted kinase inhibitors of EGFR, platelet derived growth factor receptor kinase b (PDGFRb) and vascular endothelial growth factor receptor kinase (VEGFR). Additionally, a 2,4,7-trisubstituted pyrrolo[2,3-d]pyrimidines may be a dual checkpoint kinase and aurora kinase inhibitors.

Figure 9:
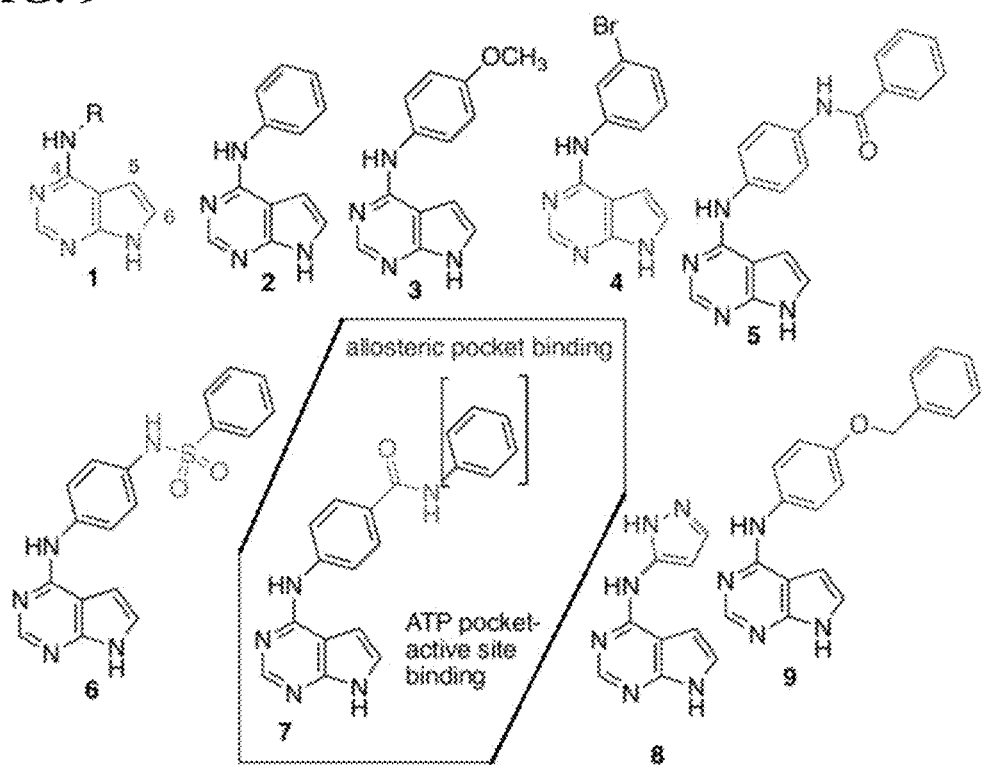
FIG. 9 are representation of chemical structures illustrating a non-limiting embodiment of the compound in a binding pocket

With reference to FIG. 9, compounds having the general structure 1 may be effective as dual EGFR/AURK inhibitors. Compound 3 may be a micromolar EGFR/AURKA inhibitor, while compound 4 may be a nanomolar EGFR and micromolar AURKA inhibitor. While nanomolar EGFR inhibition was seen for multiple compounds, AURKA inhibition remained in the micromolar range for several compounds of general structure 1.

To improve aurora kinase inhibition, pharmacophoric fragments (shown in blue) may be combined using a molecular hybridization approach from aurora kinase inhibitor, ZM 447439 with structure 1 of the initial series of pyrrolo[2,3-d]pyrimidines to yield 5. Compounds 6 and 7 may be synthesized as analogs of compound 5 with varied linkers. Compounds 8 and 9 may include side chains seen in AURK inhibitors and Type II EGFR inhibitors respectively. The ADP detection assays may be used to evaluate allosteric kinase inhibitors. Compounds 2-9 were evaluated in an ADP detection assay externally using the Kinomescan KdELECT platform from Discover X.

With reference to Table 1 below, compound 6 exhibits AURKB inhibition followed by compound 5. Compound 7 exhibits dual EGFR/AURKB inhibition with sub-micromolar EGFR and single-digit micromolar AURKB inhibition. Compound 7 exhibits a preference for AURKB over AURKA. Compounds 5, 6 and 8 were dual AURKB/AURKA inhibitors with no EGFR inhibition. Compound 9 retained potent EGFR inhibition with modest AURKB inhibition.

TABLE 1

Enzymatic inhibition and predicted compound properties

| Compound | EGFR $K_d$ (µM) | L858R EGFR $K_d$ (µM) | AURKA $K_d$ (µM) | AURKB $K_d$ (µM) | MW (g/mol) | clogP |
|---|---|---|---|---|---|---|
| 3 | 3 | 2.8 | 3.5 | 12 | 240.27 | 2.23 |
| 4 | 0.067 | 0.05 | 3.4 | 4.8 | 289.14 | 3.02 |
| 5 | 30 | 30 | 1.6 | 0.47 | 329.26 | 3.44 |
| 6 | 15 | 0.71 | 2.1 | 0.24 | 365.42 | 2.59 |
| 7 | 0.44 | 0.90 | 16 | 1.5 | 329.26 | 3.44 |
| 8 | 18 | 14 | 1.2 | 1.5 | 200.21 | 0.54 |
| 9 | 0.087 | 0.68 | >30 | 9.8 | 316.36 | 3.6 |
| Staurosporine | 0.12 | | 0.24 | 0.44 | | |

Figure 10:
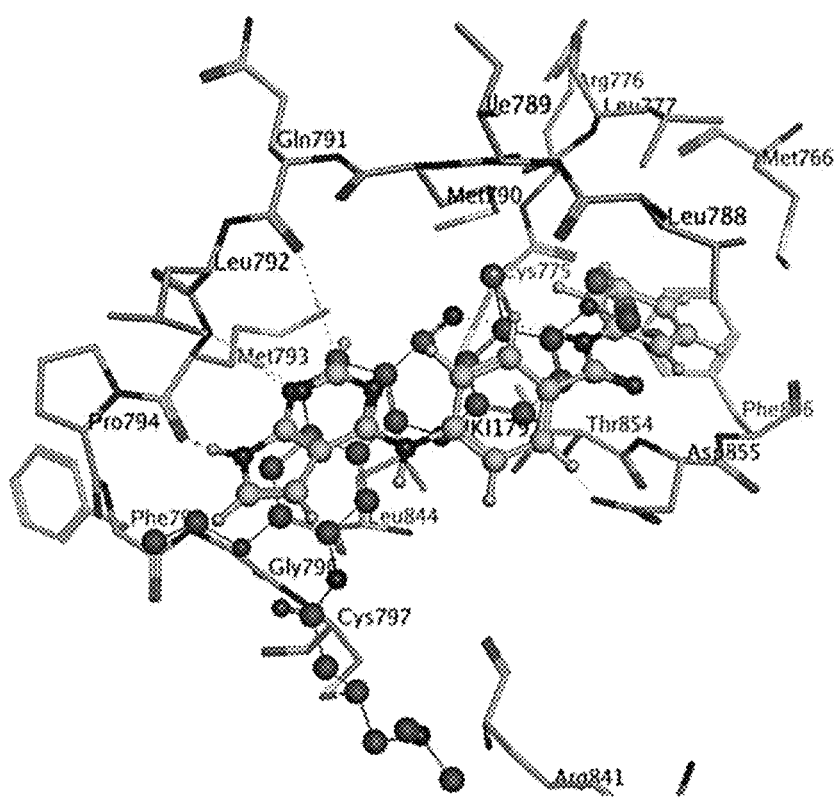
FIG. 10 is another representation of a chemical structure illustrating a non-limiting embodiment of the compound in a binding pocket.
Figure 11:
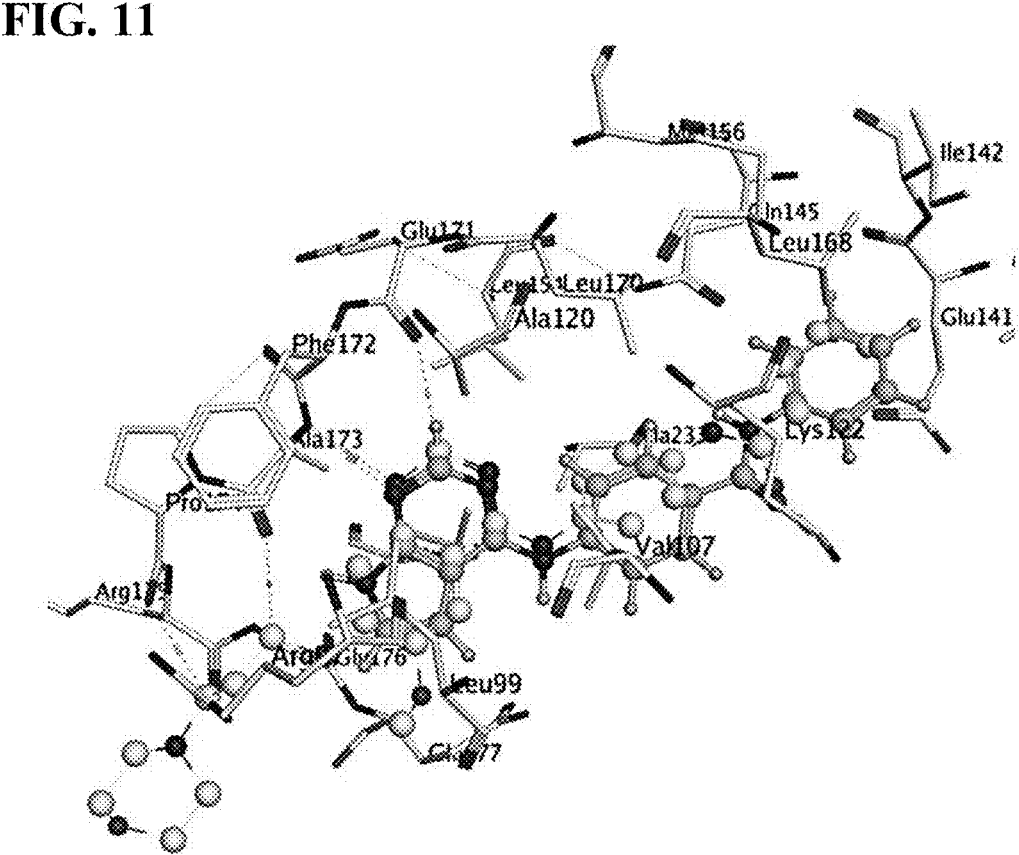
FIG. 11 is another representation of a chemical structure illustrating a non-limiting embodiment of the compound in a binding pocket.

With reference to FIGS. 10 and 11, molecular modeling for compound 7 within EGFR (PDB: 2JIV) 39 and AURKB (PDB: 2VRX) 50 showed that it interacted through two hydrogen bonds to the hinge region of both EGFR and AURK. Compound 7 was found to bind deep within the hydrophobic pocket of EGFR and to overlay on a type II EGFR inhibitor, neratinib (FIG. 3). Within AURKB, the 4-benzanilido sidechain overlays on the sidechain of ZM 447439 extending into hydrophobic region I and the deep back pocket. The docking protocol used for molecular modeling has been developed in our lab previously. The docking model was validated based on rmsd for the crystallized ligand in its original pose versus the docked pose. The docked poses were examined for fit and interactions within the binding pocket and binding energies were calculated using LigX within MOE. Rigor was established by performing three iterations and using varied crystal structures. Modeling within AURKA showed that 7 was oriented toward solvent within the phosphate binding region of the kinase explaining the poor AURKA inhibition observed. Pharmacokinetic properties and toxicity were calculated for target compounds using the program, DataWarrior (Table 1). Compounds 2-9 were smaller than standards with molecular weights<400, while standards, gefitinib, alisertib and barasertib were much larger in 450-600 range, clog P<5. Lipophilic ligand efficiency (LLE) is drug discovery parameter that correlates potency to lipophilicity of the molecule. The LLE for compound 7 is 0.51 and for gefitinib is 0.46 suggesting that compound 7 is more efficient (a small size and greater contribution to potency). Additionally, no toxicity/mutagenic risks were identified, suggesting that compound 7 provides a good lead for further study.

Figure 12:
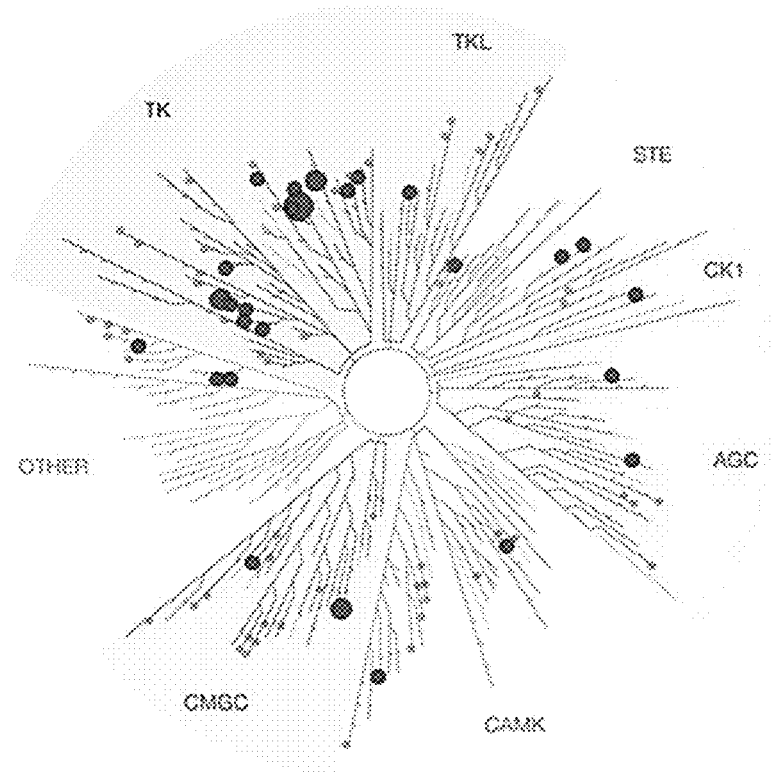
FIG. 12 is a graphical representation illustrating a non-limiting embodiment of an assessment for selectivity of the compound against various kinases.
Figure 13:
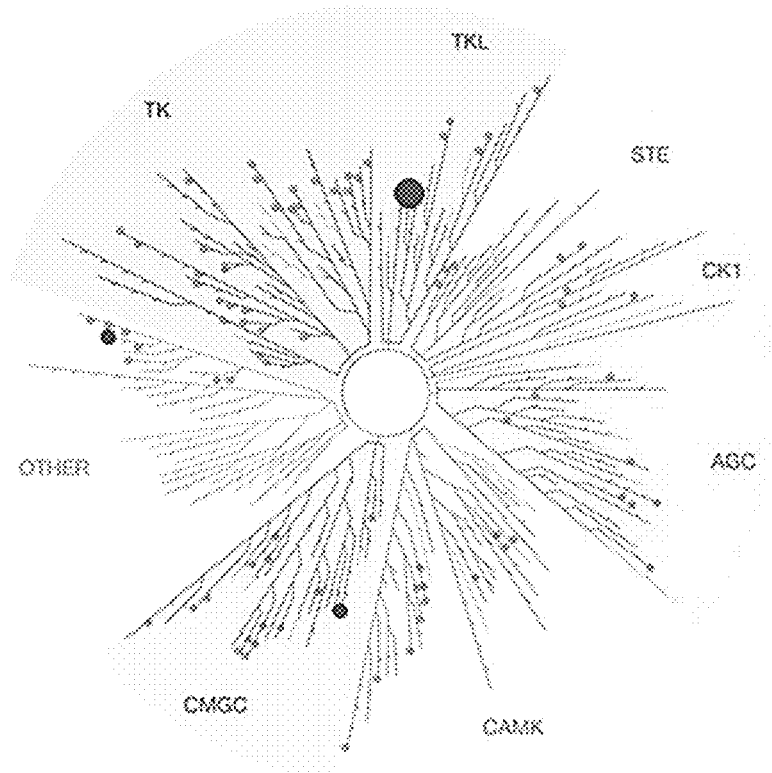
FIG. 13 is another graphical representation illustrating a non-limiting embodiment of an assessment for selectivity of the compound against various kinases.
Figure 14:
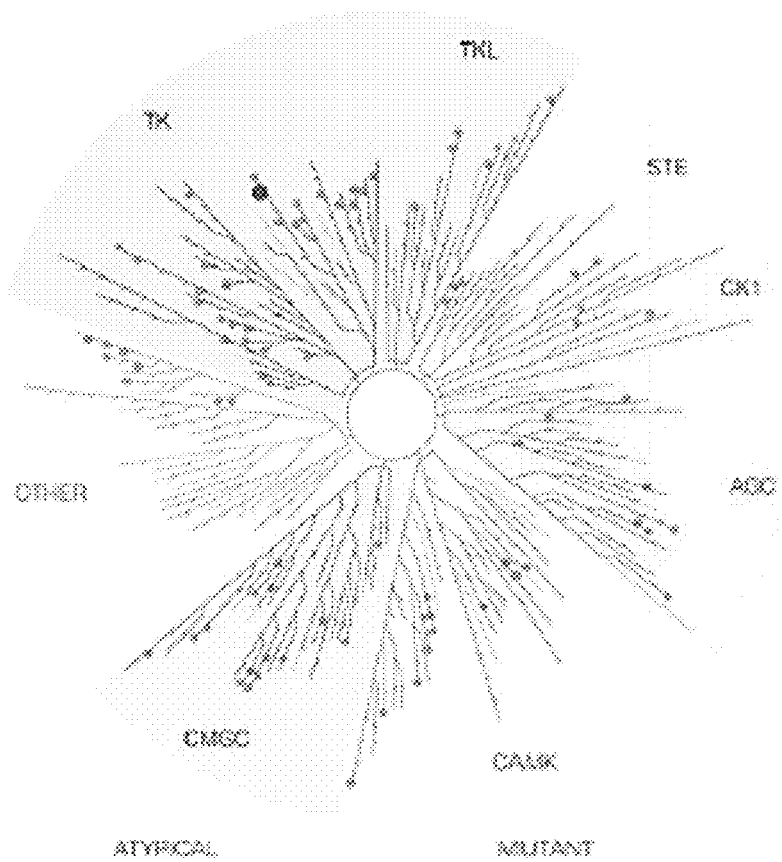
FIG. 14 is another graphical representation illustrating a non-limiting embodiment of an assessment for selectivity of the compound against various kinases.

With reference to FIGS. 12-14, compound 3 (micromolar, dual EGFR/AURKA inhibitor), compound 5 (sub-micromolar, dual AURKA/AURKB inhibitor) and compound 7 (sub-micromolar, dual EGFR/AURKB inhibitor) were evaluated externally for selectivity against 97-different kinases of the scanEDGE platform of DiscoverX. This is a reliable platform that has been used to assess selectivity for most approved kinase inhibitors. Selectivity scores were calculated that allow a comparison of different compound selectivity. The selectivity score, S(35) was calculated by dividing the kinases inhibited by >35% with the total number of kinases tested in the panel. Smaller scores indicate higher selectivity. Compound 7 was highly selective compared to compound 3 further validating it as a lead molecule for dual EGFR/AURKB inhibition.

It is to be understood that the appended claims are not limited to express and particular compounds, compositions, or methods described in the detailed description, which may vary between particular embodiments which fall within the scope of the appended claims. With respect to any Markush groups relied upon herein for describing particular features or aspects of various embodiments, different, special, and/or unexpected results may be obtained from each member of the respective Markush group independent from all other Markush members. Each member of a Markush group may be relied upon individually and or in combination and provides adequate support for specific embodiments within the scope of the appended claims.

Further, any ranges and subranges relied upon in describing various embodiments of the present invention independently and collectively fall within the scope of the appended claims, and are understood to describe and contemplate all ranges including whole and/or fractional values therein, even if such values are not expressly written herein. One of skill in the art readily recognizes that the enumerated ranges and subranges sufficiently describe and enable various embodiments of the present invention, and such ranges and subranges may be further delineated into relevant halves, thirds, quarters, fifths, and so on. As just one example, a range "of from 0.1 to 0.9" may be further delineated into a lower third, i.e., from 0.1 to 0.3, a middle third, i.e., from 0.4 to 0.6, and an upper third, i.e., from 0.7 to 0.9, which individually and collectively are within the scope of the appended claims, and may be relied upon individually and/or collectively and provide adequate support for specific embodiments within the scope of the appended claims. In addition, with respect to the language which defines or modifies a range, such as "at least," "greater than," "less than," "no more than," and the like, it is to be understood that such language includes subranges and/or an upper or lower limit. As another example, a range of "at least 10" inherently includes a subrange of from at least 10 to 35, a subrange of from at least 10 to 25, a subrange of from 25 to 35, and so on, and each subrange may be relied upon individually and/or collectively and provides adequate support for specific embodiments within the scope of the appended claims. Finally, an individual number within a disclosed range may be relied upon and provides adequate support for specific embodiments within the scope of the appended claims. For example, a range "of from 1 to 9" includes various individual integers, such as 3, as well as individual numbers including a decimal point (or fraction), such as 4.1, which may be relied upon and provide adequate support for specific embodiments within the scope of the appended claims.

The present invention has been described herein in an illustrative manner, and it is to be understood that the terminology which has been used is intended to be in the nature of words of description rather than of limitation. Many modifications and variations of the present invention are possible in light of the above teachings. The present invention may be practiced otherwise than as specifically described within the scope of the appended claims. The subject matter of all combinations of independent and dependent claims, both single and multiple dependent, is herein expressly contemplated.

What is claimed is:

1. A compound of Formula (I-2):

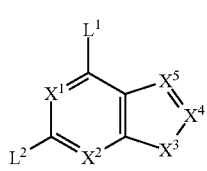
(I-2)

or a pharmaceutically acceptable salt or stereoisomer thereof,
wherein:
$L^1$ is —NR$^4$—R$^1$;
$R^4$ is H;
$R^1$ is

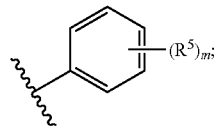

(i) each $R^5$ is independently F, Br, $CH_2C(O)NHC_{2-6}$ alkenyl, $CH_2C(O)OH$, $CH_2NHC(O)C_{2-6}$ alkenyl, $CH_2$-phenyl, $C(O)OH$, $C(O)OC_{3-6}$ alkyl, $C(O)OC_{3-6}$ cycloalkyl, $NHC_{3-6}$ alkyl, $NHC(O)C_{1-6}$ alkyl, $NHC(O)C_{2-6}$ alkenyl, $NHC(O)$—$C_{2-6}$ alkenylene-$C_{1-6}$ alkylene-$N(C_{1-10}$ alkyl)$_2$, $C_{3-6}$ cycloalkylamine, or phenyl; or (ii) each $R^5$ is independently:

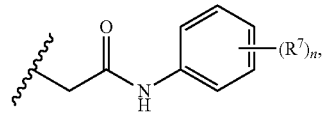

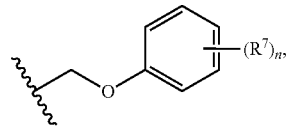

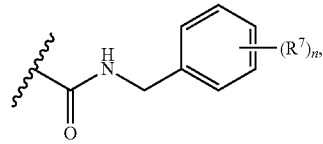

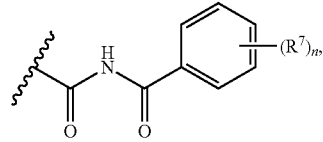

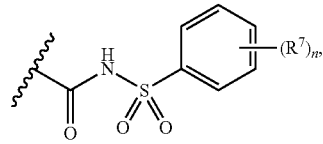

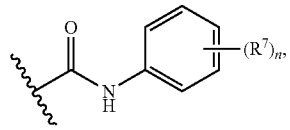

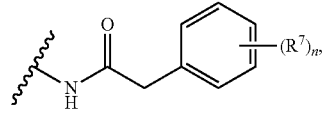

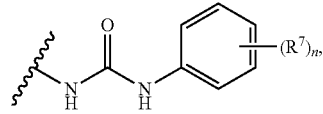

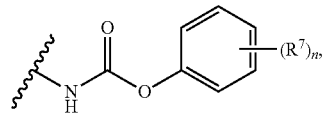

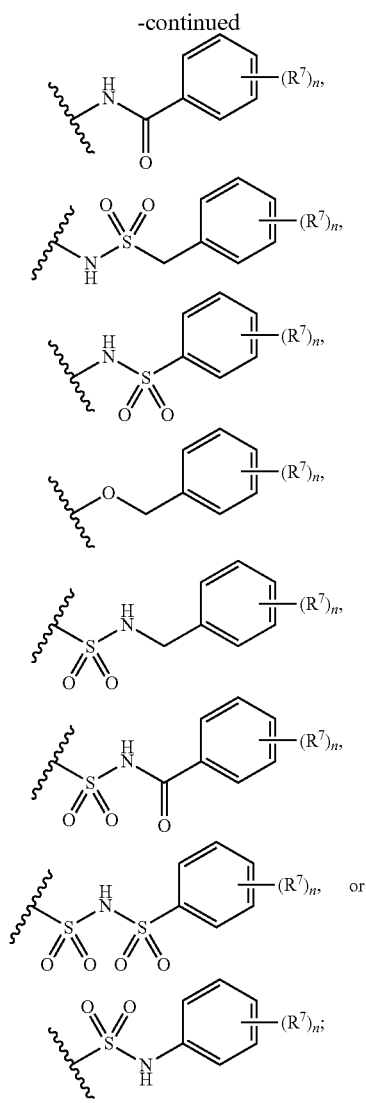

each n is independently 1, 2, 3, 4, or 5;
each $R^7$ is independently H, halo, CN, $NO_2$, $C_{1-10}$ alkyl, $C_{1-10}$ haloalkyl, $C_{2-10}$ alkenyl, $C_{2-10}$ alkynyl, $C(O)C_{1-6}$ alkyl, $C(O)NHC_{1-6}$ alkyl, $NH_2$, $NHC_{1-10}$ alkyl, $N(C_{1-10}$ alkyl$)_2$, $NHC(O)C_{1-6}$ alkyl, $NHC(O)C_{2-6}$ alkenyl, $NHC(O)$—$C_{2-6}$ alkenylene-$C_{1-6}$ alkylene-N$(C_{1-10}$ alkyl$)_2$, $NHS(O)_2C_{1-10}$ alkyl, OH, $OC_{1-10}$ alkyl, $OC_{1-10}$ haloalkyl, SH, $SC_{1-10}$ alkyl, $S(O)C_{1-6}$ alkyl, $S(O)_2NHC_{1-6}$ alkyl, $C_{3-10}$ cycloalkyl, $C_{4-10}$ cycloalkenyl, a monocyclic 3- to 8-membered ring, or a bicyclic 6- to 12-membered ring;
wherein each monocyclic 3- to 8-membered ring or bicyclic 6- to 12-membered ring is fully saturated, partially unsaturated, or fully unsaturated;
wherein each monocyclic 3- to 8-membered ring independently contains one or more carbon atoms and optionally and independently contains one, two, or three heteroatoms independently selected from the group consisting of nitrogen, oxygen, and sulfur; and
wherein each bicyclic 6- to 12-membered ring independently contains one or more carbon atoms and optionally and independently one, two, three, four, five, or six heteroatoms independently selected from the group consisting of nitrogen, oxygen, and sulfur;

$X^1$ is N;
$L^2$ is H;
$X^2$ is N;
$X^3$ is —NH—;
$X^4$ is $CR^2$;
$R^2$ is C(O)OH or —$X^6R^3$;
$X^6$ is —$C(O)NH(CH_2)_m$—;
$R^3$ is phenyl, pyrazolyl, isoxazolyl, tetrazolyl, pyridinyl, or pyrimidinyl, wherein the phenyl, pyrazolyl, isoxazolyl, tetrazolyl, pyridinyl, or pyrimidinyl is optionally substituted with 1, 2, or 3 substituents independently selected from the group consisting of halo, CN, $NO_2$, $C_{1-6}$ alkyl, $C_{1-6}$ haloalkyl, $C_{1-6}$ alkyl-$NH_2$, $CH_2C(O)NHC_{2-10}$ alkenyl, $CH_2C(O)OH$, $CH_2NHC(O)C_{2-10}$ alkenyl, $CH_2$-phenyl, $C(O)NHC_{1-10}$ alkyl, $C(O)N(C_{1-10}$ alkyl$)_2$, $C(O)NHC_{2-10}$ alkenyl, $C(O)NHC(O)OC_{1-6}$ alkyl, $C(O)NHC(O)OC_{3-6}$ cycloalkyl, $C(O)NHC(O)O$phenyl, $C(O)NHC(O)OC_{1-6}$ heteroaryl, $C(O)NH$pyrrolidinyl, $C(O)NH$piperidinyl, $C(O)NH$piperazinyl, $C(O)NH$phenyl, $C(O)NHC_{1-6}$ heteroaryl, C(O)OH, $NH_2$, $NHC_{1-10}$ alkyl, $N(C_{1-10}$ alkyl$)_2$, $NHC_{2-10}$ alkenyl, NH—$C_{2-10}$ alkynylene-$N(C_{1-10}$ alkyl$)_2$, $NHC(O)$ $C_{1-10}$ alkyl, $NHC(O)C_{2-10}$ alkenyl, $NHC(O)$—$C_{2-10}$ alkenylene-$C_{1-6}$ alkylene-$N(C_{1-10}$ alkyl$)_2$, $NHC(O)C$ $(O)OC_{1-6}$ alkyl, $NHC(O)C(O)OC_{3-6}$ cycloalkyl, $NHC(O)C(O)OC_{1-6}$ heteroaryl, $NHC(O)NHC_{1-10}$ alkyl, $NHC(O)N(C_{1-10}$ alkyl$)_2$, $NHC(O)NH$pyrrolidinyl, $NHC(O)NH$piperidinyl, $NHC(O)NH$piperazinyl, $NHC(O)NH$phenyl, $NHC(O)NHC_{1-6}$ heteroaryl, $NHC(O)C_{3-6}$ cycloalkyl, $NHC_{6-10}$ aryl, OH, $OC_{1-6}$ alkyl, $OC_{1-6}$ haloalkyl, $C_{3-6}$ cycloalkyl, $C_{3-6}$ cycloalkyl-$NH_2$, and phenyl;
$X^5$ is CH; and
each m is independently 1, 2, 3, 4, or 5.

2. The compound of claim 1, wherein the compound is of the following formula:

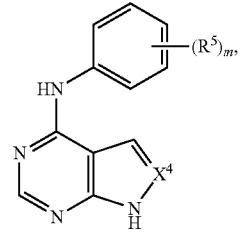

or a pharmaceutically acceptable salt or stereoisomer thereof,
wherein:
m is 1; and
$R^5$ is:

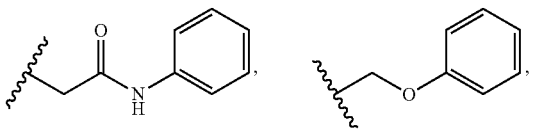

-continued

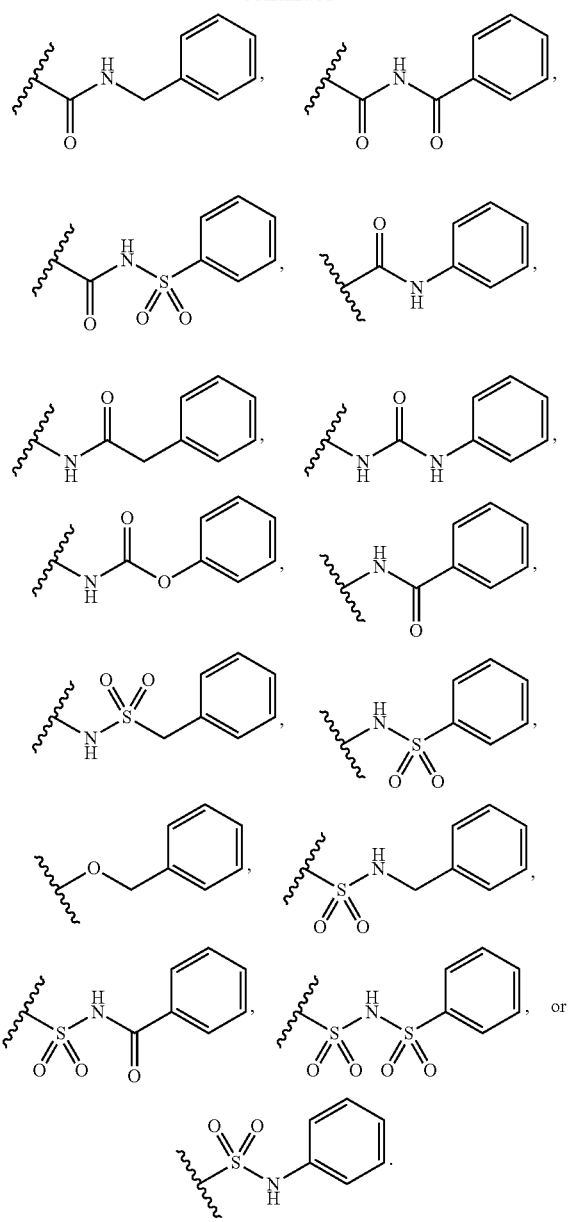

3. The compound of claim 1, wherein the compound is of the following formula:

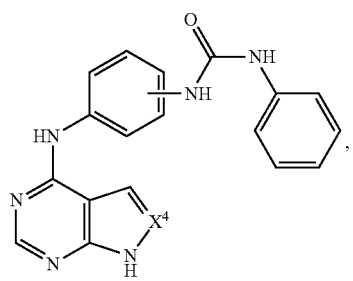

or a pharmaceutically acceptable salt or stereoisomer thereof.

4. The compound of claim 1, wherein the compound is of the following formula:

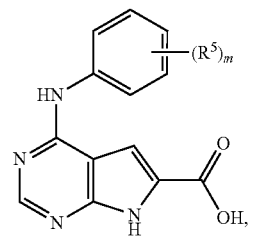

or a pharmaceutically acceptable salt or stereoisomer thereof.

5. The compound of claim 4, wherein the compound is:

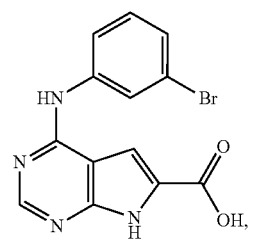 [SMILES: O=C(O)c1cc2c(Nc3cccc(Br)c3)ncnc2[nH]1]

or a pharmaceutically acceptable salt thereof.

6. The compound of claim 4, wherein the compound is selected from the group consisting of:

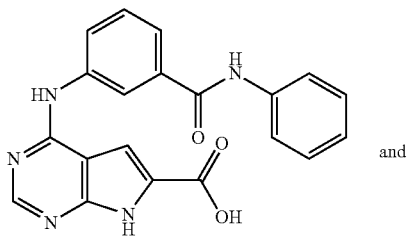

and

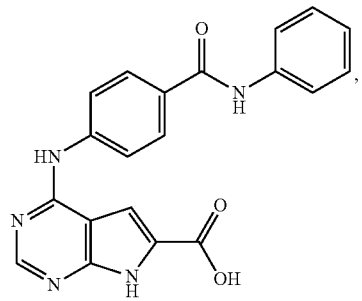

or a pharmaceutically acceptable salt thereof.

7. The compound of claim 4, wherein the compound is:

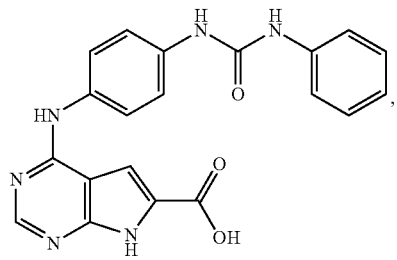 [SMILES: O=C(Nc1ccccc1)Nc1ccc(Nc2ncnc3[nH]c(C(=O)O)cc23)cc1]

or a pharmaceutically acceptable salt thereof.

8. The compound of claim 4, wherein the compound is:

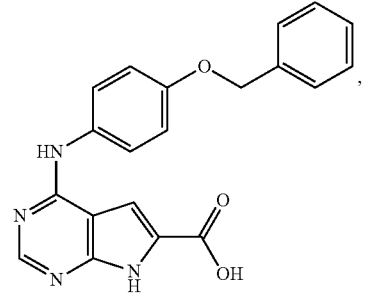 [SMILES: O=C(O)c1cc2c(Nc3ccc(OCc4ccccc4)cc3)ncnc2[nH]1]

or a pharmaceutically acceptable salt thereof.

9. The compound of claim 4, wherein the compound is:

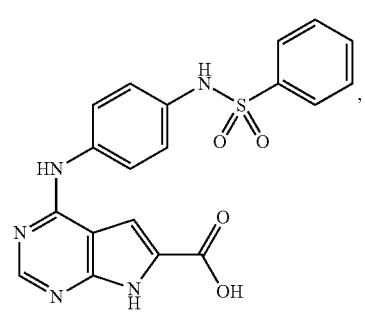 [SMILES: O=C(O)c1cc2c(Nc3ccc(NS(=O)(=O)c4ccccc4)cc3)ncnc2[nH]1]

or a pharmaceutically acceptable salt thereof.

10. A pharmaceutical composition comprising a pharmaceutically acceptable carrier and a therapeutically effective amount of a compound of claim 1, or a pharmaceutically acceptable salt or stereoisomer thereof.

11. A method for inhibiting aurora kinase A (AURKA) activity, aurora kinase B (AURKB) activity, and/or epidermal growth factor receptor (EGFR) activity in a subject, wherein the method comprises administering to the subject in need thereof a therapeutically effective amount of a compound of claim 1, or a pharmaceutically acceptable salt or stereoisomer thereof.

12. A compound selected from the group consisting of:

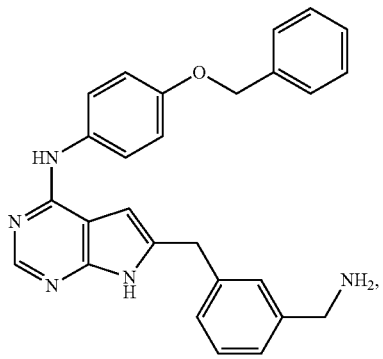

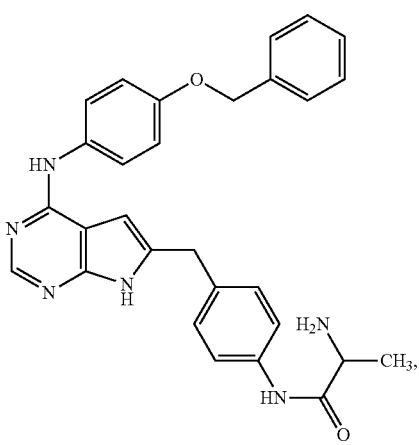

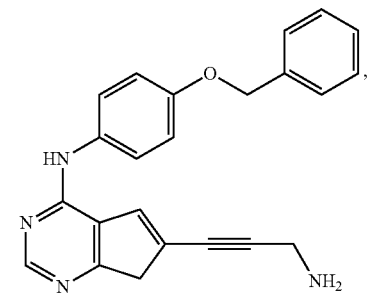

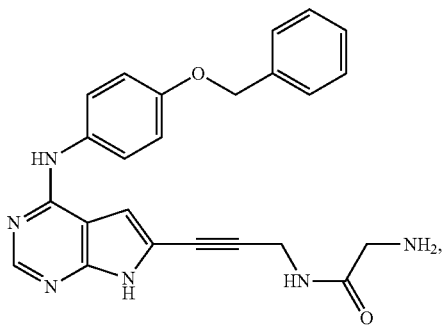

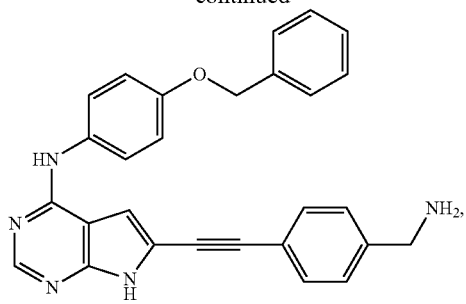
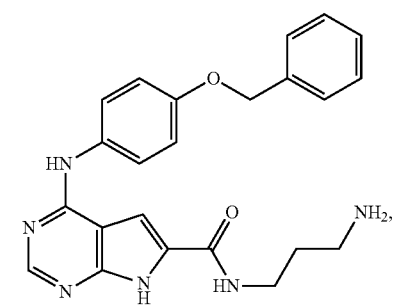
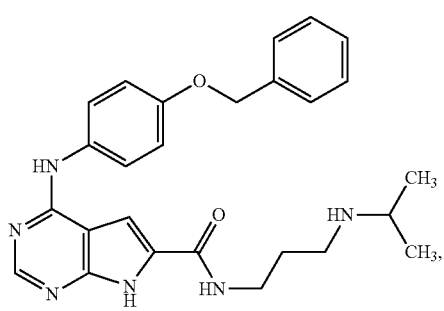
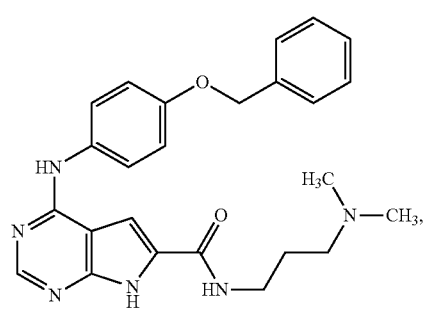
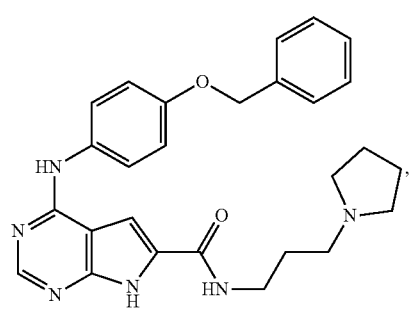 [SMILES: O=C(NCCCN1CCCC1)c1cc2c(Nc3ccc(OCc4ccccc4)cc3)ncnc2[nH]1]
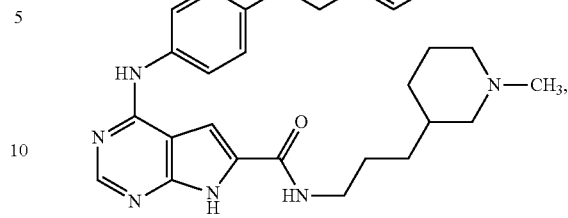
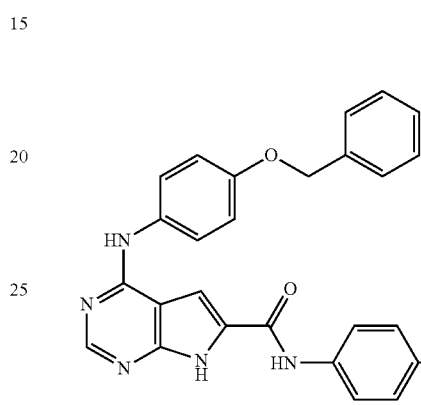
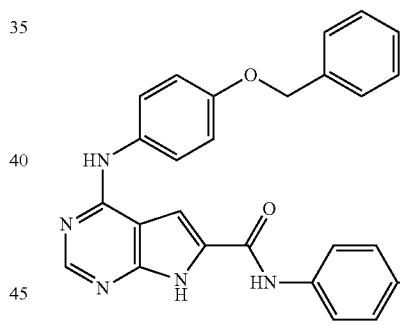
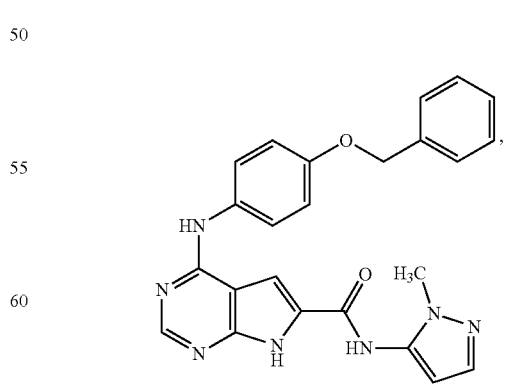
or a pharmaceutically acceptable salt or stereoisomer thereof.

13. The compound of claim 12, wherein the compound is:

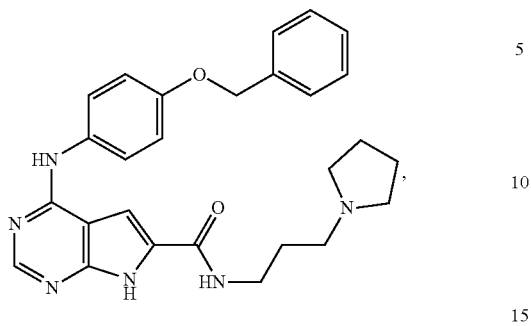

or a pharmaceutically acceptable salt thereof.

14. A pharmaceutical composition comprising a pharmaceutically acceptable carrier and a therapeutically effective amount of a compound of claim 12, or a pharmaceutically acceptable salt or stereoisomer thereof.

15. A method for inhibiting aurora kinase A (AURKA) activity, aurora kinase B (AURKB) activity, and/or epidermal growth factor receptor (EGFR) activity in a subject, wherein the method comprises administering to the subject in need thereof a therapeutically effective amount of a compound of claim 12, or a pharmaceutically acceptable salt or stereoisomer thereof.

* * * * *